(12) United States Patent
Kim et al.

(10) Patent No.: US 11,202,811 B2
(45) Date of Patent: Dec. 21, 2021

(54) LACTOBACILLUS HAVING VARIOUS FUNCTIONS, AND USE THEREOF

(71) Applicants: University-Industry Cooperation Group of Kyung Hee University, Yongin-si (KR); Navipharm Co, Ltd, Suwon-si (KR)

(72) Inventors: Dong Hyun Kim, Seoul (KR); Myung Joo Han, Seoul (KR)

(73) Assignees: University-Industry Cooperation Group of Kyung Hee University; Navipharm Co., Ltd

( * ) Notice: Subject to any disclaimer, the term of this patent is extended or adjusted under 35 U.S.C. 154(b) by 176 days.

(21) Appl. No.: 15/759,915

(22) PCT Filed: Sep. 7, 2016

(86) PCT No.: PCT/KR2016/009994
§ 371 (c)(1),
(2) Date: Mar. 14, 2018

(87) PCT Pub. No.: WO2017/047968
PCT Pub. Date: Mar. 23, 2017

(65) Prior Publication Data
US 2019/0030097 A1 Jan. 31, 2019

(30) Foreign Application Priority Data

Sep. 15, 2015 (KR) .................. 10-2015-0130124
Jan. 15, 2016 (KR) .................. 10-2016-0005018

(51) Int. Cl.
| | | |
|---|---|---|
| *A61K 35/747* | (2015.01) | |
| *A23L 33/135* | (2016.01) | |
| *A61K 36/48* | (2006.01) | |
| *C12N 1/20* | (2006.01) | |
| *A61P 25/28* | (2006.01) | |
| *A61K 35/745* | (2015.01) | |
| *C12R 1/25* | (2006.01) | |
| *C12R 1/225* | (2006.01) | |
| *A61K 35/00* | (2006.01) | |

(52) U.S. Cl.
CPC .......... *A61K 35/747* (2013.01); *A23L 33/135* (2016.08); *A61K 35/745* (2013.01); *A61K 36/48* (2013.01); *A61P 25/28* (2018.01); *C12N 1/205* (2021.05); *A23V 2002/00* (2013.01); *A23Y 2220/43* (2013.01); *A23Y 2220/67* (2013.01); *A61K 2035/115* (2013.01); *C12R 2001/225* (2021.05); *C12R 2001/25* (2021.05)

(58) Field of Classification Search
CPC .............. A23L 33/135; C12R 2001/25; A23Y 2220/67; A61K 35/747; A61K 35/745; A61K 2035/115
See application file for complete search history.

(56) References Cited

U.S. PATENT DOCUMENTS

| | | | |
|---|---|---|---|
| 9,603,878 B2 | 3/2017 | Berry et al. | |
| 9,801,915 B2 | 10/2017 | Bel-Rhlid et al. | |
| 10,028,983 B2 | 7/2018 | Yamamoto et al. | |
| 2005/0180962 A1* | 8/2005 | Raz ................ | A61K 9/0095 424/93.45 |
| 2011/0046235 A1 | 2/2011 | Bel-Rhlid et al. | |
| 2011/0046236 A1 | 2/2011 | Czarnik et al. | |
| 2014/0030194 A1* | 1/2014 | McKenna .............. | A61K 35/74 424/48 |
| 2015/0174177 A1 | 6/2015 | Bel-Rhlid et al. | |
| 2015/0250834 A1 | 9/2015 | Tsai et al. | |
| 2015/0306158 A1 | 10/2015 | Kim et al. | |
| 2016/0000841 A1 | 1/2016 | Yamamoto et al. | |
| 2016/0006841 A1 | 1/2016 | Gurevich et al. | |

(Continued)

FOREIGN PATENT DOCUMENTS

| | | |
|---|---|---|
| EP | 1624762 A1 | 2/2007 |
| JP | 2011518570 | 6/2011 |
| JP | 2012136436 | 7/2012 |

(Continued)

OTHER PUBLICATIONS

Sultana, Reshma et al., "Strain-dependent Augmentation of Tight-junction Barrier Function in Human Primary Epidermal Keratinocytes by Lactobacillus and Bifi-dobacterium Lysates," Applied and Environmental Microbiology, [electronic publishing] Jun. 14, 2013, vol. 79, No. 16, pp. 4887-4894.

(Continued)

*Primary Examiner* — Taeyoon Kim
*Assistant Examiner* — Tiffany M Gough
(74) *Attorney, Agent, or Firm* — Fish & Richardson P.C.

(57) ABSTRACT

The present invention provides novel *Lactobacillus* sp. strains, novel *Bifidobacterium* sp. strains, or lactic acid bacteria mixtures thereof, which are isolated from kimchi or human feces. A certain *Lactobacillus* sp. strain or certain *Bifidobacterium* sp. strain according to the present invention is isolated from kimchi or human feces, and thus is highly safe, and has various physiological activities such as anti-oxidant activity, β-glucuronidase inhibitory activity, lipopolysaccharide (LPS) production inhibitory activity or tight junction protein expression-inducing activity. Accordingly, a certain *Lactobacillus* sp. strain, certain *Bifidobacterium* sp. strain or mixture thereof according to the present invention may be used as a functional food or medicinal material useful for the prevention, alleviation or treatment of intestinal damage, liver injury, allergic disease, inflammatory disease, or obesity.

4 Claims, 25 Drawing Sheets
Specification includes a Sequence Listing.

(56) References Cited

U.S. PATENT DOCUMENTS

| | | | |
|---|---|---|---|
| 2017/0368114 A1 | 12/2017 | Kim et al. | |
| 2018/0028582 A1 | 2/2018 | Bel-Rhlid et al. | |

FOREIGN PATENT DOCUMENTS

| | | |
|---|---|---|
| JP | 2015521613 | 7/2015 |
| JP | 2015526085 | 9/2015 |
| KR | 10-2006-0119045 | 11/2006 |
| KR | 10 0818360 | 4/2008 |
| KR | 10-00759751 | 8/2008 |
| KR | 1020080075971 | 8/2008 |
| KR | 10-2009-0116051 | 11/2009 |
| KR | 10-2010-0010015 | 1/2010 |
| KR | 20110057550 | 6/2011 |
| KR | 20130002911 | 1/2013 |
| KR | 1020130000024 | 1/2013 |
| KR | 10-2013-0056264 | 5/2013 |
| KR | 10-2013-0092182 | 8/2013 |
| KR | 10-2014-0006509 | 1/2014 |
| KR | 20140023241 | 2/2014 |
| KR | 10-1470347 | 12/2014 |
| KR | 20150047687 | 5/2015 |
| KR | 1020150142527 | 12/2015 |
| KR | 1020160101660 | 8/2016 |
| RU | 2316586 | 2/2008 |
| WO | WO 2008/157728 | 12/2008 |
| WO | WO 2013/190068 | 12/2013 |
| WO | WO 2014/130540 | 8/2014 |
| WO | WO/2017/047968 | 3/2017 |
| WO | WO2017047962 | 3/2017 |

OTHER PUBLICATIONS

Ulluwishewa, Dulantha et al., "Regulation of Tight Junction permeability by Intestinal Bacteria and Dietary Components," The Journal of Nutrition [electronic publishing] Mar. 23, 2011, vol. 141, No. 5, pp. 769-776.

Karczewski, Jurgen et al., "Regulation of Human Epithelial Tight Junction Proteins by Lactobacillus plantarum In Vivo and protective Effects on the Epithelial Barrier," American Journal of Physiology Gastrointestinal and liver Phisiology [electronic publishing] Mar. 11, 2010, vol. 298, No. 6, pp. G851-G859.

ISA/KR, International Search Report for PCT/KR2016/009994 (dated Jan. 10, 2017).

Anderson et al., *Lactobacillus plantarum DSM 2648 is a potential probiotic that enhances intestinal barrier function*, FEMS Microbiol Lett 309(2):184-192 (Aug. 2010).

Anderson et al., *Lactobacillus plantarum MB452 enhances the function of the intestinal barrier by increasing the expression levels of genes involved in tight junction formation*, BMC Microbiology, 10:316-(2010) (11 pages).

Bouhafs et al., *Protective effects of probiotic Lactobacillus plantarum BJ0021 on liver and kidney oxidative stress and apoptosis induced by endosulfan in pregnant rats*, Renal Failure, 37(8):1370-1378 (2015).

EP Extended Search Report for App No. EP16846789.2, dated Apr. 5, 2019 (14 pages).

Fasano, *Leaky gut and autoimmune diseases*, Clin Rev Allergy Immunol., 42(1):71-8 (Feb. 2012).

Han et al., Hepatoprotective effect of lactic acid bacteria, inhibitors of beta-glucuronidase production against intestinal microflora, Arch Pharm Res., 28(3):325-9 (2005).

HM446157, DDDBJ, Jul. 20, 2010 (1 page).

JQ446498, DDBJ, Mar. 12, 2012 (2 pages).

Kim et al., *Lactobacillus brevis OK56 ameliorates high-fat diet-induced obesity in mice by inhibiting NF-kappaB activation and gut microbial LPS production*, Journal of Functional Foods, 13:183-191 (Mar. 2015).

KP763934, DDBJ, Jul. 29, 2015 (1 page).

Liu et al., *Lactobacillus plantarum prevents the development of colitis in IL-10-deficient mouse by reducing the intestinal permeability*, Mol Biol Rep, 38(2):1353-61 (Feb. 2011).

RU Office Action for App No. 2018113245 dated Mar. 28, 2019 (14 pages) (English translation).

Szabo et al., *Gut-liver axis and sensing microbes*, Diq Dis 28(6):737-44 (2010).

AU Examination Report No. 1 for App No. AU2016322617 dated Mar. 29, 2019 (3 pages).

International Preliminary Report on Patentability and Written Opinion for Intl App No. PCT/KR2016/009994, dated Mar. 20, 2018 (11 pages).

JP Office Action for App No. JP 2018-513778, dated Feb. 12, 2019 (w English translation) ( 8 pages).

Agerholm-Larsen et al., *The effect of a probiotic milk product on plasma cholesterol: a meta-analysis of short-term intervention studies*, Eur J Clin Nutr, 54(11):856-860 (2000).

Hivak et al., *One-year application of probiotic strain Enterococcus faecium M-74 decreases serum cholesterol levels*, Bratisl Lek Listy, 106(2):67-72 (2005).

Lukacova et al., *In vitro testing of selected probiotic characteristics of Lactobacillus plantarum and Bifidobacterium longum* Journal of Food and Nutrition Research, 45:77-83 (2006).

Park, et al., *Artemisia asiatica extracts protect against ethanol-induced injury in gastric mucosa of rats* J. Gastroenterol. Hepatol, 23(6):976-984 (2008).

Pridmore et al., *The genome sequence of the probiotic intestinal bacterium Lactobacillus johnsonii NCC 533* Proc Natl Acad Sci USA. 101(8):2512-7 (2004).

Sousa et al., *Effect of Lactobacillus acidophilus supernatants on body weight and leptin expression in rats*; BMC complementary and alternative medicine, 8(5):1-8 (2008).

Suriasih et al., *Microbiological and Chemical Properties of Kefir Made of Bali Cattle Milk*, Food Science and Quality Management 6:112-22 (2012).

Catanzaro et al., *Boswellia serrata Preserves Intestinal Epithelial Barrier from Oxidative and Inflammatory Damage*, PLoS One. 2015;10(5):e0125375. Published May 8, 2015. doi:10.1371/journal.pone.0125375 (15 pages).

Jang, et al., *Simultaneous Amelioratation of Colitis and Liver Injury in Mice by Bifidobacterium longum LC67 and Lactobacillus plantarum LC27* Sci Rep 8:7500 (2018).

BR Office Action for App No. BR112018005195-0, dated Aug. 3, 2020 (8 pages) (with English translation).

Huang et al., Lactobacillus plantarum strains as potential probiotic cultures with cholesterol-lowering lowering activity; J. Dairy Sci., 96:2746-2753 (2012).

Martens et al., Probiotics for the airways: Potential to improve epithelial and immune homeostasis, Allergy, 73: 1954-1963.

Quesada-Vazquez et al., Diet, Gut Microbiota and Non-Alcoholic Fatty Liver Disease: Three Parts of the Same Axis; Cells 9(176) (17 pages).

RU Decision to Grant for App No. 2018113245 dated Jul. 29, 2020 (14 pages) (with English translation).

RU Office Action for App No. 2018113245 dated Sep. 24, 2019 (9 pages) (with English translation).

Australian Examination Report No. 2 in AU Appln. No. 2016324846, dated Nov. 8, 2019, 4 pages.

Canadian Office Action in CA Appln. No. 2998877, dated Nov. 22, 2018, 4 pages.

Canadian Office Action in CA Appln. No. 2998877, dated Sep. 5, 2019, 3 pages.

European Extended Search Report in EP Appln. No. 16846783.5, dated Mar. 29, 2018, 8 pages.

Gan et al., "Fermentation alters Antioxidant capacity and polyphenol distribution in selected edible legumes", International Journal of Food and Science Technology, 2016, 51:875-884.

Indian Office Action in IN Appln. No. 201817013554, dated Aug. 13, 2020, 6 pages with English Translation.

Japanese Notice of Reasons for Refusal in JP Appln. No. 20185137764, dated Mar. 27, 2019, 7 pages with English Translation.

Japanese Notice of Reasons for Refusal in JP Appln. No. 2019191700, dated Dec. 22, 2020, 8 pages with English Translation.

(56) References Cited

OTHER PUBLICATIONS

Jaspers et al., "Ecoloical Significance of Microdiversity: Identical", Applied and Environmental Microbiologo, Aug. 2004, 70(8):4831-4939.

Jhan et al., " Production of fermented red beans with multiple bioactivities using co-cultures of bacillus subtillis and lactobacillus delbrucekii subsp. Bulgaricus", LWT—Food Science and Technology, 63(2):1281-1287.

Kamitani et al., "Functional Investigation of Sweet Red Bean Pasted as an Anti-Oxidant Food: Polyphenol Contents Superoxide Dismutase Activity, and Inhibitory Effects on Reactive Oxygen Species", Journal of Japan Food Science and Technology, 2015, 62(7):349-353.

Korean Office Action in KR Appln. No. 1020160114319, dated Aug. 21, 2017, 17 pages with English Translation.

Liao et al., "Influence of preprocessing methods and fermentation of adzuki beans on y-aminobutyric acis (GABA) accumulation by lactic acid bacteria", Journal of Functional Foods, 5(3):1108-1115.

Lim et al., "*Lactobacillus johnsonii* CJLJ103 attenuates colitis and memory impairmeent in mice by inhibiting gut microbiota lipopolysaccharide production and KF-kB activation", Journal of Functional Foods, 34:359-368.

Liu et al., "Effects of *lactobacillus johnsonii* and *lactobacillus reuteri* on gut barrier function and heat shock proteins in intestinal porcine epithelial cells", Physiol. Rep. April 2015, 3(4):e12355, pp. 1-13.

NCBI, genBank Accession No. M99704.1, Sep. 7, 1993.

New Zealand Office Action in NZ Appln. No. M50202774, dated Aug. 24, 2018, 5 pages.

PCT International Preliminary Report on Patentability in International Appln. No. PCT/KR2016/009961, dated Mar. 20, 2018, 15 pages with English Translation.

PCT International Search Report in International Appln. No. PCT/KR2016/009961, dated Jan. 9, 2017, 4 pages.

Sarter et al., "Attenuation of scopolamine-induced impairment of spontaneous aalteration behavior by antagonist but not inverse agonist and agonist beta-carbolines", Psychopharmacology, 1988, 94(4):491-495.

Tannock et al., "Resource partitioning in relation to cohabitation of lactobacillus species in the mouse forestomach", The I.S.M.E. Journal, Nov. 2011, 6(5):927-938.

Wen et al., "Innate immunity and intestinal microbiota in the development of type 1 diabetes", Nature, 2008, 455:1109-1113.

\* cited by examiner

SEQUENCE LISTING

<160> NUMBER OF SEQ ID NOS: 8

<210> SEQ ID NO 1
<211> LENGTH: 1132
<212> TYPE: DNA

<213> ORGANISM: Unknown
<220> FEATURE:
<223> OTHER INFORMATION: 16S rDNA of Lactobacillus brevis CH23

<400> SEQUENCE: 1

| | | | | | |
|---|---|---|---|---|---|
| agggataaca | cttggaaaca | ggtgctaata | ccgtataaca | acaaaatccg | catggatttt | 60 |
| gtttgaaagg | tggcttcggc | tatcacttct | ggatgatccc | gcggcgtatt | agttagttgg | 120 |
| tgaggtaaag | gcccaccaag | acgatgatac | gtagccgacc | tgagagggta | atcggccaca | 180 |
| ttgggactga | gacacggccc | aaactcctac | gggaggcagc | agtagggaat | cttccacaat | 240 |
| ggacgaaagt | ctgatggagc | aatgccgcgt | gagtgaagaa | gggtttcggc | tcgtaaaact | 300 |
| ctgttgttaa | agaagaacac | ctttgagagt | aactgttcaa | gggttgacgg | tatttaacca | 360 |
| gaaagccacg | gctaactacg | tgccagcagc | cgcggtaata | cgtaggtggc | aagcgttgtc | 420 |
| cggatttatt | gggcgtaaag | cgagcgcagg | cggttttta | agtctgatgt | gaaagccttc | 480 |
| ggcttaaccg | gagaagtgca | tcggaaactg | ggagacttga | gtgcagaaga | ggacagtgga | 540 |
| actccatgtg | tagcggtgga | atgcgtagat | atatggaaga | acaccagtgg | cgaaggcggc | 600 |
| tgtctagtct | gtaactgacg | ctgaggctcg | aaagcatggg | tagcgaacag | gattagatac | 660 |
| cctgstagtc | catgccgtaa | acgatgagtg | ctaagtgttg | gagggtttcc | gcccttcagt | 720 |
| gctgcagcta | acgcattaag | cactccgcct | ggggagtacg | accgcaaggt | tgaaactcaa | 780 |
| aggaattgac | gggggcccgc | acaagcggtg | gagcatgtgt | tttaattcga | agctacgcga | 840 |
| agaaccttac | caggtcttga | catcttctgc | caatcttaga | gataagacgt | tcccttcggg | 900 |
| gacagaatga | caggtggtgc | atggttgtcg | tcagctcgtg | tcgtgagatg | ttgggttaag | 960 |
| tcccgcaacg | agcgcaaccc | ttattatcag | ttgccagcat | tcagttgggc | actctggtga | 1020 |
| gactgccggt | gacaaaccgg | aggaaggtgg | ggatgacgtc | aaatcatcat | gccccttatg | 1080 |
| acctgggcta | cacacgtgct | acaatggacg | gtacaacgag | tcgcgaagtc | gt | 1132 |

<210> SEQ ID NO 2
<211> LENGTH: 1258
<212> TYPE: DNA
<213> ORGANISM: Unknown
<220> FEATURE:
<223> OTHER INFORMATION: 16S rDNA of Lactobacillus johnsonii CH32

<400> SEQUENCE: 2

| | | | | | |
|---|---|---|---|---|---|
| gtaacttgcc | caagagactg | ggataacacc | tggaaacaga | tgctaatacc | ggataacaac | 60 |
| actagacgca | tgtctagagt | ttgaaagatg | gttctgctat | cactcttgga | tggacctgcg | 120 |
| gtgcattagc | tagttggtaa | ggtaacggct | taccaaggca | atgatgcata | gccgagttga | 180 |
| gagactgatc | ggccacattg | ggactgagac | acggcccaaa | ctcctacggg | aggcagcagt | 240 |
| agggaatctt | ccacaatgga | cgaaagtctg | atggagcaac | gccgcgtgag | tgaagaaggg | 300 |
| tttcggctcg | taaagctctg | ttggtagtga | agaaagatag | aggtagtaac | tggccttgat | 360 |
| ttgacggtaa | ttccccagaa | agtcacggct | aactacgtgc | cagcagccgc | ggtaatacgt | 420 |
| aggtggcaag | cgttgtccgg | atttattggg | cgtaaagcga | gtgcaggcgg | ttcaataagt | 480 |
| ctgatgtgaa | agccttcggc | tcaaccggag | aattgcatca | gaaactgttg | aacttgagtg | 540 |
| cagaagagga | gagtggaact | ccatgtgtag | cggtggaatg | cgtagatata | tggaagaaca | 600 |
| ccagtggcga | aggcggctct | ctggtctgca | actgacgctg | aggctcgaaa | gcatgggtag | 660 |
| cgaacaggat | tagatacccct | ggtagtccat | gccgtaaacg | atgagtgcta | agtgttggga | 720 |
| ggtttccgcc | tctcagtgct | gcagctaacg | cattaagcac | tccgcctggg | gagtacgacc | 780 |

| gcaaggttga aactcaaagg aattgacggg ggcccgcaca agcggtggag catgtggttt | 840 |
| aattcgaagc aacgcgaaga accttaccag gtcttgacat ccagtgcaaa cctaagagat | 900 |
| taggtgttcc cttcggggac gctgagacag gtggtgcatg gctgtcgtca gctcgtgtcg | 960 |
| tgagatgttg ggttaagtcc cgcaacgagc gcaacccttg tcattagttg ccatcattaa | 1020 |
| gttgggcact ctaatgagac tgccggtgac aaaccggagg aaggtgggga tgacgtcaag | 1080 |
| tcatcatgcc ccttatgacc tgggctacac acgtgctaca atggacggta caacgagaag | 1140 |
| cgaacctgcg aaggcaagcg gatctcttaa agccgttctc agttcggact gtaggctgca | 1200 |
| actcgcctac acgaagctgg aatcgctagt aatcgcggaa cagtacgccg cggtgaat | 1258 |

```
<210> SEQ ID NO 3
<211> LENGTH: 1348
<212> TYPE: DNA
<213> ORGANISM: Unknown
<220> FEATURE:
<223> OTHER INFORMATION: 16S rDNA of Bifidobacterium longum CH57

<400> SEQUENCE: 3
```

| cgggctttgc ttggtggtga gagtggcgaa cgggtgagta atgcgtgacc gacctgcccc | 60 |
| atacaccgga atagctcctg gaaacgggtg gtaatgccgg atgctccagt tgatcgcatg | 120 |
| gtcttctggg aaagctttcg cggtatggga tgggtcgcg tcctatcagc ttgacgcgg | 180 |
| ggtaacggcc caccgtggct tcgacgggta gccggcctga gagggcgacc ggccacattg | 240 |
| ggactgagat acggcccaga ctcctacggg aggcagcagt ggggaatatt gcacaatggg | 300 |
| cgcaagcctg atgcagcgac gccgcgtgag ggatggaggc cttcggggttg taaacctctt | 360 |
| ttatcgggga gcaagcgaga gtgagtttac ccgttgaata agcaccggct aactacgtgc | 420 |
| cagcagccgc ggtaatacgt agggtgcaag cgttatccgg aattattggg cgtaaagggc | 480 |
| tcgtaggcgg ttcgtcgcgt ccggtgtgaa agtccatcgc ttaacggtgg atccgcgccg | 540 |
| ggtacgggcg ggcttgagtg cggtagggga gactggaatt cccggtgtaa cggtggaatg | 600 |
| tgtagatatc gggaagaaca ccaatggcga aggcaggtct ctgggccgtt actgacgctg | 660 |
| aggagcgaaa gcgtggggag cgaacaggat tagataccct ggtagtccac gccgtaaacg | 720 |
| gtggatgctg gatgtggggc ccgttccacg ggttccgtgt cggagctaac gcgttaagca | 780 |
| tccccgcctgg gggagtacgg ccgcaaggct aaaactcaaa gaaattgacg ggggcccgca | 840 |
| caagcggcgg agcatgcgga ttaattcgat gcaacgcgaa gaaccttacc tgggcttcac | 900 |
| atgttcccga cggtcgtaga gatacggctt cccttcgggg cgggttcaca ggtggtgcat | 960 |
| ggtcgtcgtc agctcgtgtc gtgagatgtt gggttaagtc ccgcaacgag cgcaaccctc | 1020 |
| gccccgtgtt gccagcggat tatgccggga actcacgggg gaccgccggg gttaactcgg | 1080 |
| aggaaggtgg ggatgacgtc agatcatcat gccccttacg tccagggctt cacgcatgct | 1140 |
| acaatggccg gtacaacggg atgcgacgcg cgacgcgga gcggatccct gaaaaccggt | 1200 |
| ctcagttcgg atcgcagtct gcaactcgac tgcgtgaagg cggagtcgct agtaatcgcg | 1260 |
| aatcagcaac gtcgcggtga atgcgttccc gggccttgta cacaccgccc gtcaagtcat | 1320 |
| gaaagtgggc agcacccgaa gccggtgg | 1348 |

```
<210> SEQ ID NO 4
<211> LENGTH: 1421
<212> TYPE: DNA
<213> ORGANISM: Unknown
<220> FEATURE:
```

<223> OTHER INFORMATION: 16S rDNA of Lactobacillus plantarum LC5

<400> SEQUENCE: 4

| | |
|---|---|
| ctggtattga ttggtgcttg catcatgatt tacatttgag tgagtggcga actggtgagt | 60 |
| aacacgtggg aaacctgccc agaagcgggg gataacacct ggaaacagat gctaataccg | 120 |
| cataacaact tggaccgcat ggtccgagct tgaaagatgg cttcggctat cacttttgga | 180 |
| tggtcccgcg gcgtattagc tagatggtgg ggtaacggct caccatggca atgatacgta | 240 |
| gccgacctga gagggtaatc ggccacattg ggactgagac acggcccaaa ctcctacggg | 300 |
| aggcagcagt agggaatctt ccacaatgga cgaaagtctg atggagcaac gccgcgtgag | 360 |
| tgaagaaggg tttcggctcg taaaactctg ttgttaaaga agaacatatc tgagagtaac | 420 |
| tgttcaggta ttgacggtat ttaaccagaa agccacggct aactacgtgc cagcagccgc | 480 |
| ggtaatacgt aggtggcaag cgttgtccgg gatttattgg gcgtaaagcg agcgcaggcg | 540 |
| gtttttaag tctgatgtga aagccttcgg ctcaaccgaa gaagtgcatc ggaaactggg | 600 |
| aaacttgagt gcagaagagg acagtggaac tccatgtgta gcggtgaaat gcgtagatat | 660 |
| atggaagaac accagtggcg aaggcggctg tctggtctgt aactgacgct gaggctcgaa | 720 |
| agtatgggta gcaaacagga ttagataccc tggtagtcca taccgtaaac gatgaatgct | 780 |
| aagtgttgga gggtttccgc ccttcagtgc tgcagctaac gcattaagca ttccgcctgg | 840 |
| ggagtacggc cgcaaggctg aaactcaaag gaattgacgg gggcccgcac aagcggtgga | 900 |
| gcatgtggtt taattcgaag ctacgcgaag aaccttacca ggtcttgaca tactatgcaa | 960 |
| atctaagaga ttagacgttc ccttcgggga catggataca ggtggtgcat ggttgtcgtc | 1020 |
| agctcgtgtc gtgagatgtt gggttaagtc ccgcaacgag cgcaacccct attatcagtt | 1080 |
| gccagcatta agttgggcac tctggtgaga ctgccggtga caaaccggag gaaggtgggg | 1140 |
| atgacgtcaa atcatcatgc cccttatgac ctgggctaca cacgtgctac aatggatggt | 1200 |
| acaacgagtt gcgaactcgc gagagtaagc taatctctta aagccattct cagttcggat | 1260 |
| tgtaggctgc aactcgccta catgaagtcg gaatcgctag taatcgcgga tcagcatgcc | 1320 |
| gcggtgaata cgttcccggg ccttgtacac accgcccgtc acaccatgag agtttgtaac | 1380 |
| acccaaagtc ggtggggtaa ccttttagga accagccgcc t | 1421 |

<210> SEQ ID NO 5
<211> LENGTH: 1356
<212> TYPE: DNA
<213> ORGANISM: Unknown
<220> FEATURE:
<223> OTHER INFORMATION: 16S rDNA of Lactobacillus plantarum LC27

<400> SEQUENCE: 5

| | |
|---|---|
| tttacatttg attgagtggc gaactggtga gtaacacgtg gaaacctgc ccagaagcgg | 60 |
| gggataacac ctggaaacag atgctaatac cgcataacaa cttggaccgc atggtccgag | 120 |
| tttgaaagat ggcttcggct atcacttttg gatggtcccg cggcgtatta gctagatggt | 180 |
| ggggtaacgg ctcaccatgg caatgatacg tagccgacct gagagggtaa tcggccacat | 240 |
| tgggactgag acacggccca aactcctacg ggaggcagca gtagggaatc ttccacaatg | 300 |
| gacgaaagtc tgatggagca acgccgcgtg agtgaagaag ggtttcggct cgtaaaactc | 360 |
| tgttgttaaa gaagaacata tctgagagta actgttcagg tattgacggt atttaaccag | 420 |
| aaagccacgc taactacgt gccagcagcc gcggtaatac gtaggtggca agcgttgtcc | 480 |
| ggatttattg ggcgtaaagc gagcgcaggc ggtttttaa gtctgatgtg aaagccttcg | 540 |

```
gctcaaccga agaagtgcat cggaaactgg gaaacttgag tgcagaagag gacagtggaa      600
ctccatgtgt agcggtgaaa tgcgtagata tatggaagaa caccagtggc gaaggcggct      660
gtctggtctg taactgacgc tgaggctcga agtatgggt agcaaacagg attagatacc       720
ctggtagtcc ataccgtaaa cgatgaatgc taagtgttgg agggtttccg cccttcagtg      780
ctgcagctaa cgcattaagc attccgcctg gggagtacgg ccgcaaggct gaaactcaaa      840
ggaattgacg ggggcccgca caagcggtgg agcatgtggt ttaattcgaa gctacgcgaa      900
gaaccttacc aggtcttgac atactatgca atctaagag attagacgtt cccttcgggg       960
acatggatac aggtggtgca tggttgtcgt cagctcgtgt cgtgagatgt tgggttaagt     1020
cccgcaacga gcgcaaccct tattatcagt tgccagcatt aagttgggca ctctggtgag     1080
actgccggtg acaaaccgga ggaaggtggg gatgacgtca atcatcatg cccttatga        1140 cctgggctac acacgtgcta caatggatgg tacaacgagt tgcgaactcg cgagagtaag     1200
ctaatctctt aaagccattc tcagttcgga ttgtaggctg caactcgcct acatgaagtc     1260
ggaatcgcta gtaatcgcgg atcagcatgc cgcggtgaat acgttcccgg gccttgtaca     1320
caccgcccgt cacaccatga gagtttgtaa caccca                                1356

<210> SEQ ID NO 6
<211> LENGTH: 1325
<212> TYPE: DNA
<213> ORGANISM: Unknown
<220> FEATURE:
<223> OTHER INFORMATION: 16S rDNA of Lactobacillus plantarum LC28

<400> SEQUENCE: 6
catcatgatt tacatttgag tgagtggcga actggtgagt aacacgtggg aaacctgccc       60
agaagcgggg gataacacct ggaaacagat gctaataccg cataacaact tggaccgcat      120
ggtccgagtt tgaaagatgg cttcggctat cactttggga tggtcccgcg gcgtattagc      180
tagatggtgg ggtaacggct caccatggca atgatacgta gccgacctga gagggtaatc     240
ggccacattg ggactgagac acggcccaaa ctcctacggg aggcagcagt agggaatctt      300
ccacaatgga cgaaagtctg atggagcaac gccgcgtgag tgaagaaggg tttcggctcg     360
taaaactctg ttgttaaaga agaacatatc tgagagtaac tgttcaggta ttgacggtat      420
ttaaccagaa agccacggct aactacgtgc cagcagccgc ggtaatacgt aggtggcaag     480
cgttgtccgg atttattggg cgtaaagcga gcgcaggcgg ttttttaagt ctgatgtgaa      540
agccttcggc tcaaccgaag aagtgcatcg gaaactggga acttgagtg cagaagagga      600 cagtggaact ccatgtgtag cggtgaaatg cgtagatata tggaagaaca ccagtggcga      660
aggcggctgt ctggtctgta actgacgctg aggctcgaaa gtatgggtag caaacaggat     720
tagataccct ggtagtccat accgtaaacg atgaatgcta agtgttggag ggtttccgcc     780
cttcagtgct gcagctaacg cattaagcat tccgcctggg gagtacgccg caaggctga      840 aactcaaagg aattgacggg ggcccgcaca agcggtggag catgtggttt aattcgaagc     900
tacgcgaaga accttaccag gtcttgacat actatgcaaa tctaagagat tagacgttcc      960 cttcgggac atggatacag gtggtgcatg gttgtcgtca gctcgtgtcg tgagatgttg     1020
ggttaagtcc cgcaacgagc gcaaccctta ttatcagttg ccagcattaa gttgggcact     1080
ctggtgagac tgccggtgac aaaccggagg aaggtgggga tgacgtcaaa tcatcatgcc     1140
ccttatgacc tgggctacac acgtgctaca atggatggta caacgagttg cgaactcgcg     1200
```

```
agagtaagct aatctcttaa agccattctc agttcggatt gtaggctgca actcgcctac    1260
atgaagtcgg aatcgctagt aatcgcggat cagcattccg cggtgaatac gttcccgggc    1320
cttgt                                                                1325

<210> SEQ ID NO 7
<211> LENGTH: 1342
<212> TYPE: DNA
<213> ORGANISM: Unknown
<220> FEATURE:
<223> OTHER INFORMATION: 16S rDNA of Bifidobacterium longum LC67

<400> SEQUENCE: 7
ggctttgctt ggtggtgaga gtggcgaacg ggtgagtaat gcgtgaccga cctgccccat      60
acaccggaat agctcctgga aacgggtggt aatgccggat gctccagttg atcgcatggt     120
cttctgggaa agctttcgcg gtatgggatg gggtcgcgtc ctatcagctt gacggcgggg     180
taacggccca ccgtggcttc gacgggtagc cggcctgaga gggcgaccgg ccacattggg     240
actgagatac ggcccagact cctacgggag gcagcagtgg ggaatattgc acaatgggcg     300
caagcctgat gcagcgacgc cgcgtgaggg atggaggcct cgggttgta aacctctttt      360 atcggggagc aagcgagagt gagtttaccc gttgaataag caccggctaa ctacgtgcca     420
gcagccgcgg taatacgtag ggtgcaagcg ttatcccgga attattgggc gtaagggct      480 cgtaggcggt tcgtcgcgtc cggtgtgaaa gtccatcgct taacggtgga tccgcgccgg     540
gtacgggcgg gcttgagtgc ggtaggggag actggaattc ccggtgtaac ggtggaatgt     600
gtagatatcg ggaagaacac caatggcgaa ggcaggtctc tgggccgtta ctgacgctga     660
ggagcgaaag cgtggggagc gaacaggatt agataccctg gtagtccacg ccgtaaacgg     720
tggatgctgg atgtggggcc cgttccacgg gttccgtgtc ggagctaacg cgttaagcat     780
cccgcctggg ggagtacggc cgcaaggcta aaactcaaag aaattgacgg gggcccgcac     840
aagcggcgga gcatgcggat taattcgatg caacgcgaag aaccttacct gggcttgaca     900
tgttcccgac ggtcgtagag atacggcttc ccttcggggc gggttcacag gtggtgcatg     960
gtcgtcgtca gctcgtgtcg tgagatgttg ggttaagtcc cgcaacgagc gcaaccctcg    1020
ccccgtgttg ccagcggatt atgccgggaa ctcacggggg accgccgggg ttaactcgga    1080
ggaaggtggg gatgacgtca gatcatcatg ccccttacgt ccagggcttc acgcatgcta    1140
caatggccgg tacaacggga tgcgacgcgg cgacgcggag cggatccctg aaaaccggtc    1200
tcagttcgga tcgcagtctg caactcgact gcgtgaaggc ggagtcgcta gtaatcgcga    1260
atcagcaacg tcgcggtgaa tgcgttcccg ggccttgtac acaccgcccg tcaagtcatg    1320
aaagtgggca gcacccgaag cg                                             1342

<210> SEQ ID NO 8
<211> LENGTH: 1343
<212> TYPE: DNA
<213> ORGANISM: Unknown
<220> FEATURE:
<223> OTHER INFORMATION: 16S rDNA of Bifidobacterium longum LC68

<400> SEQUENCE: 8
cggcttcggg tgctgcccac tttcatgact tgacgggcgg tgtgtacaag gcccgggaac      60
gcattcaccg cgacgttgct gattcgcgat tactagcgac tccgccttca cgcagtcgag     120
ttgcagactg cgatccgaac tgagaccggt tttcagggat ccgctccgcg tcgccgcgtc     180
gcatcccgtt gtaccggcca ttgtagcatg cgtgaagccc tggacgtaag gggcatgatg     240
```

```
atctgacgtc atcccacct tcctccgagt taacccggc ggtccccgt gagttcccgg      300 cataatccgc tggcaacacg gggcgagggt tgcgctcgtt gcgggactta acccaacatc   360
tcacgacacg agctgacgac gaccatgcac cacctgtgaa cccgcccga agggaagccg    420 catctctacg accgtcggga acatgtcaag cccaggtaag gttcttcgcg ttgcatcgaa   480
ttaatccgca tgctccgccg cttgtgcggg ccccgtcaa tttctttgag ttttagcctt    540
gcggccgtac tccccaggcg ggatgcttaa cgcgttagct ccgacacgga acccgtggaa   600
cgggccccac atccagcatc caccgtttac ggcgtggact accagggtat ctaatcctgt   660
tcgctcccca cgctttcgct cctcagcgtc agtaacggcc cagagacctg ccttcgccat   720
tggtgttctt cccgatatct acacattcca ccgttacacc gggaattcca gtctcccta    780 ccgcactcaa gcccgcccgt accggcgcg gatccaccgt taagcgatgg actttcacac    840
cggacgcgac gaaccgccta cgagcccttt acgcccaata attccggata acgcttgcac   900
cctacgtatt accgcggctg ctggcacgta gttagccggt gcttattcaa cgggtaaact   960
cactctcgct tgctccccga taaagaggt ttacaacccg aaggcctcca tccctcacgc   1020
ggcgtcgctg catcaggctt gcgcccattg tgcaatattc cccactgctg cctcccgtag   1080
gagtctgggc cgtatctcag tcccaatgtg gccggtcgcc ctctcaggcc ggctacccgt   1140
cgaagccacg gtgggccgtt accccgccgt caagctgata ggacgcgacc ccatcccata   1200
ccgcgaaagc tttcccagaa gaccatgcga tcaactggag catccggcat taccacccgt   1260
ttccaggagc tattccggtg tatggggcag gtcggtcacg cattactcac ccgttcgcca   1320
ctctcaccac caagcaaagt ctc                                           1343
```

LACTOBACILLUS HAVING VARIOUS FUNCTIONS, AND USE THEREOF

SEQUENCE LISTING

The instant application contains a Sequence Listing which has been submitted electronically in ASCII format and is hereby incorporated by reference in its entirety. Said ASCII copy, created on Jun. 13, 2018, is named 46533-0003US1.txt and is 15,850 bytes in size.

TECHNICAL FIELD

The present invention relates to novel lactic acid bacteria and the like, and more particularly to novel lactic acid bacteria or novel lactic acid bacteria mixtures, which are isolated from kimchi or human feces and have various physiological activities such as antioxidant activity, β-glucuronidase-inhibitory activity, lipopolysaccharide (LPS) production-inhibitory activity or tight junction protein expression-inducing activity. Moreover, the present invention relates to various food and medicinal uses of novel lactic acid bacteria or novel lactic acid bacteria mixtures.

BACKGROUND ART

As humanity has developed into a prosperous society, the fast food has been rapidly become popular and the pattern of diseases has also changed dramatically. In particular, in modern people, intestinal flora disturbance, intestinal permeability syndrome, colitis, liver diseases, allergic diseases, obesity and the like are increasing due to fast food eating habits based on meat and fat, irregular meal, excessive drinking, lack of exercise, excessive stress, exposure to harmful environments, and the like.

Intestinal Flora Disturbance

There are many bacteria living in the gastrointestinal tract of the human body. The human body has about 10 trillion normal cells, but has about 100 trillion bacteria which are about 10-fold larger than the normal cells. These bacteria can be divided into beneficial bacteria that help human intestinal health and harmful bacteria that are harmful to human health. The health of human body can be maintained when beneficial bacterial such as *Lactobacillus, Bifidobacterium, Streptococcus, Leuconostoc, Pediococcus, Sporolactobacillius* and the like are more dominant in the gastrointestinal tract than harmful bacteria. Otherwise, diseases can be caused, such as obesity, intestinal permeability syndrome, liver diseases, accelerated aging, enteritis and the like.

Intestinal Permeability Syndrome

The gastrointestinal tract of the human body is composed of mucus and villi, which efficiently absorb nutrient components, but prevent the absorption of pathogenic microorganisms having a high molecular weight or toxins produced by these microorganisms. In addition, the human body has an immune system capable of protecting the body from invasion of external antigens having a high molecular weight. However, due to infection with many pathogenic microorganisms or toxins, excessive stress, intake of foods such as high-fat diets capable of proliferating harmful bacterial living in the gastrointestinal tract, excessive alcohol intake, the abuse of drugs (e.g., antibiotics) and the like, intestinal flora is disturbed, abnormalities in the gastrointestinal tract's immune system occur, and expression of tight junction proteins is inhibited. If expression of tight junction proteins is inhibited, tight junction of intestinal mucosa becomes loosened, and the invasion into the body of large molecules due to the loosened gap and abnormalities in the immune system.

Intestinal permeability syndrome is also known as leaky gut syndrome, and refers to a condition in which external such as less digested foods, pathogenic microorganisms, toxins or the like are continuously introduced into blood, because the tight junction barrier system of epithelial cells forming the gastrointestinal tract is not smoothly operated. When intestinal permeability syndrome occurs, external antigens that are generally not absorbed into the body enter the body, thus causing ulcerative colitis, Crohn's disease, liver injury, liver dysfunction, allergic diseases (including asthma), atopy, autoimmune diseases, steatorrhea, digestive absorption disorder, acne, accelerated aging, endotoxemia, intestinal infection, eczema, irritable bowel syndrome, chronic fatigue syndrome, psoriasis, rheumatoid arthritis, pancreatic insufficiency, inflammatory joint diseases or the like.

Colitis

Although it was previously known that the incidence of ulcerative colitis and Crohn's disease is high in Europeans, the number of patients with ulcerative colitis and Crohn's disease in oriental countries including Korea has recently increased rapidly due to changes in lifestyles such as eating habits. However, the cause is unclear, and thus a fundamental treatment method for these diseases has not yet been established. For this reason, drugs are used which do not aim to completely treat, but aim to relieve symptoms and maintain this relieved state over the longest possible period. As drugs for this symptomatic therapy, aminosalicylic acid agents, adrenocorticosteroid agents, immunosuppressants and the like are mainly used, but have been reported to cause various side effects. For example, sulfasalazine which is frequently used as an aminosalicylic acid agent was reported to cause side effects, including nausea, vomiting, anorexia, rash, headache, liver injury, leukocytopenia, abnormal red blood cells, proteinuria, diarrhea and the like. In addition, adrenocorticosteroid agents are generally used by prednisolone oral administration, infusion, suppository, intravenous injection or the like, but cause strong side effects such as gastric ulcer or femoral necrosis upon long-term use. However, discontinuation of medication can cause symptoms to recur, and thus these drugs must be continuously used. Accordingly, there is a need to develop agents for treating intestinal bowel diseases, such as ulcerative colitis, Crohn's diseases and the like, which have excellent effects, are safe and cause no side effects. Irritable bowel syndrome (IBS) is also a chronic abdominal disease whose cause is unclear. Currently, there is no fundamental therapeutic agent for IBS, and symptomatic therapy is performed for the purpose of relieving symptoms of each type of IBS. For example, for diarrhea-IBS, an anticholinergic agent having spasmolytic action that suppresses the contraction of smooth muscles is used, and for constipation-IBS, salt laxatives are used. For alternating-IBS difficult to control with drugs, an agent for improving gastrointestinal motor function is fundamentally used.

Liver Diseases

The liver in the human body plays roles such as energy metabolism (nutrient treatment and storage, and waste excretion), detoxification of toxins, synthesis of serum proteins, and smooth absorption of fat in the bowel by bile juice secretion, and is also important in immunity maintenance (body defense) and vitamin metabolism. However, infection with hepatitis viruses or excessive intake of alcohol or high-fat meals may cause liver diseases such as hepatitis, fatty liver or liver cirrhosis. In addition, liver diseases may also be caused by drugs (tuberculosis therapeutic drugs, aspirin, antibiotics, anesthetics, antihypertensive drugs, oral contraceptives, etc.), congenital metabolic disorders, heart failure, shock, or the like. When liver disease occurs, it can develop into chronic hepatitis, starting with acute hepatitis with fatigue, vomiting, diarrhea, anorexia, jaundice, right upper quadrant pain, fever or muscle pain.

Allergic Diseases

As society has become more complicated and the industry and civilization has developed, environmental pollution and stress have increased, and as eating habits have changed, patients with allergic diseases have increased every year. Patients with allergic diseases such as atopy, anaxylosis, asthma and the like were less than 1% in 1980, but increased rapidly to 5% or more in 2000s, and are estimated to be more than 10%, including potential patients. Allergic diseases are caused by excessive immune responses of a body, which result from antigen-antibody reactions, and allergic diseases are classified into types 1 to 4 hypersensitivity reactions based on response time and whether complements are involved. Type 1 hypersensitivity reactions include atopy, anaphylactic shock, bronchial asthma, urticaria, pollinosis and the like; type 2 hypersensitivity reactions include inadequate transfusion, autoimmune hemolytic anemia, hemolytic anemia caused by drugs, granulocytopenia, thrombocytopenic purpura and the like; type 3 hypersensitivity reactions include erythema, lymphatic swelling, arthralgia, arthritis, nephritis, acute glomerulonephritis following streptococcal infection, and the like; and type 4 hypersensitivity reactions include chronic inflammation and the like. To improve allergic diseases, it is preferable to remove allergens (house dust, mites, etc.) from the skin by showering or bathing and avoid allergen intake. However, when allergic diseases are not improved, drugs such as steroids, antihistamines, immunosuppressants or the like are used, which easily cause side effects such as skin atrophy, vasodilation, discoloration, purpura (steroids), drowsiness (antihistamines), kidney failure (immunosuppressants) and the like. Among the drugs developed so far, there is no drug that can completely cure allergies, and these drugs are expected to improve symptoms, but have the problem of causing significant side effects.

Obesity

Obesity is a metabolic disorder caused by the imbalance of calorie intake and consumption, and is caused by the increased size (hypertrophy) or increased number (hyperplasia) of in vivo adipocytes in morphological terms. Obesity is not only the most common malnutrition disorder in western society, and the prevalence of obesity in Korea is also rapidly increasing due to the improvement of eating habits and westernization of lifestyles. Therefore, the importance of treatment and prevention of obesity has been greatly emphasized. Obesity is an important factor that disturbs the individual in psychological terms and also increases the risk of various adult diseases in social terms. Obesity is known to be directly related to the increased prevalence of various adult diseases such as type 2 diabetes, hypertension, hyperlipidemia, heart disease and the like (Cell 87:377, 1999), and diseases related to obesity are collectively referred to as metabolic syndrome or insulin resistance syndrome, and these diseases have been reported to cause arteriosclerosis and cardiovascular diseases. Obesity therapeutic agents known so far Xenical (Roche Pharmaceuticals, Switzerland), Reductil (Abbott, USA), Exolise (Arkopharma, France) and the like, and are largely classified into appetite suppressants, energy expenditure promoters, and fat absorption inhibitors. Most obesity therapeutic agents are appetite suppressants that suppress appetite by controlling the neurotransmitters associated with the hypothalamus. However, conventional therapeutic agents cause side effects such as heart diseases, respiratory diseases, neurological diseases and the like, and the persistence of their effects is also low. Thus, the development of improved obesity therapeutic agents is required. In addition, among currently developed products, there are little or no therapeutic agents that have satisfactory therapeutic effect without causing side effects, and thus the development of a new therapeutic agent for obesity is required.

Probiotics are collectively referred to as live microorganisms that improve the host's microbial environment in the gastrointestinal tract of animals, including humans, and have beneficial effects on the host's health. In order to be effective as probiotics, it is necessary to have excellent acid resistance, bile resistance and adherence to epithelial cells, because most of these probiotics should reach the small intestine upon oral administration and must be adhered to the intestinal surface. Lactic acid bacteria are used as probiotics because they play a role in decomposing fibrous and complex proteins to make important nutrients while living in the digestive system of the human body. Lactic acid bacteria have been reported to exhibit effects such as maintenance of intestinal normal flora, improvement of intestinal flora, anti-diabetic and anti-hyperlipidemic effects, inhibition of carcinogenesis, inhibition of colitis, and nonspecific activity of the host's immune system. Among these lactic acid bacteria, *Lactobacillus* sp. strains are major members of normal microbial communities living in the bowel of the human body and have long been known to be important in maintaining a healthy digestive tract and vaginal environment. Currently, according to the U.S. Public Health Service guidelines, all the *Lactobacillus* strains deposited with the American Type Culture Collection (ATCC) are classified as 'Bio-Safety Level 1', which is recognized as having no known potential risk of causing disease in humans or animals. Meanwhile, lactic acid bacteria of kimchi that are involved in kimchi fermentation have been reported to have immune enhancement effects, antimicrobial effects, antioxidant effects, anti-cancer effects, anti-obesity effects, hypertension preventive effects or constipation preventive effects [Hivak P, Odrska J, Ferencik M, Ebringer L, Jahnova E, Mikes Z. One-year application of Probiotic strain *Enterococcus facium* M-74 decreases Serum cholesterol levels. Bratisl lek Listy 2005; 106(2); 67-72; Agerholm-Larsen L. Bell M L. Grunwald G K. Astrup A.: The effect of a probiotic milk product on plasma cholesterol: a metaanalysis of short-term intervention studies; Eur J Clin Nutr. 2000; 54(11) 856-860; Renato Sousa, Jaroslava Helper, Jian Zhang, Strephen J Lewis and Wani O Li; Effect of *Lactobacillus acidophilus* supernants on body weight and leptin expression in rats; BMC complementary and alternative medicine. 2008; 8(5)1-8].

Since various bioactive activities of lactic acid bacteria were known, studies have recently been conducted to develop lactic acid bacterial strains that have excellent functions while being safe for the human and to apply these strains to medicines or functional foods. For example, Korean Patent Application Publication No. 10-2009-0116051 discloses *Lactobacillus brevis* HY7401 having the effects of treating and preventing colitis. Furthermore, Korean Patent Application Publication No. 10-2006-0119045 discloses lactic acid bacteria for preventing or treating atopic dermatitis, which is selected from the group consisting of *Leuconostoc citreum* KACC91035, *Leuconos-*

*toc mesenteroides* subsp. *mesenteroides* KCTC 3100 and *Lactobacillus brevis* KCTC 3498. Furthermore, Korean Patent Application Publication No. 10-2013-0092182 discloses a functional health food for preventing alcoholic liver disease or relieving hangovers, which comprises *Lactobacillus brevis* HD-01 (accession number: KACC91701P) having an excellent ability to decompose alcohol. In addition, Korean Patent Application Publication No. 10-2010-0010015 discloses a *Lactobacillus johnsonii* HFI 108 strain (KCTC 11356BP) having blood cholesterol lowering and anti-obesity activities. In addition, Korean Patent Application Publication No. 10-2014-0006509 discloses a composition for preventing or treating obesity comprising a *Bifidobacterium longum* CGB-C11 strain (accession number: KCTC 11979BP) that produces conjugated linoleic acid as an active ingredient.

However, there has been no report of lactic acid bacteria-related technology capable of alleviating or treating all of intestinal flora disturbance, intestinal permeability syndrome, colitis, liver diseases, allergic diseases, obesity and the like, which are increasing in modern humans. Therefore, there is a need to screen a novel strain having various functionalities and to develop medicines, functional foods and the like by use of this strain.

DISCLOSURE

Technical Problem

The present invention has been made under the Background Art as described above, and it is an object of the present invention to provide novel lactic acid bacteria having various physiological activities or functionalities required for probiotics, and the food and medicinal uses thereof.

Another object of the present invention is to provide a novel lactic acid bacteria mixture capable of exhibiting various maximized physiological activities or functionalities, and the food and medicinal uses thereof.

Technical Solution

The present inventors have screened numerous lactic acid bacteria from kimchi or human feces, and have found that, among these screened lactic acid bacteria, a certain *Lactobacillus* sp. strain, a certain *Bifidobacterium* sp. strain or a mixture thereof has an excellent effect on the improvement of intestinal damage such as intestinal permeability syndrome, liver injury such as fatty liver, allergic diseases such as atopic dermatitis, inflammatory diseases such colitis, or obesity, thereby completing the present invention.

To achieve the above objects, an embodiment of the present invention provides a lactic acid bacteria selected from *Lactobacillus brevis* comprising a 16S rDNA nucleotide sequence represented by SEQ ID NO: 1, *Bifidobacterium longum* comprising a 16S rDNA nucleotide sequence represented by SEQ ID NO: 3, *Lactobacillus plantarum* comprising a 16S rDNA nucleotide sequence represented by SEQ ID NO: 4, *Lactobacillus plantarum* comprising a 16S rDNA nucleotide sequence represented by SEQ ID NO: 5 or *Bifidobacterium longum* comprising a 16S rDNA nucleotide sequence represented by SEQ ID NO: 7. The *Lactobacillus brevis*, *Lactobacillus plantarum* or *Bifidobacterium longum* has antioxidant activity, β-glucuronidase-inhibitory activity, lipopolysaccharide (LPS) production-inhibitory activity or tight junction protein expression-inducing activity. Another embodiment of the present invention provides a pharmaceutical composition for preventing or treating intestinal damage, liver injury, allergic disease, inflammatory disease or obesity comprising lactic acid bacteria selected from *Lactobacillus brevis* comprising a 16S rDNA nucleotide sequence represented by SEQ ID NO: 1, *Bifidobacterium longum* comprising a 16S rDNA nucleotide sequence represented by SEQ ID NO: 3, *Lactobacillus plantarum* comprising a 16S rDNA nucleotide sequence represented by SEQ ID NO: 4, *Lactobacillus plantarum* comprising a 16S rDNA nucleotide sequence represented by SEQ ID NO: 5 or *Bifidobacterium longum* comprising a 16S rDNA nucleotide sequence represented by SEQ ID NO: 7, a culture of the lactic acid bacteria, a lysate of the lactic acid bacteria or an extract of the lactic acid bacteria as an active ingredient. Still another embodiment of the present invention provides a food composition for preventing or alleviating intestinal damage, liver injury, allergic disease, inflammatory disease or obesity comprising *Lactobacillus brevis* comprising a 16S rDNA nucleotide sequence represented by SEQ ID NO: 1, *Bifidobacterium longum* comprising a 16S rDNA nucleotide sequence represented by SEQ ID NO: 3, *Lactobacillus plantarum* comprising a 16S rDNA nucleotide sequence represented by SEQ ID NO: 4, *Lactobacillus plantarum* comprising a 16S rDNA nucleotide sequence represented by SEQ ID NO: 5 or *Bifidobacterium longum* comprising a 16S rDNA nucleotide sequence represented by SEQ ID NO: 7, a culture of the lactic acid bacteria, a lysate of the lactic acid bacteria or an extract of the lactic acid bacteria as an active ingredient.

To achieve other objects of the present invention, an embodiment of the present invention provides a mixture of two or more lactic acid bacteria selected from the group consisting of *Lactobacillus brevis* comprising a 16S rDNA nucleotide sequence represented by SEQ ID NO: 1, *Bifidobacterium longum* comprising a 16S rDNA nucleotide sequence represented by SEQ ID NO: 3, *Lactobacillus plantarum* comprising a 16S rDNA nucleotide sequence represented by SEQ ID NO: 4, *Lactobacillus plantarum* comprising a 16S rDNA nucleotide sequence represented by SEQ ID NO: 5, and *Bifidobacterium longum* comprising a 16S rDNA nucleotide sequence represented by SEQ ID NO: 7. The mixture of lactic acid bacteria has antioxidant activity, β-glucuronidase-inhibitory activity, lipopolysaccharide (LPS) production-inhibitory activity or tight junction protein expression-inducing activity. Another embodiment of the present invention provides a composition for preventing or treating intestinal damage, liver injury, allergic disease, inflammatory disease or obesity comprising a mixture of two or more lactic acid bacteria selected from the group consisting of *Lactobacillus brevis* comprising a 16S rDNA nucleotide sequence represented by SEQ ID NO: 1, *Bifidobacterium longum* comprising a 16S rDNA nucleotide sequence represented by SEQ ID NO: 3, *Lactobacillus plantarum* comprising a 16S rDNA nucleotide sequence represented by SEQ ID NO: 4, *Lactobacillus plantarum* comprising a 16S rDNA nucleotide sequence represented by SEQ ID NO: 5 and *Bifidobacterium longum* comprising a 16S rDNA nucleotide sequence represented by SEQ ID NO: 7, a culture of the mixture of lactic acid bacteria, a lysate of the mixture of lactic acid bacteria or an extract of the mixture of lactic acid bacteria as an active ingredient. Still another embodiment of the present invention provides a food composition for preventing or alleviating intestinal damage, liver injury, allergic disease, inflammatory disease or obesity comprising a mixture of two or more lactic acid bacteria selected from the group consisting of *Lactobacillus brevis* comprising a 16S rDNA nucleotide sequence represented by SEQ ID NO: 1, *Bifidobacterium longum* comprising a 16S rDNA nucleotide sequence represented by SEQ ID NO: 3, *Lactobacillus plantarum* comprising a 16S rDNA nucleotide sequence represented by SEQ ID NO: 4, *Lactobacillus plantarum* comprising a 16S rDNA nucleotide sequence represented by SEQ ID NO: 5 and *Bifidobacterium longum* comprising a 16S rDNA nucleotide sequence represented by SEQ ID NO: 7, a culture of the mixture of lactic acid bacteria, a lysate of the mixture of lactic acid bacteria, or an extract of the mixture of lactic acid bacteria as an active ingredient.

Advantageous Effects

A certain *Lactobacillus* sp. strain or certain *Bifidobacterium* sp. strain according to the present invention is isolated from kimchi or human feces, and thus is highly safe, and has various physiological activities such as antioxidant activity, β-glucuronidase-inhibitory activity, lipopolysaccharide (LPS) production-inhibitory activity or tight junction protein expression-inducing activity. Accordingly, a certain *Lactobacillus* sp. strain, certain *Bifidobacterium* sp. strain or mixture thereof according to the present invention may be used as a functional food or medicinal material useful for preventing, alleviating or treating of intestinal damage, liver injury, allergic disease, inflammatory disease or obesity.

MODE FOR INVENTION

Figure 1:
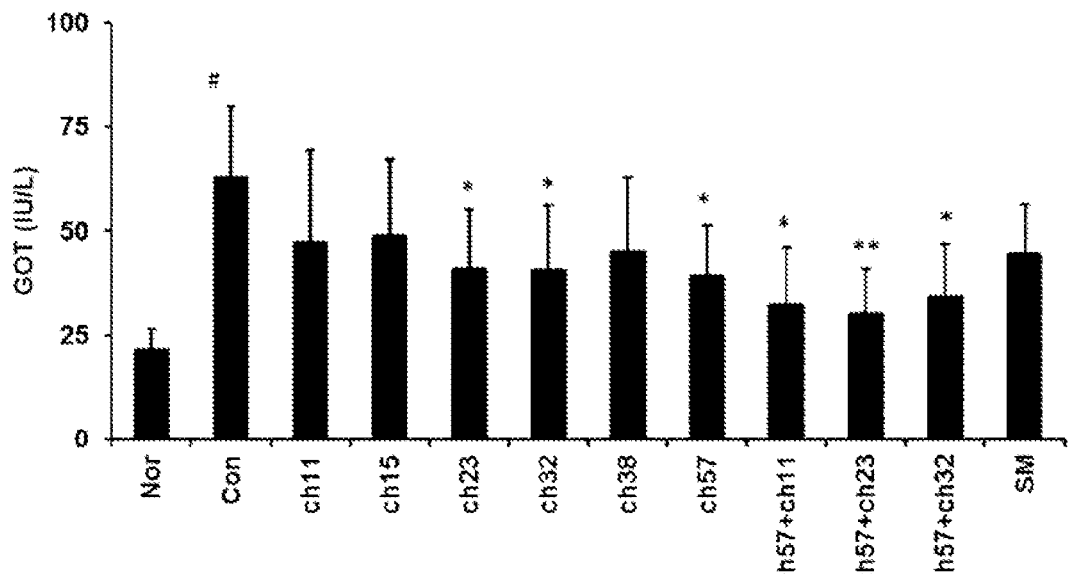
FIG. 1 is a graph showing the change in GOT value when lactic acid bacteria were administered to model animals having liver injury induced by D-galactosamine, in a first experiment of the present invention.

As used herein, terms used in the present invention will be defined.

As used herein, the term "culture" means a product obtained by culturing a microorganism in a known liquid medium or solid medium, and thus is intended to include a microorganism.

As used herein, the terms "pharmaceutically acceptable" and "sitologically acceptable" means neither significantly stimulating an organism nor inhibiting the biological activity and characteristics of an active material administered.

As used herein, the term "preventing" refers to all actions that inhibit symptoms or delay the progression of a particular disease by administrating the composition of the present invention.

As used herein, the term "treating" refers to all actions that alleviate or beneficially change the symptoms of a particular disease by administering the composition of the present invention.

As used herein, the term "alleviating" refers to all actions that at least reduce a parameter related to the condition to be treated, for example, the degree of symptom.

As used herein, the term "administering" means providing the composition of the present invention to a subject by any suitable method. As used herein, the term "subject" means all animals, including humans, monkeys, dogs, goats, pigs or rats, which have a particular disease whose symptoms can be alleviated by administering the composition of the present invention.

As used herein, the term "pharmaceutically effective amount" refers to an amount sufficient to treat diseases, at a reasonable benefit/risk ratio applicable to any medical treatment. The pharmaceutically effective amount may be determined depending on factors including the kind of subject's disease, the severity of the disease, the activity of the drug, sensitivity to the drug, the time of administration, the route of administration, excretion rate, the duration of treatment and drugs used in combination with the composition, and other factors known in the medical field.

Hereinafter, the present invention will be described in detail.

One aspect of the present invention is related to novel lactic acid bacteria having various physiological activities or to novel lactic acid bacteria mixture which may have increased physiological activities.

A novel lactic acid bacteria according to one embodiment of the present invention is selected from *Lactobacillus brevis* comprising a 16S rDNA nucleotide sequence represented by SEQ ID NO: 1, *Bifidobacterium longum* comprising a 16S rDNA nucleotide sequence represented by SEQ ID NO: 3, *Lactobacillus plantarum* comprising a 16S rDNA nucleotide sequence represented by SEQ ID NO: 4, *Lactobacillus plantarum* comprising a 16S rDNA nucleotide sequence represented by SEQ ID NO: 5 or *Bifidobacterium longum* comprising a 16S rDNA nucleotide sequence represented by SEQ ID NO: 7, and has antioxidant activity, β-glucuronidase inhibitory activity, lipopolysaccharide (LPS) production inhibitory activity or tight junction protein expression-inducing activity.

The *Lactobacillus brevis* comprising the 16S rDNA nucleotide sequence represented by SEQ ID NO: 1 is an anaerobic *bacillus* isolated from kimchi, is positive to gram staining, can survive in a wide temperature range, low pHs and high salt concentrations, and produces glucosidase. Furthermore, the *Lactobacillus brevis* comprising the 16S rDNA nucleotide sequence represented by SEQ ID NO: 1 utilizes D-ribose, D-xylose, D-glucose, D-fructose, esculin, salicin, maltose, melibiose, 5-keto-gluconate and the like as carbon sources. In addition, the *Lactobacillus brevis* comprising the 16S rDNA nucleotide sequence represented by SEQ ID NO: 1 is preferably *Lactobacillus brevis* CH23 (accession number: KCCM 11762P). The *Bifidobacterium longum* comprising the 16S rDNA nucleotide sequence represented by SEQ ID NO: 3 is an anaerobic *bacillus* isolated from human feces, is positive to gram staining, and produces glucosidase. Furthermore, the *Bifidobacterium longum* comprising the 16S rDNA nucleotide sequence represented by SEQ ID NO: 3 utilizes D-galactose, D-glucose, D-fructose and the like as carbon sources. In addition, the *Bifidobacterium longum* comprising the 16S rDNA nucleotide sequence represented by SEQ ID NO: 3 is preferably *Bifidobacterium longum* CH57 (accession number: KCCM 11764P). The *Lactobacillus plantarum* comprising the 16S rDNA nucleotide sequence represented by SEQ ID NO: 4 is an anaerobic *bacillus* isolated from kimchi and is positive to gram staining. Furthermore, the *Lactobacillus plantarum* comprising the 16S rDNA nucleotide sequence represented by SEQ ID NO: 4 utilizes D-ribose, D-galactose, D-glucose, D-fructose, D-mannose, mannitol, sorbitol, N-acetyl-glucosamine, amygdalin, arbutin, esculin, salicin, cellobiose, maltose, melibiose, sucrose, trehalose, melezitose and the like as carbon sources. In addition, the *Lactobacillus plantarum* comprising the 16S rDNA nucleotide sequence represented by SEQ ID NO: 4 is preferably *Lactobacillus plantarum* LC5 (accession number: KCCM 11800P). The *Lactobacillus plantarum* comprising the 16S rDNA nucleotide sequence represented by SEQ ID NO: 5 is an anaerobic *bacillus* isolated from kimchi, and is positive to gram staining. Furthermore, the *Lactobacillus plantarum* comprising the 16S rDNA nucleotide sequence represented by SEQ ID NO: 5 utilizes L-arabinose, D-ribose, D-glucose, D-fructose, D-mannose, mannitol, sorbitol, N-acetyl-glucosamine, amygdalin, arbutin, esculin, salicin, cellobiose, maltose, lactose, melibiose, sucrose, trehalose, melezitose and the like as carbon sources. In addition, the *Lactobacillus plantarum* comprising the 16S rDNA nucleotide sequence represented by SEQ ID NO: 5 is preferably *Lactobacillus plantarum* LC27 (accession number: KCCM 11801P). The *Bifidobacterium longum* comprising the 16S rDNA nucleotide sequence represented by SEQ ID NO: 7 is an anaerobic *bacillus* isolated from human feces, and is positive to gram staining. Furthermore, the *Bifidobacterium longum* comprising the 16S rDNA nucleotide sequence represented by SEQ ID NO: 7 utilizes L-arabinose, D-xylose, D-glucose, D-fructose, esculin, maltose, lactose, melibiose, sucrose and the like as carbon sources. In addition, the *Bifidobacterium longum* comprising the 16S rDNA nucleotide sequence represented by SEQ ID NO: 7 is preferably *Bifidobacterium longum* LC67 (accession number: KCCM 11802P).

A mixture of lactic acid bacteria according to an embodiment of the present invention is a mixture of two or more lactic acid bacteria selected from *Lactobacillus brevis* comprising a 16S rDNA nucleotide sequence represented by SEQ ID NO: 1, *Bifidobacterium longum* comprising a 16S rDNA nucleotide sequence represented by SEQ ID NO: 3, *Lactobacillus plantarum* comprising a 16S rDNA nucleotide sequence represented by SEQ ID NO: 4, *Lactobacillus plantarum* comprising a 16S rDNA nucleotide sequence represented by SEQ ID NO: 5 and *Bifidobacterium longum* comprising a 16S rDNA nucleotide sequence represented by SEQ ID NO: 7. In view of the synergistic effect of lactic acid bacteria, the mixture of lactic acid bacteria according to the embodiment of the present invention is preferably a combination of *Lactobacillus brevis* comprising a 16S rDNA nucleotide sequence represented by SEQ ID NO: 1 and *Bifidobacterium longum* comprising a 16S rDNA nucleotide sequence represented by SEQ ID NO: 3. In addition, in view of the synergistic effect of lactic acid bacteria, the mixture of lactic acid bacteria according to the embodiment of the present invention is preferably a combination of one or more *Lactobacillus* sp. selected from *Lactobacillus plantarum* comprising a 16S rDNA nucleotide sequence represented by SEQ ID NO: 4 or *Lactobacillus plantarum* comprising a 16S rDNA nucleotide sequence represented by SEQ ID NO: 5; and *Bifidobacterium longum* comprising a 16S rDNA nucleotide sequence represented by SEQ ID NO: 7. The mixture of lactic acid bacteria has higher antioxidant activity, β-glucuronidase inhibitory activity, lipopolysaccharide (LPS) production inhibitory activity or tight junction protein expression-inducing activity than a single lactic acid bacteria due to the synergistic effect of a specific *Lactobacillus* sp. strain and a specific *Bifidobacterium* sp. strain, and is more advantageous in terms of functional food and medicinal materials. In the mixture of lactic acid bacteria according to the embodiment of the present invention, the *Lactobacillus brevis* comprising the 16S rDNA nucleotide sequence represented by SEQ ID NO: 1 is preferably *Lactobacillus brevis* CH23 (accession number: KCCM 11762P); the *Bifidobacterium longum* comprising the 16S rDNA nucleotide sequence represented by SEQ ID NO: 3 is preferably *Bifidobacterium longum* CH57 (accession number: KCCM 11764P); the *Lactobacillus plantarum* comprising the 16S rDNA nucleotide sequence represented by SEQ ID NO: 4 is preferably *Lactobacillus plantarum* LC5 (accession number: KCCM 11800P); the *Lactobacillus plantarum* comprising the 16S rDNA nucleotide sequence represented by SEQ ID NO: 5 is preferably *Lactobacillus plantarum* LC27 (accession number: KCCM 11801P); and the *Bifidobacterium longum* comprising the 16S rDNA nucleotide sequence represented by SEQ ID NO: 7 is preferably *Bifidobacterium longum* LC67 (accession number: KCCM 11802P).

Another aspect of the present invention is related to various uses of the novel lactic acid bacteria or the novel lactic acid bacteria mixture. As the use of the novel lactic acid bacteria, the present invention provides a composition for preventing, alleviating or treating intestinal damage, liver injury, allergic disease, inflammatory disease or obesity comprising a lactic acid bacteria from *Lactobacillus brevis* comprising a 16S rDNA nucleotide sequence represented by SEQ ID NO: 1, *Bifidobacterium longum* comprising a 16S rDNA nucleotide sequence represented by SEQ ID NO: 3, *Lactobacillus plantarum* comprising a 16S rDNA nucleotide sequence represented by SEQ ID NO: 4, *Lactobacillus plantarum* comprising a 16S rDNA nucleotide sequence represented by SEQ ID NO: 5 or *Bifidobacterium longum* comprising a 16S rDNA nucleotide sequence represented by SEQ ID NO: 7, a culture thereof, a lysate thereof or an extract thereof as an active ingredient. Furthermore, as the use of the novel lactic acid bacteria mixture, the present invention provides a composition for preventing, alleviating or treating intestinal damage, liver injury, allergic disease, inflammatory disease or obesity comprising a mixture of two or more lactic acid bacteria selected from *Lactobacillus brevis* comprising a 16S rDNA nucleotide sequence represented by SEQ ID NO: 1, *Bifidobacterium longum* comprising a 16S rDNA nucleotide sequence represented by SEQ ID NO: 3, *Lactobacillus plantarum* comprising a 16S rDNA nucleotide sequence represented by SEQ ID NO: 4, *Lactobacillus plantarum* comprising a 16S rDNA nucleotide sequence represented by SEQ ID NO: 5 and *Bifidobacterium longum* comprising a 16S rDNA nucleotide sequence represented by SEQ ID NO: 7, a culture thereof, a lysate thereof or an extract thereof as an active ingredient. In the composition of the present invention, the technical characteristics of the *Lactobacillus brevis*, *Lactobacillus plantarum* and *Bifidobacterium longum* are as described above, and thus the description thereof is omitted. The intestinal damage refers to a condition in which the function of the intestines (particularly small intestine or large intestine) is abnormal due to intestinal flora disturbance or the like. Preferably, the intestinal damage is intestinal permeability syndrome. Furthermore, the liver injury refers to a condition in which the function of the liver is abnormal due to external factors or internal factors. Preferably, the liver injury is selected from hepatitis, fatty liver or liver cirrhosis. Furthermore, the hepatitis includes all non-alcoholic hepatitis and alcoholic hepatitis. Moreover, the fatty liver includes all non-alcoholic fatty liver and alcoholic fatty liver. Furthermore, the allergic disease is not limited in its kind if it caused by excessive immune responses of a living body, and is preferably selected from atopic dermatitis, asthma, pharyngitis or chronic dermatitis. Furthermore, the inflammatory disease is not limited in its kind if it caused by inflammatory responses, and is preferably selected from gastritis, gastric ulcer, arthritis or colitis. Moreover, the arthritis includes rheumatoid arthritis. The colitis refers to a condition in which inflammation occurred in the large intestine due to bacterial infection or pathological fermentation of intestinal contents. The colitis includes infectious colitis and non-infectious colitis. Specific examples of the colitis include inflammatory bowel diseases, irritable bowel syndrome and the like. Furthermore, the inflammatory bowel diseases include ulcerative colitis, Crohn's disease and the like.

In the present invention, a culture of the lactic acid bacteria or a culture of the lactic acid bacteria mixture is a produced by culturing a certain strain or a mixture of strains in a medium. The medium may be selected from known liquid media or solid media, and may be, for example, MRS liquid medium, MRS agar medium or BL agar medium.

In the present invention, the composition may be embodied as a pharmaceutical composition, a food additive, a food composition (particularly, a functional food composition), a feed additive or the like depending on the intended use or aspect. In addition, the content of the lactic acid bacteria or the lactic acid bacteria mixture as an active ingredient may also be adjusted within a wide range depending on the specific type, intended use or aspect of the composition.

The content of the novel lactic acid bacteria, the novel lactic acid bacteria mixture, a culture thereof, a lysate thereof or an extract thereof as an active ingredient in the pharmaceutical composition according to the present invention is not particularly limited. For example, the content may be 0.01 to 99 wt %, preferably 0.5 to 50 wt %, more preferably 1 to 30 wt %, based on the total weight of the composition. In addition, the pharmaceutical composition according to the present invention may further contain, in addition to the active ingredient, additives such as pharmaceutically acceptable carriers, excipients or diluents. Carriers, excipients and diluents, which may be contained in the pharmaceutical composition according to the present invention, include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate and mineral oil. In addition, the pharmaceutical composition according to the present invention may further contain, in addition to the novel lactic acid bacteria, the novel lactic acid bacteria mixture, a culture thereof, a lysate thereof or an extract thereof, one or more active ingredients having the effect of preventing or treating intestinal damage, liver injury, allergic disease, inflammatory disease or obesity. The pharmaceutical composition according to the present invention may be prepared as formulations for oral administration or formulations for parenteral administration, and the formulations may be prepared using diluents or excipients, such as fillers, extenders, binders, wetting agents, disintegrants, surfactants and the like, which are commonly used. Solid formulations for oral administration include tablets, pellets, powders, granules, capsules and the like, and such solid formulations may be prepared by mixing the active ingredient with at least one excipient, for example, starch, calcium carbonate, sucrose, lactose or gelatin. In addition to simple excipients, lubricants such as magnesium stearate or talc may also be used. Liquid formulations for oral administration include suspensions, solutions, emulsions and syrup, and may contain various excipients, for example, wetting agents, flavoring agents, aromatics, preservatives and the like, in addition to water and liquid paraffin which are frequently used simple diluents. Formulations for parenteral administration include sterilized aqueous solutions, non-aqueous solutions, suspensions, emulsions, freeze-dried preparations and suppositories. Propylene glycol, polyethylene glycol, plant oils such as olive oil, injectable esters such as ethyl oleate and the like may be used as non-aqueous solvents or suspending agents. As the base of the suppositories, witepsol, Macrogol, Tween 61, cacao butter, laurin fat, glycerogelatin and the like may be used. Furthermore, the composition may preferably be formulated depending on each disease or component by a suitable method known in the art or the method disclosed in Remington's Pharmaceutical Science (the latest edition), Mack Publishing Company, Easton Pa. The pharmaceutical composition of the present invention may be administered orally or parenterally to mammals, including humans, according to a desired method. Routes for parenteral administration include skin external application, intraperitoneal injection, intrarectal injection, subcutaneous injection, intravenous injection, intramuscular injection, intrathoracic injection or the like. The dose of the pharmaceutical composition of the present invention is not particularly limited as long as it is a pharmaceutically effective amount. The dose may vary depending on the patient's weight, age, sex, health condition, diet, administration time, administration mode, excretion rate and the severity of the disease. The daily dose of the pharmaceutical composition of the present invention is not particularly limited, but is preferably 0.1 to 3000 mg/kg based on an active ingredient, more preferably 1 to 2000 mg/kg based on an active ingredient and may be administered once or several times a day.

Furthermore, the content of the novel lactic acid bacteria, the novel lactic acid bacteria mixture, a culture thereof, a lysate thereof or an extract thereof as an active ingredient in the food composition according to the present invention is 0.01 to 99 wt %, preferably 0.1 to 50 wt %, more preferably 0.5 to 25 wt %, based on the total weight of the composition, but is not limited thereto. The food composition of the present invention may be in the form of pellets, powders, granules, infusions, tablets, capsules, liquid or the like, and specific examples of the food may include meats, sausages, breads, chocolates, candies, snacks, confectioneries, pizzas, ramens, other noodles, gums, dairy products including ice creams, various kinds of soups, beverages, teas, functional water, drinks, alcoholic beverages, vitamin complexes and the like, and may include all health foods in a general sense. The food composition of the present invention may further contain sitologically acceptable carriers, various flavoring agents or natural carbohydrates as additional ingredients, in addition to the active ingredient. Additionally, the food composition of the present invention may contain various nutrients, vitamins, electrolytes, flavoring agents, coloring agents, pectic acid and its salt, alginic acid and its salt, an organic acid, a protective colloidal thickener, a pH adjusting agent, a stabilizer, a preservative, glycerin, alcohol, a carbonating agent used for carbonated drinks and the like. Additionally, the food composition of the present invention may contain fruit flesh for preparing natural fruit juices, fruit juice drinks and vegetable drinks. These ingredients may be used independently or as a mixture. The above-described natural carbohydrates may include monosaccharides such as glucose and fructose, disaccharides such as maltose and sucrose, polysaccharides such as dextrin and cyclodextrin and sugar alcohols such as xylitol, sorbitol, and erythritol. As a flavoring agent, a natural flavoring agent such as thaumatin or a stevia extract, or a synthetic flavoring agent such as saccharin or aspartame may be used.

Hereinafter, the present invention will be described in further detail with reference to examples. It is to be understood, however, that these examples are merely intended to clearly illustrate the technical characteristics of the present invention and do not limit the scope of the present invention.

I. First Experiment for Screening of Lactic Acid Bacteria and Evaluation of the Effects Thereof 1. Isolation and Identification of Lactic Acid Bacteria
(1) Isolation of Lactic Acid Bacteria from Kimchi
Each of Chinese cabbage kimchi, radish kimchi and green onion kimchi was crushed, and the crushed liquid was suspended in MRS liquid medium (MRS Broth; Difco, USA). Next, the supernatant was collected, transferred to MRS agar medium (Difco, USA) and cultured anaerobically at 37° C. for about 48 hours, and then strains that formed colonies were isolated.

(2) Isolation of Lactic Acid Bacteria from Human Feces

Human feces were suspended in GAM liquid medium (GAM broth; Nissui Pharmaceutical, Japan). Next, the supernatant was collected, transferred to BL agar medium (Nissui Pharmaceutical, Japan) and cultured anaerobically at 37° C. for about 48 hours, and then *Bifidobacterium* sp. strains that formed colonies were isolated.

(3) Identification of Screened Lactic Acid Bacteria

The physiological characteristics and 16S rDNA sequences of the strains isolated from kimchi or human feces were analyzed to identify the species of the strains, and names were given to the strains. Table 1 below the control numbers and strain names of the lactic acid bacteria isolated from Chinese cabbage kimchi, radish kimchi, green onion kimchi and human feces.

TABLE 1

| Control No. | Strain name |
|---|---|
| 1 | *Lactobacillus acidophilus* CH1 |
| 2 | *Lactobacillus acidophilus* CH2 |
| 3 | *Lactobacillus acidophilus* CH3 |
| 4 | *Lactobacillus brevis* CH4 |
| 5 | *Lactobacillus curvatus* CH5 |
| 6 | *Lactobacillus brevis* CH6 |
| 7 | *Lactobacillus casei* CH7 |
| 8 | *Lactobacillus planantrum* CH8 |
| 9 | *Lactobacillus sakei* CH9 |
| 10 | *Lactobacillus curvatus* CH10 |
| 11 | *Lactobacillus sakei* CH11 |
| 12 | *Lactobacillus curvatus* CH12 |
| 13 | *Lactobacillus plantarum* CH13 |
| 14 | *Lactobacillus fermentum* CH14 |
| 15 | *Lactobacillus fermentum* CH15 |
| 16 | *Lactobacillus gasseri* CH16 |
| 17 | *Lactobacillus paracasei* CH17 |
| 18 | *Lactobacillus helveticus* CH18 |
| 19 | *Lactobacillus helveticus* CH19 |
| 20 | *Lactobacillus johnsonii* CH20 |
| 21 | *Lactobacillus johnsonii* CH21 |
| 22 | *Lactobacillus johnsonii* CH22 |
| 23 | *Lactobacillus brevis* CH23 |
| 24 | *Lactobacillus paracasei* CH24 |
| 25 | *Lactobacillus kimchi* CH25 |
| 26 | *Lactobacillus gasseri* CH26 |
| 27 | *Lactobacillus paracasei* CH27 |
| 28 | *Lactobacillus pentosus* CH28 |
| 29 | *Lactobacillus pentosus* CH29 |
| 30 | *Lactobacillus reuteri* CH30 |
| 31 | *Lactobacillus sakei* CH31 |
| 32 | *Lactobacillus johnsonii* CH32 |
| 33 | *Lactobacillus sakei* CH33 |
| 34 | *Lactobacillus sakei* CH34 |
| 35 | *Lactobacillus plantarum* CH35 |
| 36 | *Lactobacillus sanfranciscensis* CH36 |
| 37 | *Bifidobacterium pseudocatenulatum* CH37 |
| 38 | *Bifidobacterium pseudocatenulatum* CH38 |
| 39 | *Bifidobacterium adolescentis* CH39 |
| 40 | *Bifidobacterium adolescentis* CH40 |
| 41 | *Bifidobacterium adolescentis* CH41 |
| 42 | *Bifidobacterium animalis* CH42 |
| 43 | *Bifidobacterium animalis* CH43 |
| 44 | *Bifidobacterium bifidum* CH44 |
| 45 | *Bifidobacterium bifidum* CH45 |
| 46 | *Bifidobacterium breve* CH46 |
| 47 | *Bifidobacterium breve* CH47 |
| 48 | *Bifidobacterium breve* CH48 |
| 49 | *Bifidobacterium catenulatum* CH49 |
| 50 | *Bifidobacterium catenulatum* CH50 |
| 51 | *Bifidobacterium dentium* CH51 |
| 52 | *Bifidobacterium infantis* CH52 |

TABLE 1-continued

| Control No. | Strain name |
|---|---|
| 53 | *Bifidobacterium infantis* CH53 |
| 54 | *Bifidobacterium infantis* CH54 |
| 55 | *Bifidobacterium longum* CH55 |
| 56 | *Bifidobacterium longum* CH56 |
| 57 | *Bifidobacterium longum* CH57 |
| 58 | *Bifidobacterium longum* CH58 |
| 59 | *Bifidobacterium longum* CH59 |
| 60 | *Bifidobacterium longum* CH60 |

Among the strains shown in Table 1 above, *Lactobacillus brevis* CH23 was a gram-positive anaerobic *bacillus*, did not form spores, and could survive even under aerobic conditions. Furthermore, *Lactobacillus brevis* CH23 survived at 10 to 42° C. and was an acid-resistant strain stable at pH 2 for 2 hours. Furthermore, *Lactobacillus brevis* CH23 survived even in 2% sodium chloride solution and actively produced glucosidase. In addition, to chemically classify *Lactobacillus brevis* CH23, the 16S rDNA thereof was analyzed, and as a result, it was shown that *Lactobacillus brevis* CH23 had a nucleotide sequence of SEQ ID NO: 1. The 16S rDNA nucleotide sequence of *Lactobacillus brevis* CH23 was identified by BLAST in the Genebank (ncbi.nlm.nih.gov) and as a result, a *Lactobacillus brevis* strain having the same 16S rDNA nucleotide sequence as that of *Lactobacillus brevis* CH23 was not found, and *Lactobacillus brevis* CH23 showed a homology of 99% with the 16S rDNA sequence of *Lactobacillus brevis* strain FJ004.

Among the strains shown in Table 1 above, *Lactobacillus johnsonii* CH32 was a gram-positive anaerobic *bacillus*, did not form spores, and could survive under aerobic conditions. Furthermore, *Lactobacillus johnsonii* CH32 survived stably at a temperature of up to 45° C., and was an acid-resistant strain stable in pH 2 for 2 hours. Moreover, *Lactobacillus johnsonii* CH32 actively produced β-glucosidase, but did not produce β-glucuronidase. In addition, to chemically classify *Lactobacillus johnsonii* CH32, the 16S rDNA thereof was analyzed, and as a result, it was shown that *Lactobacillus johnsonii* CH32 had a nucleotide sequence of SEQ ID NO: 2. The 16S rDNA nucleotide sequence of *Lactobacillus johnsonii* CH32 was identified by BLAST in Genebank (ncbi.nlm.nih.gov), and as a result, a *Lactobacillus johnsonii* strain having the same 16S rDNA nucleotide sequence as that of *Lactobacillus johnsonii* CH32 was not found, and *Lactobacillus johnsonii* CH32 showed a homology of 99% with the 16S rDNA sequence of *Lactobacillus johnsonii* strain JCM 2012.

Among the strains shown in Table 1 above, *Bifidobacterium longum* CH57 was a gram-positive anaerobic *bacillus*, did not form spores, and showed very low viability under aerobic conditions. Furthermore, *Bifidobacterium longum* CH57 was thermally unstable. Furthermore, *Bifidobacterium longum* CH57 actively produced glucosidase, but did not produce β-glucuronidase. In addition, to chemically classify *Bifidobacterium longum* CH57, the 16S rDNA thereof was analyzed, and as a result, it was shown that *Bifidobacterium longum* CH57 had a nucleotide sequence of SEQ ID NO: 3. The 16S rDNA nucleotide sequence of *Bifidobacterium longum* CH57 was identified by BLAST in the Genebank (ncbi.nlm.nih.gov), and as a result, a *Bifidobacterium longum* strain having the same 16S rDNA nucleotide sequence as that of *Bifidobacterium longum* CH57 was not found, and *Bifidobacterium longum* CH57 showed a homology of 99% with the 16S rDNA sequence of *Bifidobacterium longum* strain CBT-6.

In addition, among the physiological characteristics of *Lactobacillus brevis* CH23, *Lactobacillus johnsonii* CH32 and *Bifidobacterium longum* CH57, the carbon source utilization was analyzed using a sugar fermentation by an API kit (model: API 50 CHL; manufactured by BioMerieux's, USA). Table 2 below shows the results of analyzing the carbon source utilization of *Lactobacillus brevis* CH23; Table 3 below shows the results of analyzing the carbon source utilization of *Lactobacillus johnsonii* CH32; and Table 4 below shows the results of analyzing the carbon source utilization of *Bifidobacterium longum* CH57. In Tables 2, 3 and 4, "+" indicates the case in which carbon source utilization is positive; "−" indicates the case in which carbon source utilization is negative; and "±" indicates the case in which carbon source utilization is ambiguous. As shown in Tables 2, 3 and 4 below, *Lactobacillus brevis* CH23, *Lactobacillus johnsonii* CH32 and *Bifidobacterium longum* CH57 showed carbon source utilization different from that of other strains of the same species with respect to some carbon sources.

TABLE 2

| Carbon source | *L. brevis*[1] | *L. brevis* CH23 | Carbon source | *L. brevis*[1] | *L. brevis* CH23 |
|---|---|---|---|---|---|
| glycerol | − | − | salicin | + | + |
| erythritol | − | − | cellobiose | + | − |
| D-arabinose | − | − | maltose | + | + |
| L-arabinose | + | − | lactose | + | − |
| D-ribose | + | + | melibiose | − | + |
| D-xylose | + | + | sucrose | + | − |
| L-xylose | − | − | trehalose | + | − |
| D-adonitol | − | − | inulin | + | − |
| methyl-β-D-xylopyranoside | − | − | melezitose | + | − |
| D-galactose | + | − | raffinose | − | − |
| D-glucose | + | + | starch | − | − |
| D-fructose | + | + | glycogen | − | − |
| D-mannose | + | − | xylitol | − | − |
| L-sorbose | − | − | gentiobiose | + | − |
| L-rhamnose | − | − | D-turanose | + | − |
| dulcitol | + | − | D-lyxose | − | − |
| inositol | − | − | D-tagatose | + | − |
| mannitol | + | − | D-fucose | − | − |
| sorbitol | + | − | L-fucose | − | − |
| α-methyl-D-mannoside | − | − | D-arabitol | − | − |
| α-methly-D-glucoside | − | − | L-arabitol | − | − |
| N-acetyl-glucosamine | + | ± | gluconate | + | ± |
| amygdalin | + | − | 2-keto-gluconate | − | − |
| arbutin | + | − | 5-keto-gluconate | − | + |
| esculin | + | + | | | |

[1]Suriasih K., Aryanta W R, MahardikaG, Astawa N M. Microbiological and Chemical Properties of Kefir Made of Bali Cattle Milk. Food Science and Quality Management 2012; 6: 112-22.

TABLE 3

| Carbon source | *L. johnsonii*[2] | *L. johnsonii*[2] CH32 | Carbon source | *L. johnsonii*[2] | *L. johnsonii*[2] CH32 |
|---|---|---|---|---|---|
| glycerol | − | − | salicin | − | − |
| erythritol | − | − | cellobiose | + | − |
| D-arabinose | − | − | maltose | − | + |
| L-arabinose | − | − | lactose | − | + |
| D-ribose | − | − | melibiose | + | − |
| D-xylose | − | − | sucrose | + | + |
| L-xylose | − | − | trehalose | + | − |
| D-adonitol | − | − | inulin | − | − |
| methyl-β-D-xylopyranoside | − | − | melezitose | − | − |
| D-galactose | − | − | raffinose | + | − |
| D-glucose | − | + | starch | − | − |
| D-fructose | − | + | glycogen | − | − |
| D-mannose | + | + | xylitol | − | − |
| L-sorbose | − | − | gentiobiose | − | + |
| L-rhamnose | − | − | D-turanose | − | − |
| dulcitol | − | − | D-lyxose | − | − |
| inositol | − | − | D-tagatose | − | − |
| mannitol | − | − | D-fucose | − | − |
| sorbitol | − | − | L-fucose | − | − |
| α-methyl-D-mannoside | − | − | D-arabitol | − | − |
| α-methly-D-glucoside | − | − | L-arabitol | − | − |
| N-acetyl-glucosamine | + | + | gluconate | − | − |
| amygdalin | − | − | 2-keto-gluconate | − | − |

TABLE 3-continued

| | Strain name | | | Strain name | |
| --- | --- | --- | --- | --- | --- |
| Carbon source | L. johnsonii[2] | L. johnsonii[2] CH32 | Carbon source | L. johnsonii[2] | L. johnsonii[2] CH32 |
| arbutin | − | − | 5-keto-gluconate | − | − |
| esculin | − | − | | | |

[2] Pridmore R D, Berger B, Desiere F, Vilanova D, Barretto C, Pittet A C, Zwahlen M C, Rouvet M, Altermann E, Barrangou R, Mollet B, Mercenier A, Klaenhammer T, Arigoni F, Schell M A. The genome sequence of the probiotic intestinal bacterium Lactobacillus johnsonii NCC 533. Proc Natl Acad Sci USA. 2004 Feb. 24; 101(8): 2512-7.

TABLE 4

| | Strain name | | | Strain name | |
| --- | --- | --- | --- | --- | --- |
| Carbon source | B. longum[3] | B. longum[3] CH57 | Carbon source | B. longum[3] | B. longum[3] CH57 |
| glycerol | ± | − | salicin | ± | − |
| erythritol | − | − | cellobiose | ± | ± |
| D-arabinose | − | − | maltose | − | − |
| L-arabinose | − | − | lactose | − | − |
| D-ribose | ± | − | melibiose | − | − |
| D-xylose | − | − | sucrose | + | ± |
| L-xylose | − | − | trehalose | ± | − |
| D-adonitol | − | − | inulin | − | − |
| methyl-β-xylopyranoside | − | − | melezitose | − | − |
| D-galactose | + | + | raffinose | − | − |
| D-glucose | + | + | starch | − | − |
| D-fructose | + | + | glycogen | − | − |
| D-mannose | − | − | xylitol | − | − |
| L-sorbose | − | − | gentiobiose | − | − |
| L-rhamnose | − | − | D-turanose | − | − |
| dulcitol | − | − | D-lyxose | − | − |
| inositol | − | − | D-tagatose | − | − |
| mannitol | + | − | D-fucose | − | − |
| sorbitol | − | − | L-fucose | − | − |
| α-methyl-D-mannoside | − | − | D-arabitol | − | − |
| α-methly-D-glucoside | − | − | L-arabitol | − | − |
| N-acetyl-glucosamine | ± | − | gluconate | ± | − |
| amygdalin | − | − | 2-keto-gluconate | − | − |
| arbutin | ± | − | 5-keto-gluconate | − | − |
| esculin | − | − | | | |

[3] Lukacova D, Karovucova J, Greifova M, Greif G, Sovcikova A, Kohhajdova Z. In vitro testing of selected probiotic characteristics of Lactobacillus plantarum and Bifidobacterium longum. Journal of Food and Nutrition Research 2006; 45: 77-83.

(4) Information on Deposition of Lactic Acid Bacteria

The present inventors deposited *Lactobacillus brevis* CH23 with the Korean Culture Center of Microorganisms (address: Yurim Building, 45, Hongjenae 2ga-gil, Seodaemun-gu, Seoul, Korea), an international depositary authority, on Sep. 1, 2015 under accession number KCCM 11762P. Furthermore, the present inventors deposited *Lactobacillus johnsonii* CH32 with the Korean Culture Center of Microorganisms (address: Yurim Building, 45, Hongjenae 2ga-gil, Seodaemun-gu, Seoul, Korea), an international depositary authority, on Sep. 1, 2015, under accession number KCCM 11763P. Furthermore, the present inventors deposited *Bifidobacterium longum* CH57 with the Korean Culture Center of Microorganisms (address: Yurim Building, 45, Hongjenae 2ga-gil, Seodaemun-gu, Seoul, Korea), an international depositary authority, on Sep. 1, 2015 under accession number KCCM 11764P.

2. Evaluation of the Effect of Lactic Acid Bacteria on Alleviation of Intestinal Damage or Intestinal Permeability In order to evaluate the effect of the lactic acid bacteria isolated from kimchi or human feces, on the alleviation of intestinal damage or internal permeability, the antioxidant activity, lipopolysaccharide (LPS) production inhibitory activity, β-glucuronidase (harmful intestinal enzyme) inhibitory activity and tight junction protein expression-inducing activity of the lactic acid bacteria were measured.

(1) Experimental Methods

*Antioxidant Activity

DPPH (2,2-diphenyl-1-picrylhydrazyl) was dissolved in ethanol to a concentration of 0.2 mM to prepare a DPPH solution. A lactic acid bacteria suspension ($1\times10^8$ CFU/ml) or a vitamin C solution (1 g/ml) was added to 0.1 ml of the DPPH solution and cultured at 37° C. for 20 minutes. The culture was centrifuged at 3000 rpm for 5 minutes, and the supernatant was collected. Next the absorbance of the supernatant at 517 nm was measured, and the antioxidant activity of the lactic acid bacteria was calculated.

*Lipopolysaccharide (LPS) Production-Inhibitory Activity 0.1 g of human fresh feces was suspended in 0.9 ml of sterile physiological saline and diluted 100-fold with general anaerobic medium to prepare a fecal suspension. 0.1 ml of the fecal suspension and 0.1 ml of lactic acid bacteria ($1\times10^4$ or $1\times10^5$ CFU) were added to 9.8 ml of sterile anaerobic medium (Nissui Pharmaceuticals, Japan) and cultured anaerobically for 24 hours. Next, the culture was sonicated for about 1 hour to disrupt the outer cell membrane of the bacteria, and centrifuged at 5000×g, and the supernatant was collected. Next, the content of LPS (lipopolysaccharide) (which is a typical endotoxin) in the supernatant was measured by a LAL (Limulus Amoebocyte Lysate) assay kit (manufactured by Cape Cod Inc., USA). In addition, in order to evaluate the *E. coli* proliferation inhibitory activity of the lactic acid bacteria, the culture obtained through the same experiment as described above was diluted 1000-fold and 100000-fold and cultured in DHL medium, and then the number of *E. coli* cells was counted.

*β-Glucuronidase Inhibitory Activity 0.1 ml of 0.1 mM p-nitrophenyl-β-D-glucuronide solution, 0.2 ml of 50 mM phosphate buffered saline and 0.1 ml of a lactic acid bacteria suspension (prepared by suspending of a lactic acid bacteria culture in 5 ml of physiological saline) were placed in a reactor and subjected to an β-glucuronidase enzymatic reaction, and 0.5 ml of 0.1 mM NaOH solution was added to stop the reaction. Next, the reaction solution was centrifuged at 3000 rpm for 5 minutes, and the supernatant was collected. Then, the absorbance of the supernatant at 405 nm was measured.

*Tight Junction Protein Expression-Inducing Activity

Caco2 cells obtained from the Korean Cell Line Bank were cultured in RPMI 1640 medium for 48 hours, and then the cultured Caco2 cells were dispensed to each well of a 12-well plate at a density of $2 \times 10^6$ cells/well. Next, each well was treated with 1 μg of LPS (lipopolysaccharide) or a combination of 1 μg of LPS (lipopolysaccharide) and $1 \times 10^3$ CFU of lactic acid bacteria and incubated for 24 hours. Next, the cultured cells were collected from each well, and the expression level of tight junction protein ZO-1 in the cells was measured by an immunoblotting method.

(2) Experimental Results

The antioxidant activity, lipopolysaccharide (LPS) production inhibitory activity, β-glucuronidase inhibitory activity and tight junction protein expression-inducing activity of the lactic acid bacteria isolated from kimchi or human feces were measured, and the results of the measurement are shown in Tables 5 and 6 below. As shown in Tables 5 and 6 below, *Lactobacillus curvatus* CH5, *Lactobacillus sakei* CH11, *Lactobacillus brevis* CH23, *Lactobacillus johnsonii* CH32, *Bifidobacterium pseudocatenulatum* CH38 and *Bifidobacterium longum* CH57 had excellent antioxidant activity, strongly inhibited lipopolysaccharide (LPS) production and β-glucuronidase activity, and strongly induced the expression of tight junction protein. These lactic acid bacteria have an excellent antioxidant effect, have an excellent effect of inhibiting the enzymatic activity of intestinal flora's harmful bacteria associated with inflammation and carcinogenesis, inhibit the production of endotoxin LPS (lipopolysaccharide) produced by intestinal flora's harmful bacteria, and induce the expression of tight junction protein. Thus, these lactic acid bacteria can improve intestinal permeability syndrome.

TABLE 5

| Control No. | Strain name | Antioxidant activity | Beta-glucuronidase inhibitory activity | LPS production inhibitory activity | Tight junction protein expression inducing activity |
|---|---|---|---|---|---|
| 1 | *Lactobacillus acidophilus* CH1 | + | + | − | − |
| 2 | *Lactobacillus acidophilus* CH2 | + | + | + | − |
| 3 | *Lactobacillus acidophilus* CH3 | + | + | + | − |
| 4 | *Lactobacillus brevis* CH4 | + | + | − | − |
| 5 | *Lactobacillus curvatus* CH5 | +++ | + | +++ | ++ |
| 6 | *Lactobacillus brevis* CH6 | + | + | − | − |
| 7 | *Lactobacillus casei* CH7 | + | + | − | − |
| 8 | *Lactobacillus planantrum* CH8 | + | + | − | − |
| 9 | *Lactobacillus sakei* CH9 | − | + | − | − |
| 10 | *Lactobacillus curvatus* CH10 | − | + | − | − |
| 11 | *Lactobacillus sakei* CH11 | +++ | + | +++ | ++ |
| 12 | *Lactobacillus curvatus* CH12 | − | + | − | + |
| 13 | *Lactobacillus plantarum* CH13 | − | + | − | − |
| 14 | *Lactobacillus fermentum* CH14 | − | + | − | − |
| 15 | *Lactobacillus fermentum* CH15 | +++ | + | ++ | − |
| 16 | *Lactobacillus gasseri* CH16 | + | + | − | − |
| 17 | *Lactobacillus paracasei* CH17 | + | + | − | − |
| 18 | *Lactobacillus helveticus* CH18 | + | + | − | − |
| 19 | *Lactobacillus helveticus* CH19 | + | + | − | − |
| 20 | *Lactobacillus johnsonii* CH20 | + | + | − | + |
| 21 | *Lactobacillus johnsonii* CH21 | + | + | − | + |
| 22 | *Lactobacillus johnsonii* CH22 | + | + | − | + |
| 23 | *Lactobacillus brevis* CH23 | +++ | + | ++ | ++ |
| 24 | *Lactobacillus paracasei* CH24 | + | + | − | − |
| 25 | *Lactobacillus kimchi* CH25 | + | + | − | − |
| 26 | *Lactobacillus gasseri* CH26 | + | + | − | − |
| 27 | *Lactobacillus paracasei* CH27 | + | + | − | + |
| 28 | *Lactobacillus pentosus* CH28 | + | + | − | − |
| 29 | *Lactobacillus pentosus* CH29 | + | + | − | − |
| 30 | *Lactobacillus reuteri* CH30 | + | − | − | − |

TABLE 6

| Control No. | Strain name | Antioxidant activity | Beta-glucuronidase inhibitory activity | LPS production inhibitory activity | Tight junction protein expression inducing activity |
|---|---|---|---|---|---|
| 31 | *Lactobacillus sakei* CH31 | − | + | − | + |
| 32 | *Lactobacillus johnsonii* CH32 | +++ | + | ++ | ++ |
| 33 | *Lactobacillus sakei* CH33 | + | + | − | + |
| 34 | *Lactobacillus sakei* CH34 | + | + | − | + |
| 35 | *Lactobacillus plantanrum* CH35 | + | + | + | + |
| 36 | *Lactobacillus sanfranciscensis* CH36 | + | + | + | + |
| 37 | *Bifidobacterium pseudocatenulatum* CH37 | − | + | − | + |
| 38 | *Bifidobacterium pseudocatenulatum* CH38 | +++ | + | ++ | ++ |
| 39 | *Bifidobacterium adolescentis* CH39 | − | + | − | + |
| 40 | *Bifidobacterium adolescentis* CH40 | − | + | +++ | + |
| 41 | *Bifidobacterium adolescentis* CH41 | + | + | − | + |
| 42 | *Bifidobacterium animalis* CH42 | + | + | − | − |
| 43 | *Bifidobacterium animalis* CH43 | + | + | − | − |
| 44 | *Bifidobacterium bifidum* CH44 | + | + | − | − |
| 45 | *Bifidobacterium bifidum* CH45 | + | + | − | − |
| 46 | *Bifidobacterium breve* CH46 | + | − | − | − |
| 47 | *Bifidobacterium breve* CH47 | + | + | − | + |
| 48 | *Bifidobacterium breve* CH48 | + | + | − | + |
| 49 | *Bifidobacterium catenulatum* CH49 | + | + | − | ++ |
| 50 | *Bifidobacterium catenulatum* CH50 | − | + | − | − |
| 51 | *Bifidobacterium dentium* CH51 | + | − | − | − |
| 52 | *Bifidobacterium infantis* CH52 | − | + | − | − |
| 53 | *Bifidobacterium infantis* CH53 | − | + | − | − |
| 54 | *Bifidobacterium infantis* CH54 | + | + | − | − |
| 55 | *Bifidobacterium longum* CH55 | + | + | − | + |
| 56 | *Bifidobacterium longum* CH56 | +++ | + | ++ | + |
| 57 | *Bifidobacterium longum* CH57 | +++ | + | +++ | ++ |
| 58 | *Bifidobacterium longum* CH58 | + | + | + | + |
| 59 | *Bifidobacterium longum* CH59 | + | + | + | + |
| 60 | *Bifidobacterium longum* CH60 | + | − | + | + |

\* The final concentration of lactic acid bacteria in measurement of antioxidant activity: $1 \times 10^4$ CFU/ml; the concentration of lactic acid bacteria added for measurement of beta-glucuronidase inhibitory activity and lipopolysaccharide (LPS) production inhibitory activity: $1 \times 10^4$ CFU/ml; the concentration of lactic acid bacteria in measurement of tight junction protein expression-inducing activity: $1 \times 10^4$ CFU/ml.
\* Criteria for measurement of various activities of lactic acid bacteria: very strongly (+++; >90%); strongly (++; >60-90%); weakly (+; >20-60%); not or less than 20% (−; <20%).

3. Evaluation of the Effect of Lactic Acid Bacteria on Alleviation of Liver Injury Based on evaluation of the effect of the lactic acid bacteria on the alleviation of intestinal damage or intestinal permeability syndrome, the following seven strains were selected: *Lactobacillus curvatus* CH5, *Lactobacillus sakei* CH11, *Lactobacillus fermentum* CH15, *Lactobacillus brevis* CH23, *Lactobacillus johnsonii* CH32, *Bifidobacterium pseudocatenulatum* CH38 and *Bifidobacterium longum* CH57. The effect of each of these selected strains or a mixture of these strains on the alleviation of liver injury was evaluated using various liver injury model animals.

(1) Measurement of the Liver Injury-Alleviating Effect of Lactic Acid Bacteria by an Experiment Using Model Animals Having Liver Injury Induced by D-Galactosamine 1) Experimental Method Mice (C57BL/6, male) were divided into several groups, each consisting of 6 animals. D-Galactosamine was administered intraperitoneally to the test animals of groups other than a normal group at a dose of 800 mg/kg to induce liver injury. From 2 hours after intraperitoneal administration of D-galactosamine, $1 \times 10^9$ CFU of lactic acid bacteria were administered orally to the test animals of groups other than the normal group and the negative control group, once a day for 3 days. In addition, silymarin in place of lactic acid bacteria was administered orally to the test animals of the positive control group at a dose of 100 mg/kg, once a day for 3 days. At 6 hours after the last administration of the drug, blood was taken from the heart. The taken blood was allowed to stand at room temperature for 60 minutes, and centrifuged at 3,000 rpm for 15 minutes to separate serum. The GPT (glutamic pyruvate transaminase) and GOT (glutamic oxalacetic transaminase) levels in the separated serum were measured using a blood assay kit (ALT & AST measurement kit; Asan Pharm. Co., Korea).

In addition, liver tissue was dissected from the test animals, and the amount of malondialdehyde (MDA) present in the liver tissue was measured. Malondialdehyde is a marker of lipid peroxidation. Specifically, 0.5 g of the dissected liver tissue was added to a 16-fold volume of RIPA solution (0.21M mannitol, 0.1M EDTA-2Na, 0.07M sucrose, 0.01M Trizma base), and then homogenized using a homogenizer. The homogenized solution was centrifuged at 3,000 rpm for 10 minutes, and the liver homogenate was collected. 0.5 ml of the liver homogenate was added to 0.4 ml of 10% SDS, incubated at 37° C. for 30 minutes, and cooled, and then 3 ml of 1% phosphate buffer and 1 ml of 0.6% TBA were added thereto and heated on a water bath at 100° C. for 45 minutes to develop the sample solution. The developed sample solution was added to and mixed with 4 ml of n-butanol, and then centrifuged at 3000 rpm for 10 minutes, and the supernatant was collected. The absorbance of the collected supernatant at 535 nm was measured to quantify MDA. In addition, a calibration curve for MDA measurement was plotted using 1,1,3,3-tetraethoxypropane.

2) Experimental Results

Figure 2:
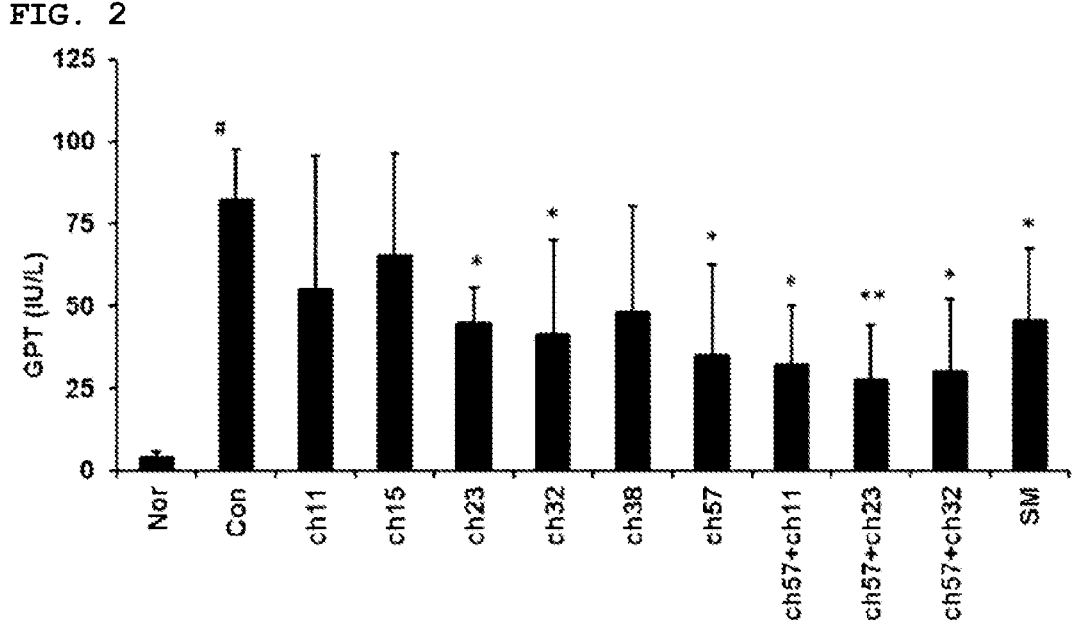
FIG. 2 is a graph showing the change in GPT value when lactic acid bacteria were administered to model animals having liver injury induced by D-galactosamine, in a first experiment of the present invention.

FIG. 1 is a graph showing the change in GOT value when lactic acid bacteria were administered to model animals having liver injury induced by D-galactosamine; FIG. 2 is a graph showing the change in GPT value when lactic acid bacteria were administered to model animals having liver injury induced by D-galactosamine; and FIG. 3 is a graph showing the change in MDA value when lactic acid bacteria were administered to model animals having liver injury induced by D-galactosamine.

Figure 3:
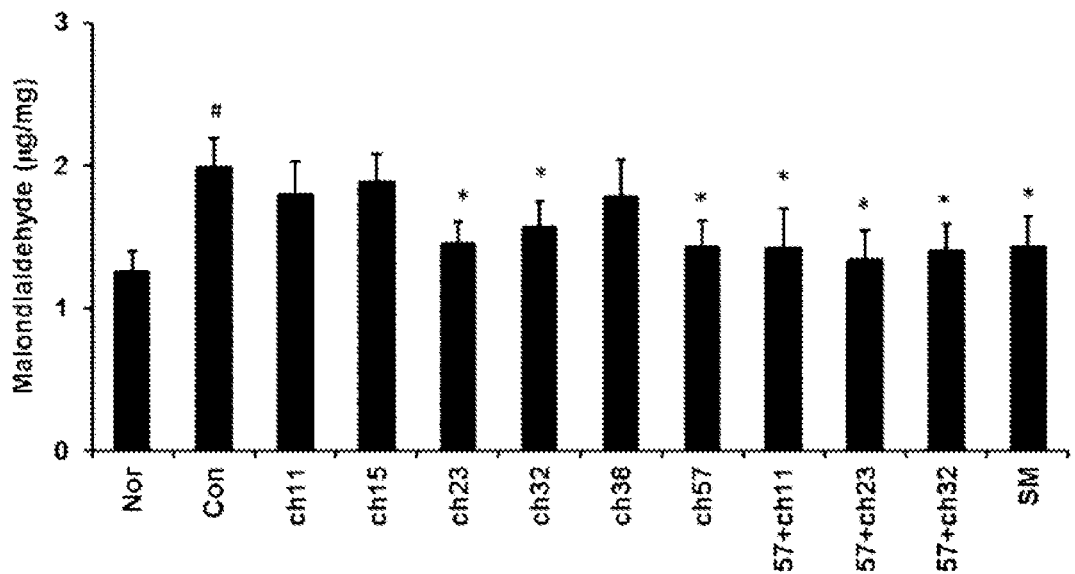
FIG. 3 is a graph showing the change in MDA value when lactic acid bacteria were administered to model animals having liver injury induced by D-galactosamine, in a first experiment of the present invention.

On the x-axis of FIGS. 1 to 3, "Nor" indicates a normal group; "Con" indicates a negative control group in which any drugs were not administered to model animals having liver injury induced by D-galactosamine; "ch11" indicates a group administered with *Lactobacillus sakei* CH11; "ch15" indicates a group administered with *Lactobacillus fermentum* CH15; "ch23" indicates a group administered with *Lactobacillus brevis* CH23; "ch32" indicates a group administered with *Lactobacillus johnsonii* CH32; "ch38" indicates a group administered with *Bifidobacterium pseudocatenulatum* CH38; "ch57" indicates a group administered with *Bifidobacterium longum* CH57; "ch57+ch11" indicates a group administered with a lactic acid bacteria mixture prepared by mixing *Bifidobacterium longum* CH57 and *Lactobacillus sakei* CH11 in the same amount; "ch57+ch23" indicates a group administered with a lactic acid bacteria mixture prepared by mixing *Bifidobacterium longum* CH57 and *Lactobacillus brevis* CH23 in the same amount; "ch57+ch32" indicates a group administered with a lactic acid bacteria mixture prepared by mixing *Bifidobacterium longum* CH57 and *Lactobacillus johnsonii* CH32 in the same amount; and "SM" indicates a positive control group administered with silymarin instead of lactic acid bacteria.

As shown in FIGS. 1 to 3, when each of *Lactobacillus brevis* CH23, *Lactobacillus johnsonii* CH32 and *Bifidobacterium longum* CH57 was administered to the model animals in which GOT, GPT and MAD values increased due to liver injury, the liver injury was alleviated. Particularly, when a lactic acid bacteria mixture of *Bifidobacterium longum* CH57 and *Lactobacillus brevis* CH23 or a lactic acid bacteria mixture of *Bifidobacterium longum* CH57 and *Lactobacillus johnsonii* CH32 was administered, the liver injury was greatly alleviated. In addition, specific lactic acid bacteria or a mixture of lactic acid bacteria selected therefrom showed a better effect on the alleviation of liver injury than silymarin which is used as a drug for treating liver injury. These results suggest that specific lactic acid bacteria or a mixture of lactic acid bacteria selected therefrom is effective in alleviating fatty liver induced by alcohol and high-fat diets, or in alleviating liver diseases resulting from oxidative stress.

(2) Measurement of the Liver Injury-Alleviating Effect of Lactic Acid Bacteria by an Experiment Using Model Animals Having Liver Injury Induced by Tert-Butylperoxide 1) Experimental Method Mice (C57BL/6, male) were divided into several groups, each consisting of 6 animals. Tert-butylperoxide was administered intraperitoneally to the test animals of groups other than a normal group in an amount of 2.5 mmol/kg to induce liver injury. From 2 hours after intraperitoneal administration of tert-butylperoxide, $2 \times 10^9$ CFU of lactic acid bacteria were administered orally to the test animals of groups other than the normal group and the negative control group, once a day for 3 days. In addition, silymarin in place of lactic acid bacteria was administered orally to the test animals of the positive control group at a dose of 100 mg/kg, once a day for 3 days. At 6 hours after the last administration of the drug, blood was taken from the heart. The taken blood was allowed to stand at room temperature for 60 minutes, and centrifuged at 3,000 rpm for 15 minutes to separate serum. The GPT (glutamic pyruvate transaminase) and GOT (glutamic oxalacetic transaminase) levels in the separated serum were measured using a blood assay kit ((ALT & AST measurement kit; Asan Pharm. Co., Korea).

2) Experimental Results

Table 7 below shows the changes in GOT and GPT values when lactic acid bacteria were administered to the model animals having liver injury induced by tert-butylperoxide. As shown in Table 7 below, *Lactobacillus brevis* CH23, *Lactobacillus johnsonii* CH32 and *Bifidobacterium longum* CH57 showed excellent effects on the alleviation of liver injury compared to silymarin, and a lactic acid bacteria mixture of *Bifidobacterium longum* CH57 and *Lactobacillus brevis* CH23 or a lactic acid bacteria mixture of *Bifidobacterium longum* CH57 and *Lactobacillus johnsonii* CH32 showed a better effect on the alleviation of liver injury.

TABLE 7

| Test groups | GOT (IU/L) | GPT (IU/L) |
| --- | --- | --- |
| Normal group | 36.1 | 26.3 |
| Negative control group | 84.1 | 96.1 |
| Group administered with CH23 | 58.0 | 74.2 |
| Group administered with CH32 | 53.0 | 70.5 |
| Group administered with CH57 | 57.6 | 71.2 |
| Group administered with CH57 + CH23 | 48.6 | 64.3 |
| Group administered with CH57 + CH32 | 51.2 | 68.4 |
| Group administered with silymarin | 61.7 | 69.1 |

In Table 7 above, "CH23" indicates *Lactobacillus brevis* CH23; "CH32" indicates *Lactobacillus johnsonii* CH32; "CH57" indicates *Bifidobacterium longum* CH57; "CH57+CH23" indicates a lactic acid bacteria mixture prepared by mixing *Bifidobacterium longum* CH57 and *Lactobacillus brevis* CH23 in the same amount; and "CH57+CH32" indicates a lactic acid bacteria mixture prepared by mixing *Bifidobacterium longum* CH57 and *Lactobacillus johnsonii* CH32 in the same amount.

4. Evaluation of the Effect of Lactic Acid Bacteria on Alleviation of Allergy (1) Measurement of the Inhibition of Degranulation by Lactic Acid Bacteria The RBL-2H3 cell line (rat mast cell line, the Korean Cell Line Bank, Cat. No. 22256) was cultured with DMEM (Dulbeccos' modified Eagle's medium, Sigma, 22256) containing 10% FBS (fetal bovine serum) and L-glutamine in a humidified 5% $CO_2$ incubator at 37° C. The cells contained in the culture medium were floated using trypsin-EDTA solution, and the floated cells were isolated, collected and used in the experiment. The collected RBL-2H3 cells were dispensed into a 24-well plate at a density of $5 \times 10^5$ cells/well and sensitized by incubation with 0.5 µg/ml of mouse monoclonal IgE for 12 hours. The sensitized cells were washed with 0.5 ml of siraganian buffer (119 mM NaCl, 5 mM KCl, 0.4 mM $MgCl_2$, 25 mM PIPES, 40 mM NaOH, pH 7.2), and then incubated with 0.16 ml of siraganian buffer (supplemented with 5.6 mM glucose, 1 mM $CaCl_2$, 0.1% BSA) at 37° C. for 10 minutes. Next, lactic acid bacteria as a test drug were added to the cell culture to a concentration of $1 \times 10^4$ CFU/ml, or 0.04 ml of DSCG (disodium cromoglycate) as a control drug was added to the cell culture, and after 20 minutes, the cells were activated with 0.02 ml of antigen (1 µg/ml DNP-BSA) at 37° C. for 10 minutes. Next, the cell culture was centrifuged at 2000 rpm for 10 minutes, and the supernatant was collected. 0.025 ml of the collected supernatant was transferred to a 96-well plate, and then 0.025 ml of 1 mM p-NAG (a solution of p-nitrophenyl-N-acetyl-β-D-glucosamide in 0.1M citrate buffer, pH 4.5) was added thereto, and then the mixture was allowed to react at 37° C. for 60 minutes. Next, the reaction was stopped by addition of 0.2 ml of 0.1M Na$_2$CO$_3$/NaHCO$_3$, and the absorbance at 405 nm was measured by an ELISA analyzer.

(2) Measurement of the Inhibition of Itching by Lactic Acid Bacteria

BALB/c mice were divided into several groups, each consisting of 5 animals. 1×10$^9$ CFU of lactic acid bacteria as a test drug were administered orally to test groups other than a normal group and a control group, once a day for 3 days, or DSCG (disodium cromoglycate) or Azelastine as a control drug was administered orally in an amount of 0.2 mg/mouse, once a day for 3 days. At 1 hour after the last administration of the drug, the mice were allowed to stand in an observation cage (24 cm×22 cm×24 cm) for 10 minutes so as to be acclimated to the environment, and then the back portion of the head was shaved. Next, the mice of the normal group were injected with physiological saline, and the mice of the other test groups were injected with an itching inducer (50 μg of compound 48/80; Sigma, USA) by a 29-gauge needle. Next, each mouse was immediately confined in an observation cage, and the itching behavior was observed under the unattended condition by recording with an 8-mm video camera (SV-K80, Samsung) for 1 hour. Scratching the injection area with the back foot was regarded as the itching behavior, and scratching other portions was not regarded.

(3) Measurement of the Inhibition of Vascular Permeability by Lactic Acid Bacteria It is known that itching-induced areas have increased vascular permeability. This experiment was performed in order to examine whether lactic acid bacteria could efficiently inhibit vascular permeability caused by various compounds. According to the same method as the above-described experiment for measurement of itching inhibitory activity, the drug was administered to the same mice. Next, physiological saline was injected subcutaneously into the back portion of the head of the mice of the normal group, and an itching inducer (50 μg of compound 48/80; Sigma, USA) was injected subcutaneously into the back portion of the head of the mice of the other test group. Next, 0.2 ml of 1% Evans blue solution (Sigma, USA) was injected into the tail vein, and after 1 hour, the mice were euthanized. The skin of the subcutaneously injected area was dissected, and incubated in 1 ml of 1N KOH at 37° C. overnight. On the next day, the incubated skin tissue was mixed with 4 ml of 0.6N phosphoric acid-acetone (5:13) mixture and centrifuged at 3000 rpm for 15 minutes, and the supernatant was collected and measured for absorbance at 620 nm. Inhibition (%) of vascular permeability was calculated using the following equation:

Inhibition (%)={1−[absorbance of area treated with drug and itching inducer−absorbance of area not treated with itching inducer]/[absorbance of area treated with itching inducer−absorbance of area not treated with itching inducer]}×100

(4) Experimental Results

Table 8 below shows the results of measuring the degranulation inhibition rate, itching inhibition rate and capillary permeability inhibition rate of the lactic acid bacteria. In Table 8 below, "CH5" indicates *Lactobacillus curvatus* CH5; "CH11" indicates *Lactobacillus sakei* CH11; "CH15" indicates *Lactobacillus fermentum* CH15; "CH23" indicates *Lactobacillus brevis* CH23; "CH32" indicates *Lactobacillus johnsonii* CH32; "CH38" indicates *Bifidobacterium pseudocatenulatum* CH38; "CH57" indicates *Bifidobacterium longum* CH57; "CH57+CH11" indicates a lactic acid bacteria mixture prepared by mixing *Bifidobacterium longum* CH57 and *Lactobacillus sakei* CH11 in the same amount; "CH57+CH23" indicates a lactic acid bacteria mixture prepared by mixing *Bifidobacterium longum* CH57 and *Lactobacillus brevis* CH23 in the same amount; and "CH57+CH32" indicates a lactic acid bacteria mixture prepared by mixing *Bifidobacterium longum* CH57 and *Lactobacillus johnsonii* CH32 in the same amount.

As shown in Table 8 below, *Lactobacillus curvatus* CH5, *Lactobacillus brevis* CH23, *Lactobacillus johnsonii* CH32 and *Bifidobacterium longum* CH57 effectively inhibited the degranulation of basophils, and *Bifidobacterium longum* CH57 very strongly inhibited itching and vascular permeability. In addition, in comparison with these lactic acid bacteria alone, a mixture of these lactic acid bacteria, particularly a mixture of *Bifidobacterium longum* CH57 and *Lactobacillus brevis* CH23 or a mixture of *Bifidobacterium longum* CH57 and *Lactobacillus johnsonii* CH32 showed higher degranulation inhibition rate, itching inhibition rate and vascular permeability inhibition rate. Thus, it can be seen that these lactic acid bacteria or mixtures thereof can very effectively alleviate allergic atopy, asthma, pharyngitis, chronic dermatitis or the like.

TABLE 8

| | Inhibition (%) | | |
|---|---|---|---|
| Drug | Degranulation | Itching | vascular permeability |
| None | 0 | 2 | 1 |
| CH5 | 53 | 46 | 45 |
| CH11 | 47 | 46 | 45 |
| CH15 | 48 | 42 | 42 |
| CH23 | 54 | 47 | 47 |
| CH32 | 52 | 45 | 46 |
| CH38 | 44 | 45 | 42 |
| CH57 | 55 | 55 | 52 |
| CH57 + CH11 | 59 | 56 | 54 |
| CH57 + CH23 | 63 | 62 | 61 |
| CH57 + CH32 | 61 | 58 | 56 |
| DSCG (disodium cromoglycate) | 62 | 25 | 37 |
| Azelastine | — | 65 | 68 |

5. In Vitro Evaluation of the Anti-Inflammatory Effect and Intestinal Permeability Inhibitory Effect of Lactic Acid Bacteria (1) Isolation of Dendritic Cells and Measurement of Inflammatory Marker Immune cells were isolated from the bone marrow of C57BL/6 mice (male, 20-23 g) by use of RPMI 1640 (containing 10% FBS, 1% antibiotics, 1% glutamax, 0.1% mercaptoethanol). The isolated cells were treated with RBC lysis buffer, washed, dispensed into each well of a 24-well plate, treated with GM-CSF and IL-4 at a ratio of 1:1000, and cultured. On 5 days of the culturing, the medium was replaced with fresh medium, and on 8 days, the cells were collected and used as dendritic cells. Next, the dendritic cells were seeded on a 24-well plate at a density of 0.5×10$^6$ cells/well and treated with lactic acid bacteria (test substance) and the inflammation inducer LPS (lipopolysaccharide) for 2 hours or 24 hours, and then the supernatant and the cells were collected. Using the collected supernatant, the expression levels of IL-10 and IL-12 were measured by an immunoblotting method.

Figure 4:
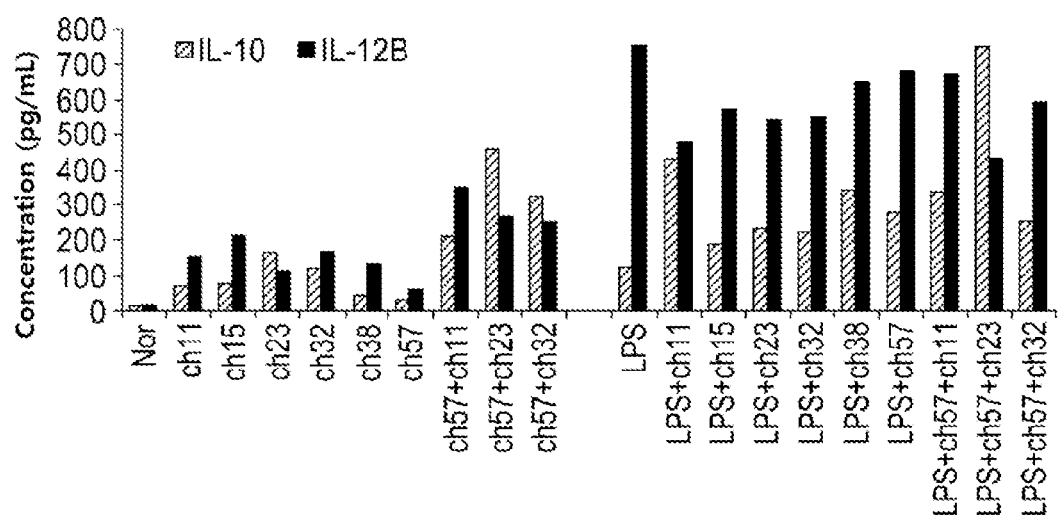
FIG. 4 is a graph showing the effect of lactic acid bacteria, screened in a first experiment of the present invention, on the lipopolysaccharide (LPS)-induced inflammatory response of dendritic cells. The left graph in FIG. 4 shows the effect of lactic acid bacteria on cells not treated with LPS (lipopolysaccharide), and the right graph shows the effect of lactic acid bacteria on cells treated with LPS (lipopolysaccharide).

FIG. 4 is a graph showing the effect of lactic acid bacteria screened in the present invention, on the lipopolysaccharide (LPS)-induced inflammatory response of dendritic cells. The left graph in FIG. 4 shows the effect of lactic acid bacteria on cells not treated with LPS (lipopolysaccharide), and the right graph shows the effect of lactic acid bacteria on cells treated with LPS (lipopolysaccharide). In addition, on the x-axis of FIG. 4, "Nor" indicates a group not treated with the test lactic acid bacteria and the inflammation inducer LPS (lipopolysaccharide); "LPS" indicates a group treated with the inflammation inducer LPS (lipopolysaccharide); "ch11" indicates a group treated with *Lactobacillus sakei* CH11; "ch15" indicates a group treated with *Lactobacillus fermentum* CH15; "ch23" indicates a group treated with *Lactobacillus brevis* CH23; "ch32" indicates a group treated with *Lactobacillus johnsonii* CH32; "ch38" indicates a group treated with *Bifidobacterium pseudocatenulatum* CH38; "ch57" indicates a group treated with *Bifidobacterium longum* CH57; "ch57+ch11" indicates a group treated with a lactic acid bacteria mixture prepared by mixing *Bifidobacterium longum* CH57 and *Lactobacillus sakei* CH11 in the same amount; "ch57+ch23" indicates a group treated with a lactic acid bacteria mixture prepared by mixing *Bifidobacterium longum* CH57 and *Lactobacillus brevis* CH23 in the same amount; and "ch57+ch32" indicates a group treated with a lactic acid bacteria mixture prepared by mixing *Bifidobacterium longum* CH57 and *Lactobacillus johnsonii* CH32 in the same amount.

As shown in FIG. 4, *Lactobacillus sakei* CH11, *Lactobacillus brevis* CH23 and *Lactobacillus johnsonii* CH32 induced IL-10 production of the dendritic cells obtained by differentiation after isolation from the bone marrow, effectively inhibited LPS (lipopolysaccharide)-induced production of IL-12, and also the effects were increased when used in combination with *Bifidobacterium longum* CH57. In particular, a mixture of *Bifidobacterium longum* CH57 and *Lactobacillus brevis* CH23 exhibited the best effect on the inhibition of inflammation. When dendritic cells are controlled, Treg cells (regulatory T cells) can be efficiently controlled. For this reason, the lactic acid bacteria screened in the present invention can effectively alleviate chronic inflammatory diseases such as colitis, autoimmune diseases such as rheumatoid arthritis and the like.

(2) Isolation of Macrophages and Measurement of Inflammatory Marker 6-week-old C57BL/6J male mice (20-23 g) were purchased from RaonBio Co., Ltd. 2 ml of 4% sterile thioglycolate was administered into the abdominal cavity of each mouse, and after 96 hours, the mice were anesthetized, and 8 ml of RPMI 1640 medium was administered into the abdominal cavity of each mouse. After 5 to 10 minutes, the RPMI medium (including macrophages) in the abdominal cavity of the mice was taken out, centrifuged at 1000 rpm for 10 minutes, and then washed twice with RPMI 1640 medium. The macrophages were seeded on a 24-well plate at a density of $0.5 \times 10^6$ cells/well and treated with the test substance lactic acid bacteria and the inflammation inducer LPS (lipopolysaccharide) for 2 hours or 24 hours, and then the supernatant and the cells were collected. The collected cells were homogenized in buffer (Gibco). Using the collected supernatant, the expression levels of cytokines such as TNF-α and IL-1β were measured by an ELISA kit. In addition, using the collected cells, the expression levels of p65 (NF-kappa B), p-p65 (phosphor-NF-kappa B) and β-actin were measured by an immunoblotting method. Specifically, 50 μg of the supernatant was taken and electrophoresed on SDS 10% (w/v) polyacrylamide gel for 1 hour and 30 minutes. The electrophoresed sample was transferred to a nitrocellulose membrane under the conditions of 100 V and 400 mA for 1 hour and 10 minutes. The sample-transferred nitrocellulose membrane was blocked with 5% skim milk for 30 minutes, and then washed three times with PBS-Tween for 5 minutes each time, and incubated with a 1:100 dilution of primary antibody (Santa Cruz Biotechnology, USA) overnight. Next, the membrane was washed three times for 10 minutes each time, and incubated with a 1:1000 dilution of secondary antibody (Santa Cruz Biotechnology, USA) for 1 hour and 20 minutes. Next, the membrane was washed three times for 15 minutes each time, and it was developed by fluorescence and visualized.

Figure 5:
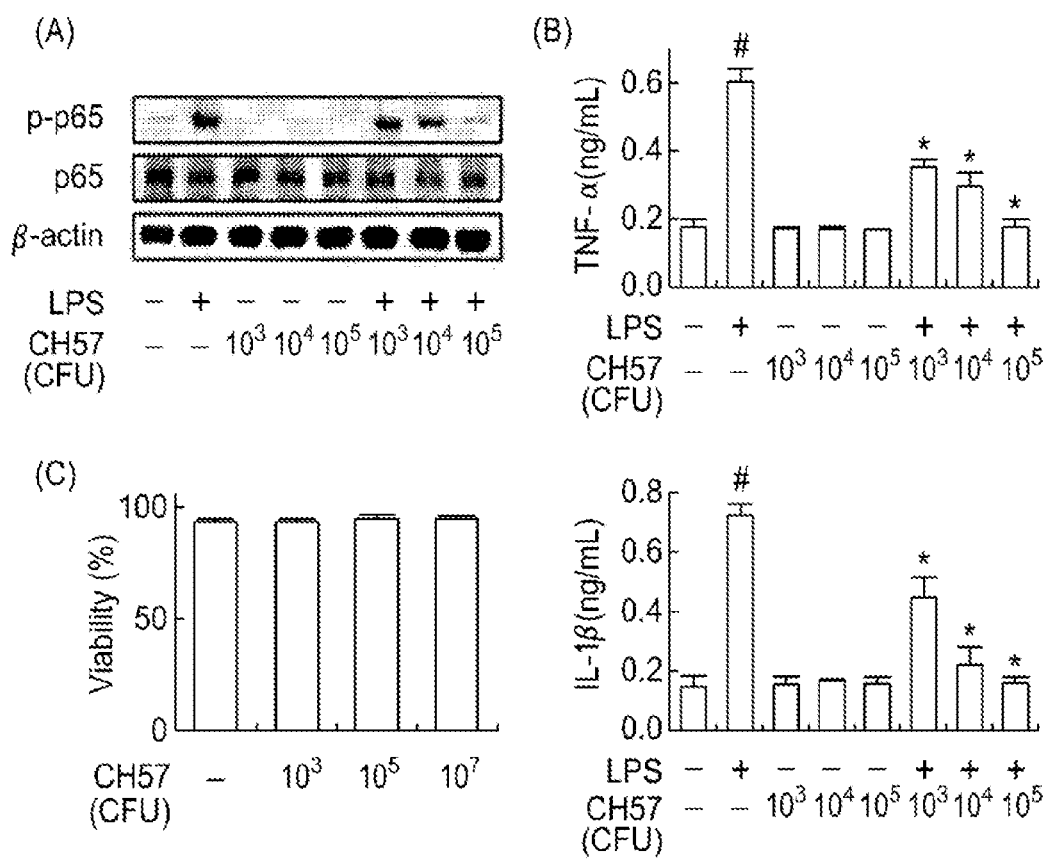
FIG. 5 is a graph showing the effect of *Bifidobacterium longum* CH57 on the LPS (lipopolysaccharide)-induced inflammatory response of macrophages in a first experiment of the present invention.

FIG. 5 is a graph showing the effect of *Bifidobacterium longum* CH57 on the LPS (lipopolysaccharide)-induced inflammatory response of macrophages. As shown in FIG. 5, *Bifidobacterium longum* CH57 effectively inhibited the LPS (lipopolysaccharide)-induced inflammatory response.

(3) Isolation of T Cells from Spleen and Measurement of Differentiation into Th17 Cells or Treg Cells Spleen was separated from C56BL/6J mice, crushed suitably, and suspended in 10% FCS-containing RPMI 1640 medium, and CD4 T cells were isolated therefrom using a CD4 T cell isolation kit (MiltenyiBiotec, Bergisch Gladbach, Germany). The isolated CD4 T cells were seeded in a 12-well plate at a density of $5 \times 10^5$ cells/well, and anti-CD3 (1 μg/ml, MiltenyiBiotec, Bergisch Gladbach, Germany) and anti-CD28 (1 μg/ml, MiltenyiBiotec, Bergisch Gladbach, Germany) were added thereto, or anti-CD3 (1 μg/ml, MiltenyiBiotec, Bergisch Gladbach, Germany), anti-CD28 (1 μg/ml, MiltenyiBiotec, Bergisch Gladbach, Germany), recombinant IL-6 (20 ng/ml, MiltenyiBiotec, Bergisch Gladbach, Germany) and recombinant transforming growth factor beta (1 ng/ml, MiltenyiBiotec, Bergisch Gladbach, Germany) were added. While the cells were cultured, $1 \times 10^3$ or $1 \times 10^5$ CFU of the lactic acid bacteria were added thereto, and the cells were cultured for 4 days. Next, the cells of the culture were stained with anti-FoxP3 or anti-IL-17A antibody, and the distribution of Th17 and Treg cells was analyzed using a FACS (fluorescence-activated cell sorting) system (C6 Flow Cytometer® System, San Jose, Calif., USA).

Figure 6:
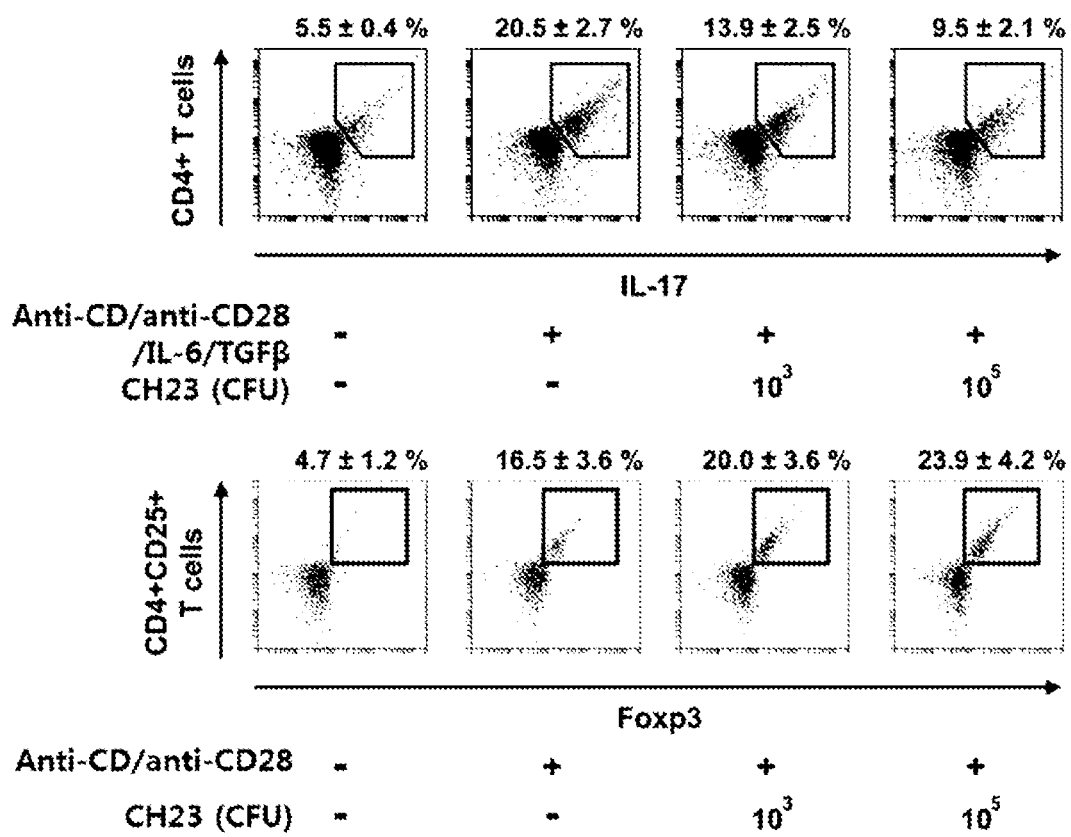
FIG. 6 shows the results of analyzing the effect of *Lactobacillus brevis* CH23 on the differentiation of T cells (isolated from spleen) into Th17 cells or Treg cells by a fluorescence-activated cell sorting system in a first experiment of the present invention.

FIG. 6 shows the results of analyzing the effect of *Lactobacillus brevis* CH23 on the differentiation of T cells (isolated from spleen) into Th17 cells or Treg cells by a fluorescence-activated cell sorting system. As shown in FIG. 6, *Lactobacillus brevis* CH23 inhibited the differentiation of T cells into Th17 cells (T helper 17 cells) and promoted the differentiation of T cells into Treg cells. These results suggest that *Lactobacillus brevis* CH23 can effectively alleviate inflammatory diseases such as colitis and arthritis.

(4) Measurement of the Effect of Lactic Acid Bacteria on ZO-1 Protein Expression of CaCO2 Cells Caco2 cells obtained from the Korean Cell Line Bank were cultured in RPMI 1640 medium for 48 hours, and then the cultured Caco2 cells were dispensed into a 12-well plate at a density of $2 \times 10^6$ cells/well. Next, each well was treated with 1 μg of LPS (lipopolysaccharide) alone or a combination of 1 μg of LPS (lipopolysaccharide) and $1 \times 10^3$ CFU or $1 \times 10^5$ CFU of lactic acid bacteria, and then incubated for 24 hours. Next, the cultured cells were collected from each well, and the expression level of tight junction protein ZO-1 was measured by an immunoblotting method.

Figure 7:
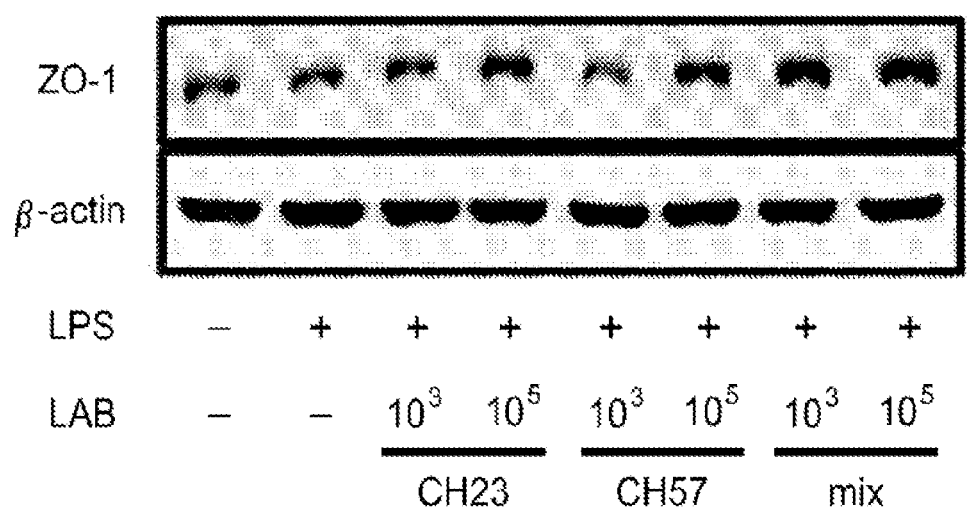
FIG. 7 shows the results of analyzing the effect of *Lactobacillus brevis* CH23, *Bifidobacterium longum* CH57 or a mixture thereof on ZO-1 protein expression in CaCO2 cells in a first experiment of the present invention.

FIG. 7 shows the results of analyzing the effect of *Lactobacillus brevis* CH23, *Bifidobacterium longum* CH57 or a mixture thereof on ZO-1 protein expression of CaCO2 cells. In FIG. 7, "CH23" indicates *Lactobacillus brevis* CH23; "CH57" indicates *Bifidobacterium longum* CH57; "mix" indicates a lactic acid bacteria mixture prepared by mixing *Bifidobacterium longum* CH57 and *Lactobacillus johnsonii* CH32 in the same amount. As shown in FIG. 7, treatment with *Lactobacillus brevis* CH23 and *Bifidobacterium longum* CH57 increased the expression of tight junction protein ZO-1, and treatment with a mixture of *Bifido*-

*bacterium longum* CH57 and *Lactobacillus johnsonii* CH32 synergistically increased the expression of tight junction protein ZO-1. When the expression of tight junction protein increases, in vivo penetration of toxic substances can be blocked, thereby prevents the worsening of colitis, arthritis and liver injury.

6. In Vivo Evaluation of the Anti-Inflammatory and Colitis-Alleviating Effects of Lactic Acid Bacteria (1) Test Animals 5-Week-old C57BL/6 male mice (24-27 g) were purchased from OrientBio, and housed under controlled environmental conditions (humidity: 50±10%, temperature: 25±2° C., 12-hr light/12-hr dark cycle), and then used in the experiment. As feed, standard experimental feed (Samyang, Korea) was used, and the animals had access to drinking water ad libitum. In all the experiments, one group consisted of 6 animals.

(2) Colitis Induction by TNBS and Sample Administration

One group of the test animals was used as a normal group, and the test animals of the other groups were treated with 2,4,6-trinitrobenzenesulfonic acid (TNBS) to induce acute colitis. Specifically, the test animals were lightly anesthetized with ether, and then a mixture solution of 2.5 g of TNBS (2,4,6-trinitrobenzene sulfonic acid) and 100 ml of 50% ethanol was administered into the colon through the anal in an amount of 0.1 ml each time by use of a 1-ml round-tip syringe, lifted vertically and maintained for 30 seconds, thereby inducing inflammation. On the other hand, the normal group was administered orally with 0.1 ml of saline. On the next day, the lactic acid bacteria or the lactic acid bacteria mixture as a test sample was suspended in saline and administered orally to each mouse in an amount of $2.0 \times 10^9$ CFU, once a day for three days. On the next day following the end of sample administration, the animals were killed with carbon dioxide, and a colon portion ranging from the cecum to the site just before the anus was dissected and used. Meanwhile, the test animals of the normal group were orally administered with saline alone instead of the lactic acid bacteria. In addition, the test animals of the negative control group were orally administered with saline alone instead of the lactic acid bacteria after the induction of colitis by TNBS. Furthermore, the test animals of the positive control group were orally administered with 50 mg/kg of sulfasalazine, which is a drug for treating colitis, instead of the lactic acid bacteria.

(3) Macroscopic Analysis of Colon

The length and appearance of the dissected colon were observed, and the appearance was analyzed by scoring according to the criteria (Hollenbach et al., 2005, Criteria for Degree of Colitis) shown in Table 9 below. After complete removal of colon contents, the colon tissue was washed with saline. A portion of the washed colon tissue was fixed with 4% formaldehyde solution in order to use it as a pathological tissue sample, and the remainder was freeze-stored at −80° C. for molecular biological analysis.

TABLE 9

| Macroscopic score | Criteria |
| --- | --- |
| 0 | Any ulcer and inflammation are not found. |
| 1 | Edema without bleeding is found. |
| 2 | Ulcer with edema is found. |
| 3 | Ulcer and inflammation are found at only one site. |
| 4 | Ulcer and inflammation are found at two or more sites. |
| 5 | Ulcer has an increased size of 2 cm or more. |

(4) Measurement of Myeloperoxidase (MPO) Activity 100 mg of colon tissue was homogenized in 200 μl of 10 mM potassium phosphate buffer (pH 7.0) containing 0.5% hexadecyl trimethyl ammonium bromide. The homogenized tissue was centrifuged at 10,000×g and 4° C. for 10 minutes, and the supernatant was collected. 50 μl of the supernatant was added to 0.95 ml of a reaction solution (containing 1.6 mM tetramethyl benzidine and 0.1 mM $H_2O_2$) and allowed to react at 37° C., and the absorbance at 650 nm was measured at various time points during the reaction. To calculate myeloperoxidase (MPO) activity, 1 μmol/ml of peroxide produced by the reaction was used as 1 unit.

(5) Measurement of Inflammatory Marker

Using a Western blotting method, inflammatory markers such as p-p65, p65, iNOS, COX-2 and β-actin were measured. Specifically, according to the same method as the experiment for measurement of myeloperoxidase (MPO) activity, a supernatant was obtained. 50 μg of the supernatant was taken and electrophoresed on SDS 10% (w/v) polyacrylamide gel for 1 hour and 30 minutes. The electrophoresed sample was transferred to a nitrocellulose membrane under the conditions of 100 V and 400 mA for 1 hour and 10 minutes. The sample-transferred nitrocellulose membrane was blocked with 5% skim milk for 30 minutes, and then washed three times with PBS-Tween for 5 minutes each time, and incubated with a 1:100 dilution of primary antibody (Santa Cruz Biotechnology, USA) overnight. Next, the membrane was washed three times for 10 minutes each time, and incubated with a 1:1000 dilution of secondary antibody (Santa Cruz Biotechnology, USA) for 1 hour and 20 minutes. Next, the membrane was washed three times for 15 minutes each time, and it was developed by fluorescence and visualized.

In addition, inflammation-related cytokines such as TNF-α, IL-1β and the like were measured using an ELISA kit.

(6) Experimental Results

Figure 8:
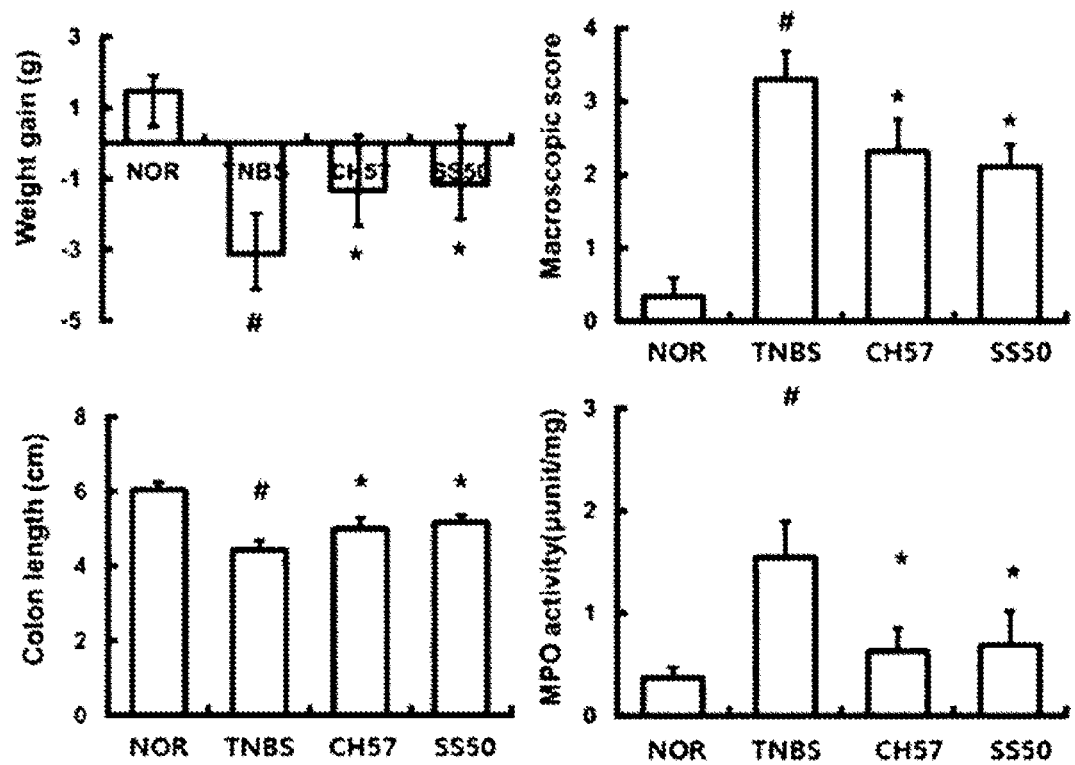
FIG. 8 shows the colon appearance or myeloperoxidase (MPO) activity indicating the effect of *Bifidobacterium longum* CH57 on model animals having acute colitis induced by TNBS, in a first experiment of the present invention.
Figure 9:
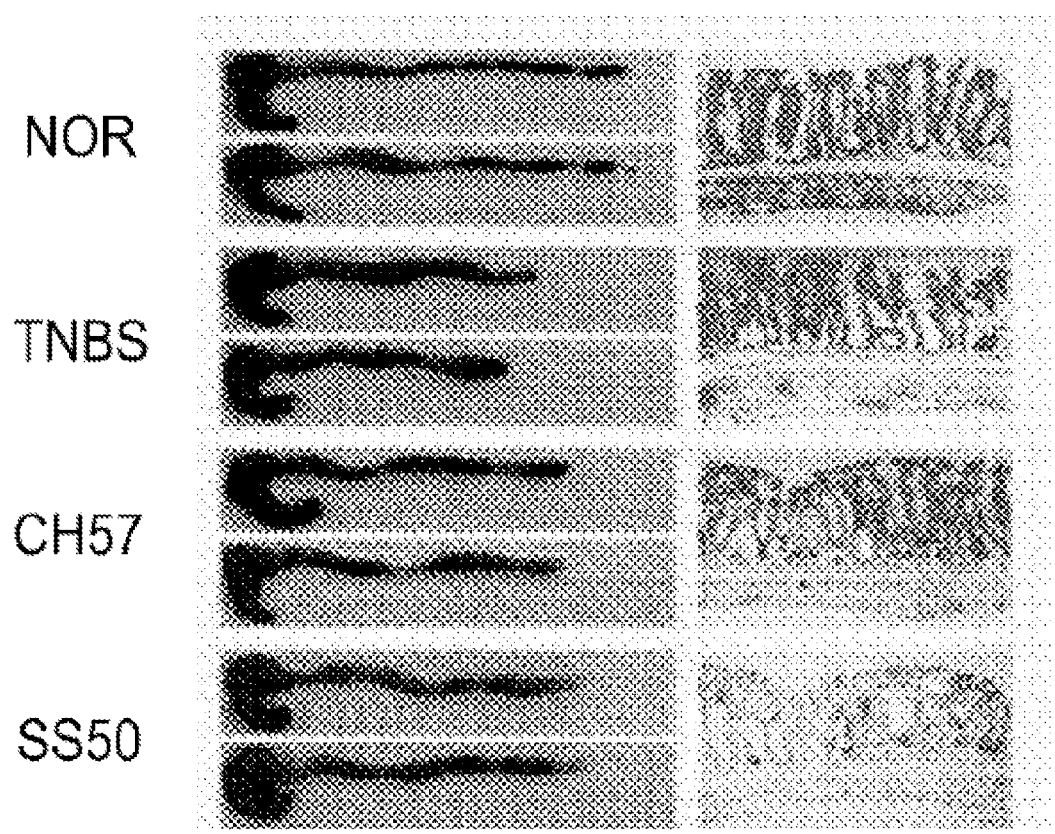
FIG. 9 depicts histological images showing the effect of *Bifidobacterium longum* CH57 on model animals having acute colitis induced by TNBS, in a first experiment of the present invention.
Figure 10:
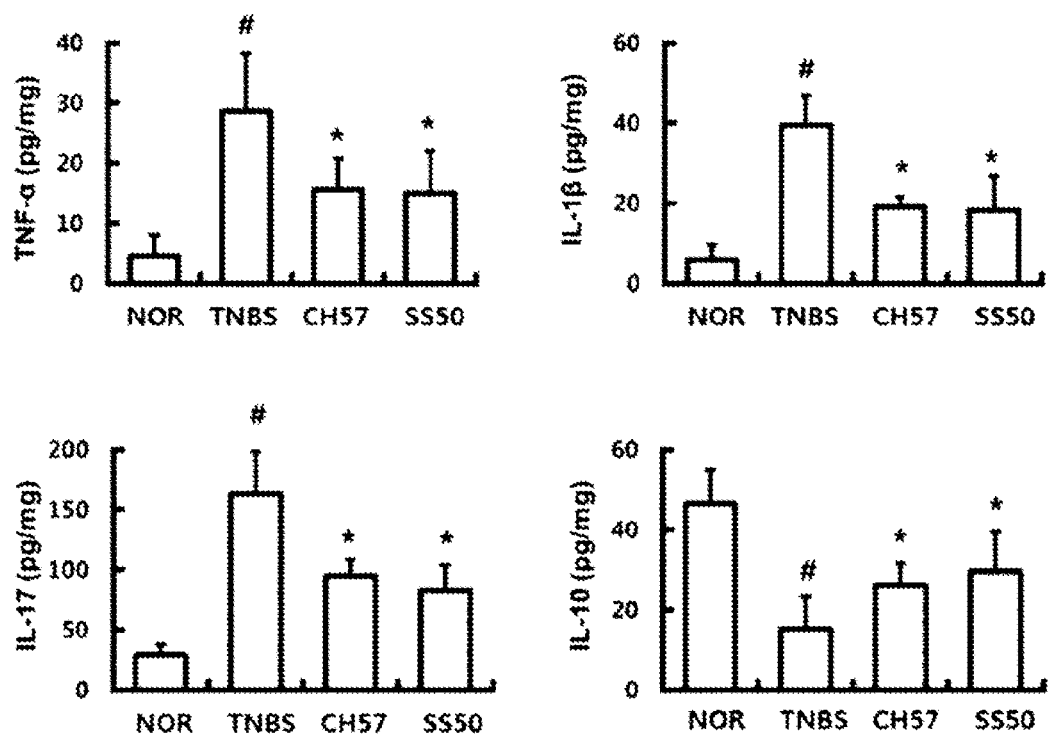
FIG. 10 shows inflammation-related cytokine levels indicating the effect of *Bifidobacterium longum* CH57 on model animals having acute colitis induced by TNBS, in a first experiment of the present invention.

FIG. 8 shows the colon appearance or myeloperoxidase (MPO) activity indicating the effect of *Bifidobacterium longum* CH57 on model animals having acute colitis induced by TNBS; FIG. 9 depicts histological images of colon, which show the effect of *Bifidobacterium longum* CH57 on model animals having acute colitis induced by TNBS; and FIG. 10 shows inflammation-related cytokine levels indicating the effect of *Bifidobacterium longum* CH57 on model animals having acute colitis induced by TNBS. In FIGS. 8 to 10, "NOR" indicates a normal group; "TNBS" indicates a negative control group; "CH57" indicates a group administered with *Bifidobacterium longum* CH57; and "SS50" indicates a group administered with sulfasalazine. As shown in FIGS. 8 to 10, *Bifidobacterium longum* CH57 effectively alleviated colitis in view of the weight of the model animals having TNBS-induced acute colitis, the colitis markers, the colon length, myeloperoxidase (MPO) activity, and the like, and showed a better effect on the alleviation of colitis than sulfasalazine. In addition, *Bifidobacterium longum* CH57 inhibited inflammatory cytokine production and increased the production of the anti-inflammatory cytokine IL-10 in the model animals having TNBS-induced acute colitis.

Figure 11:
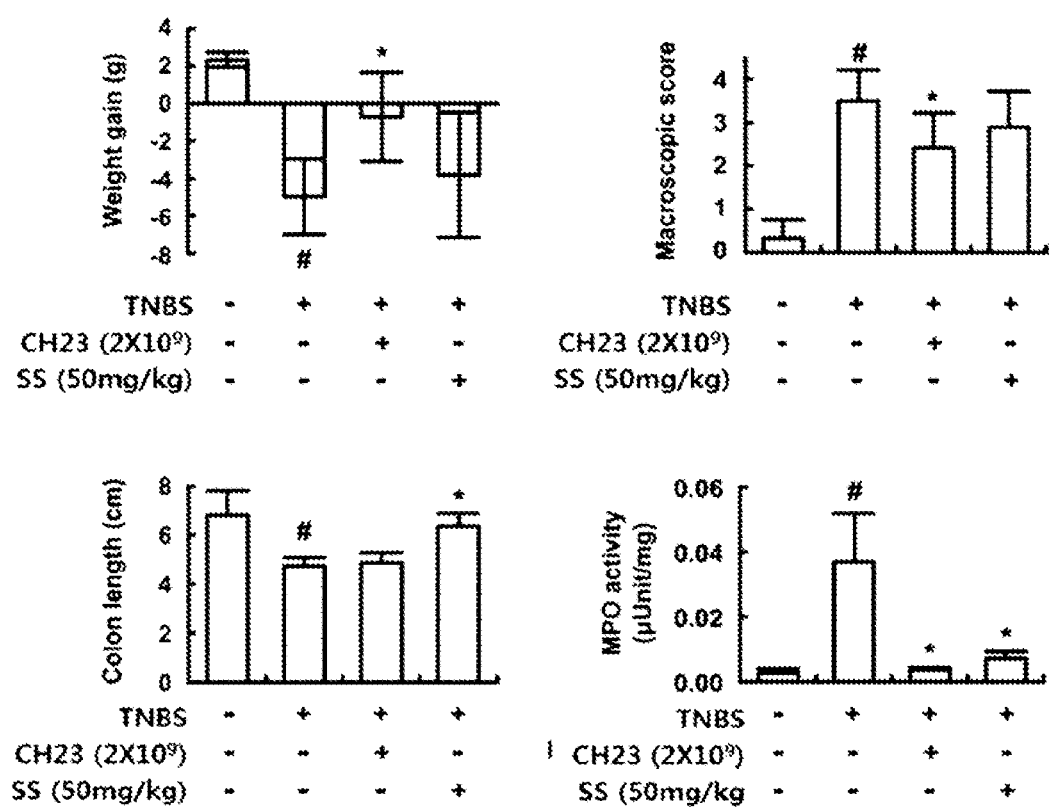
FIG. 11 shows the colon appearance or myeloperoxidase (MPO) activity indicating the effect of *Lactobacillus brevis* CH23 on model animals having acute colitis induced by TNBS, in a first experiment of the present invention.
Figure 12:
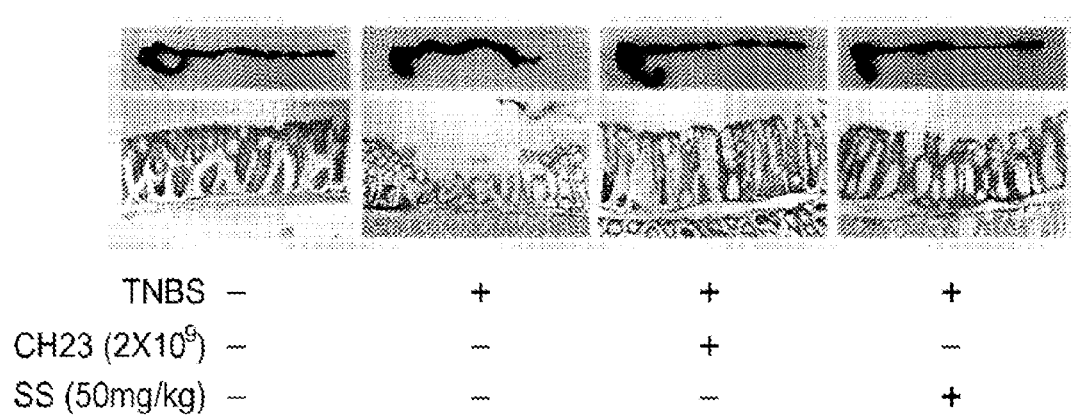
FIG. 12 depicts histological images of colon, which show the effect of *Lactobacillus brevis* CH23 on model animals having acute colitis induced by TNBS, in a first experiment of the present invention.
Figure 13:
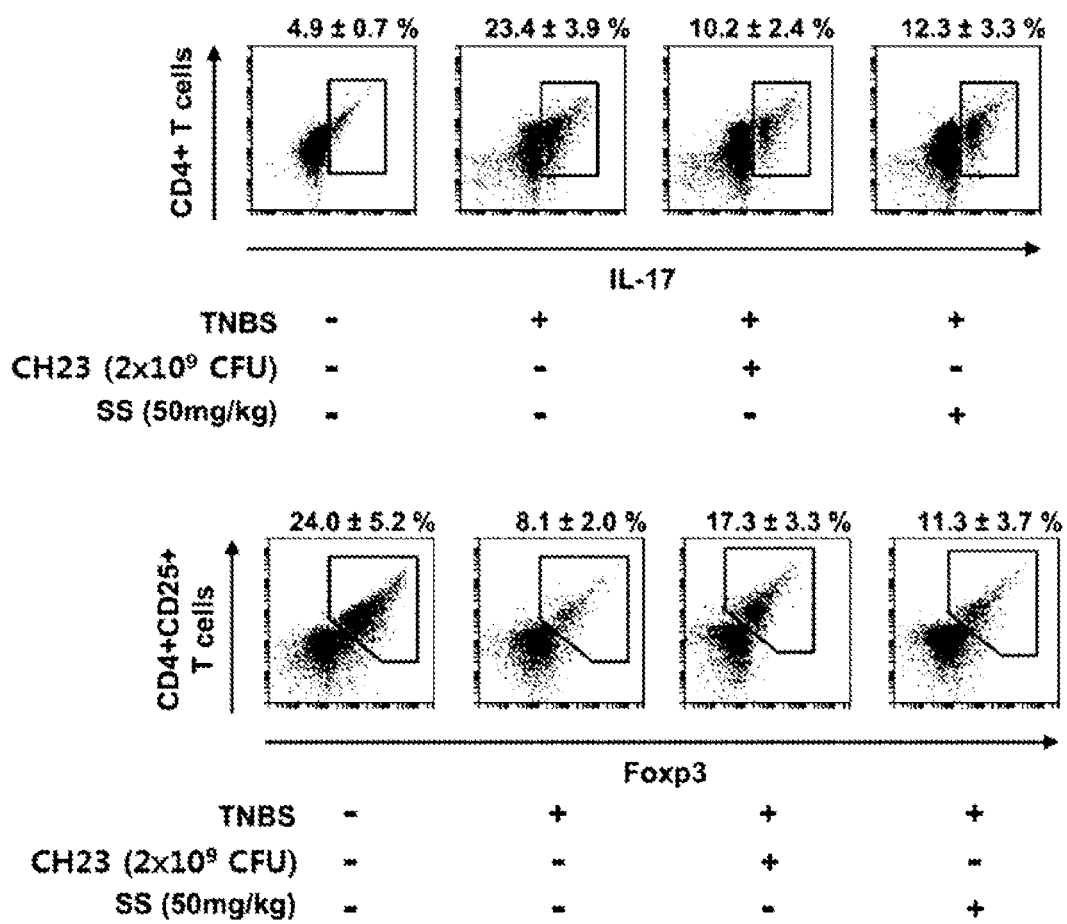
FIG. 13 shows T-cell differentiation patterns indicating the effect of *Lactobacillus brevis* CH23 on model animals having acute colitis induced by TNBS, in a first experiment of the present invention.
Figure 14:
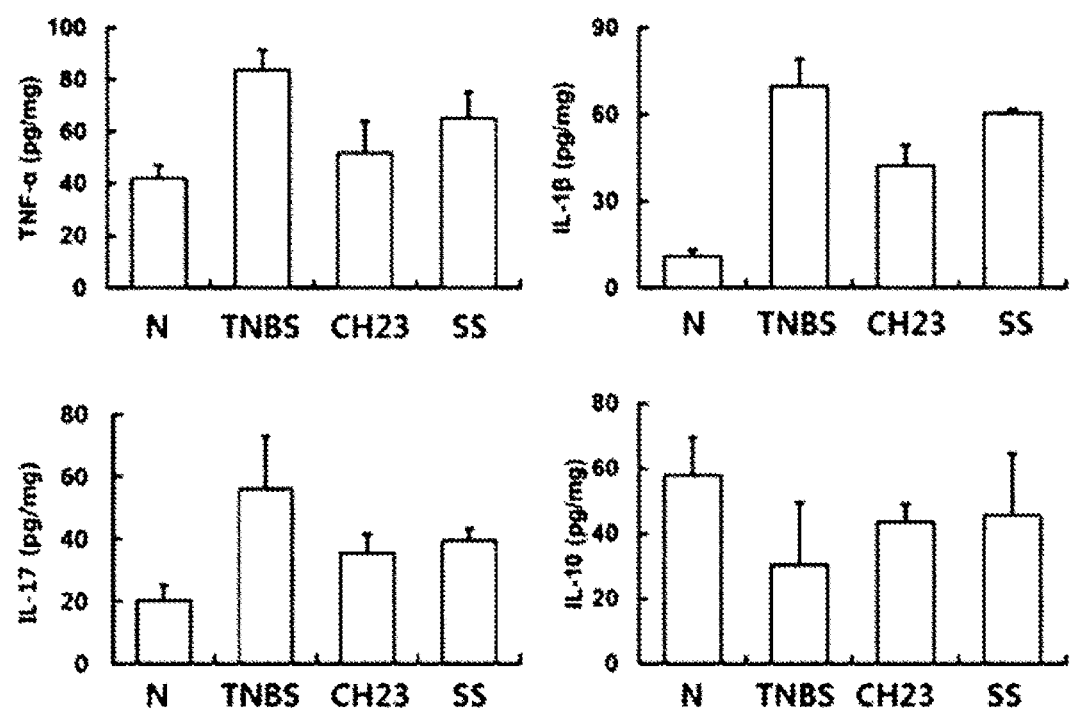
FIG. 14 shows inflammation-related cytokine levels indicating the effect of *Lactobacillus brevis* CH23 on model animals having acute colitis induced by TNBS, in a first experiment of the present invention.

FIG. 11 shows the colon appearance or myeloperoxidase (MPO) activity indicating the effect of *Lactobacillus brevis* CH23 on model animals having acute colitis induced by TNBS; FIG. 12 depicts histological images of colon, which show the effect of *Lactobacillus brevis* CH23 on model animals having acute colitis induced by TNBS; FIG. 13 shows T-cell differentiation patterns indicating the effect of *Lactobacillus brevis* CH23 on model animals having acute colitis induced by TNBS; and FIG. 14 shows inflammation-related cytokine levels indicating the effect of *Lactobacillus brevis* CH23 on model animals having acute colitis induced by TNBS. In FIGS. 11 to 14, "N" indicates a normal group; "TNBS" indicates a negative control group; "CH23" indicates a group administered with *Lactobacillus brevis* CH23; and "SS" indicates a group administered with sulfasalazine. As shown in FIGS. 11 to 14, *Lactobacillus brevis* CH23 effectively alleviated colitis in view of the weight of the model animals having TNBS-induced acute colitis, the colitis markers, the colon length, myeloperoxidase (MPO) activity and the like, and showed a better effect on the alleviation of colitis than sulfasalazine. In addition, *Lactobacillus brevis* CH23 inhibited the differentiation of T cells into Th17 cells and induced the differentiation of T cells into Treg cells in the model animals having TNBS-induced acute colitis. Furthermore, *Lactobacillus brevis* CH23 inhibited inflammatory cytokine production and increased the production of the anti-inflammatory cytokine IL-10 in the model animals having TNBS-induced acute colitis.

Figure 15:
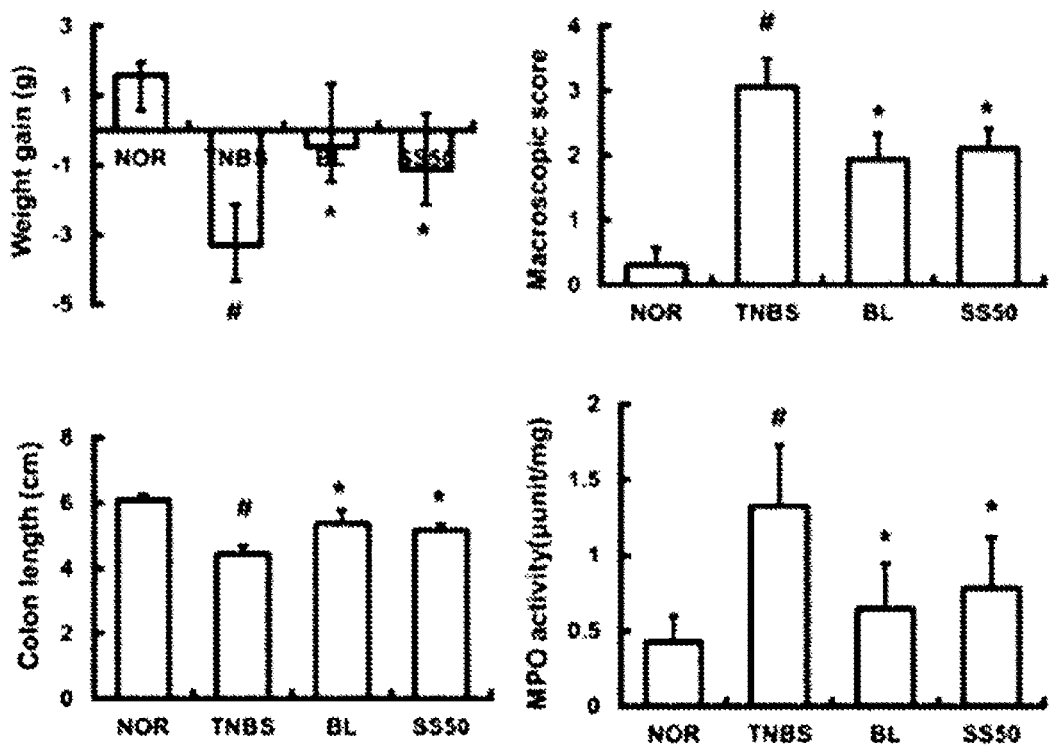
FIG. 15 shows the colon appearance or myeloperoxidase (MPO) activity indicating the effect of a mixture of *Bifidobacterium longum* CH57 and *Lactobacillus brevis* CH23 on model animals having acute colitis induced by TNBS, in a first experiment of the present invention.
Figure 16:
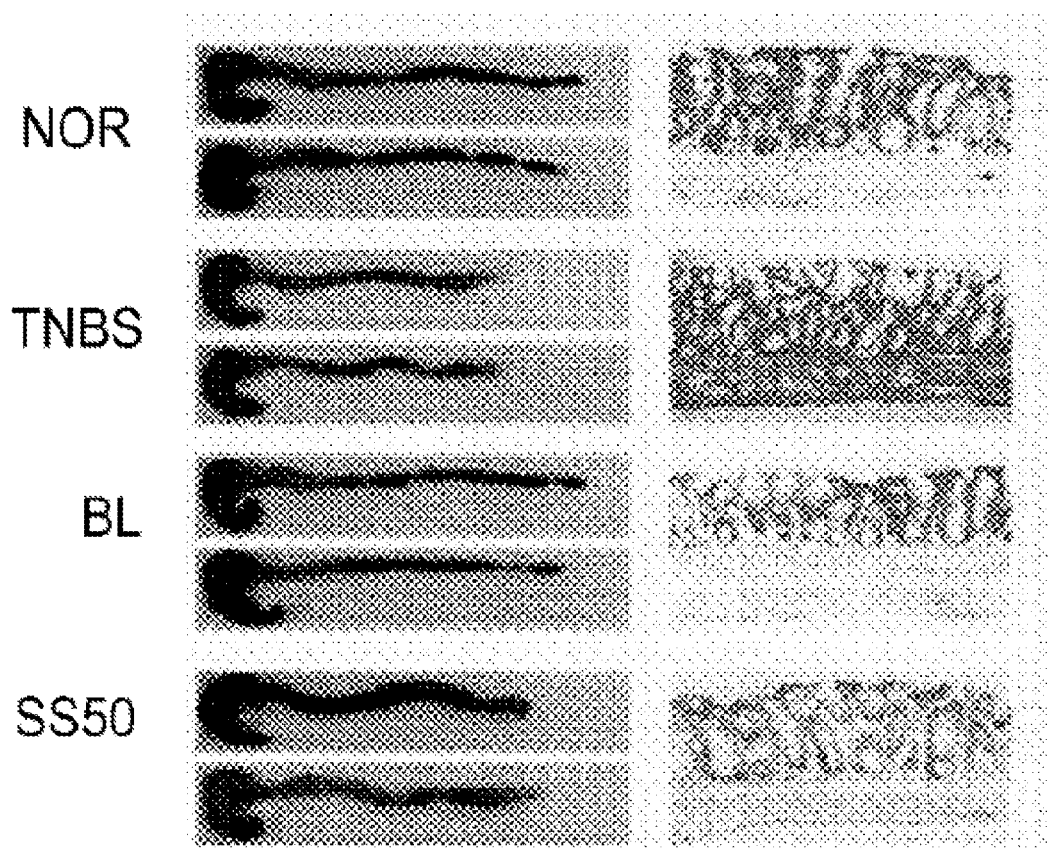
FIG. 16 depicts histological images showing the effect of a mixture of *Bifidobacterium longum* CH57 and *Lactobacillus brevis* CH23 on model animals having acute colitis induced by TNBS, in a first experiment of the present invention.
Figure 17:
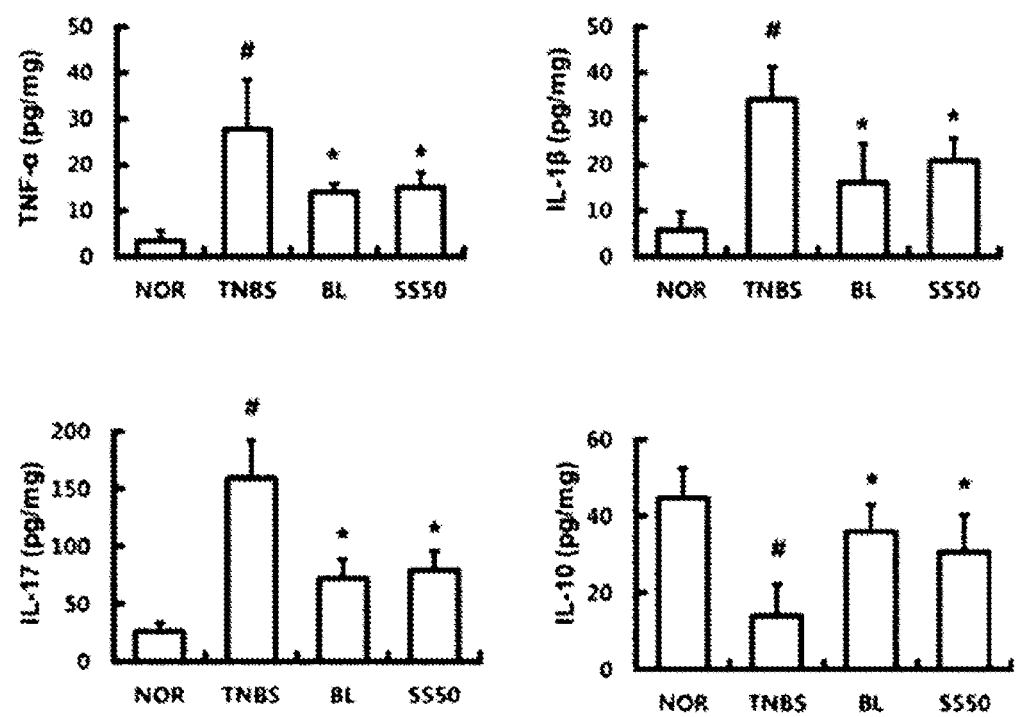
FIG. 17 shows inflammation-related cytokine levels indicating the effect of a mixture of *Bifidobacterium longum* CH57 and *Lactobacillus brevis* CH23 on model animals having acute colitis induced by TNBS, in a first experiment of the present invention.

FIG. 15 shows the colon appearance or myeloperoxidase (MPO) activity indicating the effect of a mixture of *Bifidobacterium longum* CH57 and *Lactobacillus brevis* CH23 on model animals having acute colitis induced by TNBS; FIG. 16 depicts histological images showing the effect of a mixture of *Bifidobacterium longum* CH57 and *Lactobacillus brevis* CH23 on model animals having acute colitis induced by TNBS; and FIG. 17 shows inflammation-related cytokine levels indicating the effect of a mixture of *Bifidobacterium longum* CH57 and *Lactobacillus brevis* CH23 on model animals having acute colitis induced by TNBS. In FIGS. 15 to 17, "NOR" indicates a normal group; "TNBS" indicates a negative control group; "BL" indicates a group administered with a lactic acid bacteria mixture prepared by mixing *Bifidobacterium longum* CH57 and *Lactobacillus brevis* CH23 in the same amount; and "SS50" indicates a group administered with sulfasalazine. As shown in FIGS. 15 to 17, a lactic acid bacteria mixture of *Bifidobacterium longum* CH57 and *Lactobacillus brevis* CH23 significantly improved effects against the reduced weight of the model animals having TNBS-induced acute colitis, increased colitis marker levels, shortened colon lengths and increased myeloperoxidase (MPO) activity, and the effect thereof on the alleviation of colitis was significantly better than that of sulfasalazine. In addition, the lactic acid bacteria mixture of *Bifidobacterium longum* CH57 and *Lactobacillus brevis* CH23 significantly inhibited inflammatory cytokine production and dramatically increased the production of anti-inflammatory cytokine IL-10 in the model animals having TNBS-induced acuter colitis.

7. In Vivo Evaluation of the Obesity-Reducing and Anti-Inflammatory Effects of Lactic Acid Bacteria (1) Experimental Method A total of 24 C57BL6/J mice were purchased from RaonBio Co., Ltd., and acclimated with chow diet (Purina) under the conditions of temperature of 20±2° C., humidity of 50±10% and 12-hr light/12-hr dark cycle for 1 week. Next, the test animals were divided into three groups (LFD, HFD, and HFD+BL), each consisting of 8 animals, the LFD group was fed with a normal diet (LFD, 10% of calories from fat; Research, NJ, USA) for 4 weeks, and the HFD group and the HFD+BL group were fed with a high-fat diet (HFD, 60% of calories from fat; Research, NJ, USA) for 4 weeks. Next, the LFD group was orally administered with PBS while fed with the normal diet for 4 weeks. Furthermore, the HFD group was orally administered with PBS while fed with the high-fat diet for 4 weeks. In addition, the HFD+BL group was orally administered with a PBS suspension of $2\times10^9$ CFU of a lactic acid bacteria mixture while fed with the high-fat diet for 4 weeks. The lactic acid bacteria mixture was prepared by mixing *Bifidobacterium longum* CH57 and *Lactobacillus brevis* CH23 in the same amount.

(2) Analysis of the Anti-Obesity Effect and Anti-Inflammatory Effect of Lactic Acid Bacteria Mixture The anti-obesity effect of the lactic acid bacteria mixture was analyzed through weight change. In addition, the anti-inflammatory effect of the lactic acid bacteria mixture was analyzed using the same method as that used in the experiment on the model animals having TNBS-induced acute colitis.

(3) Experimental Results

Figure 18:
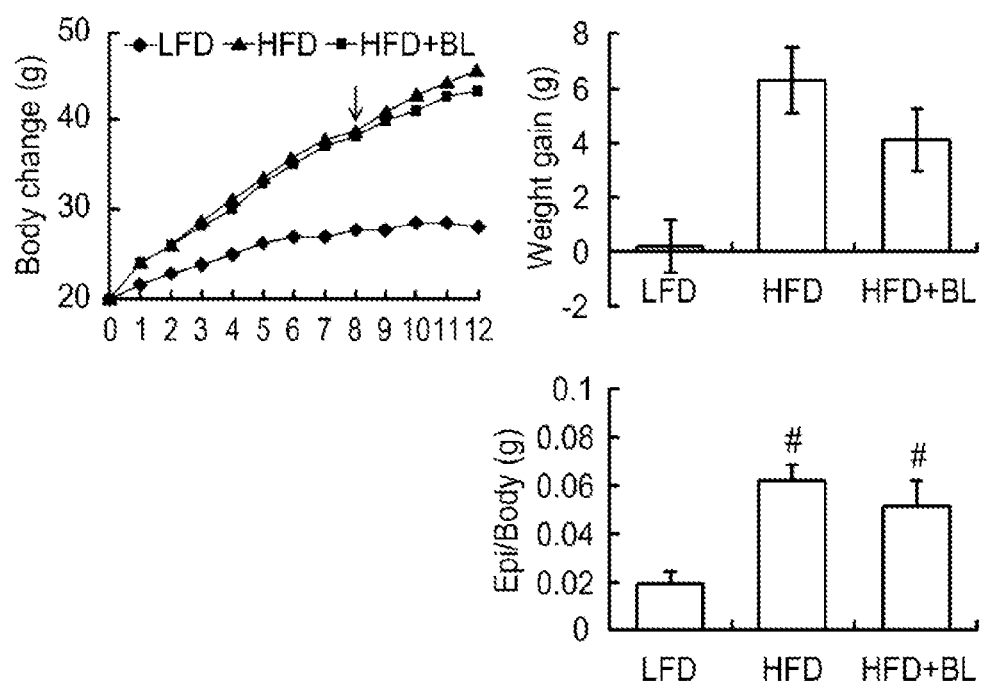
FIG. 18 shows weight changes indicating the effect of a mixture of *Bifidobacterium longum* CH57 and *Lactobacillus brevis* CH23 on obesity-induced model animals, in a first experiment of the present invention.
Figure 19:
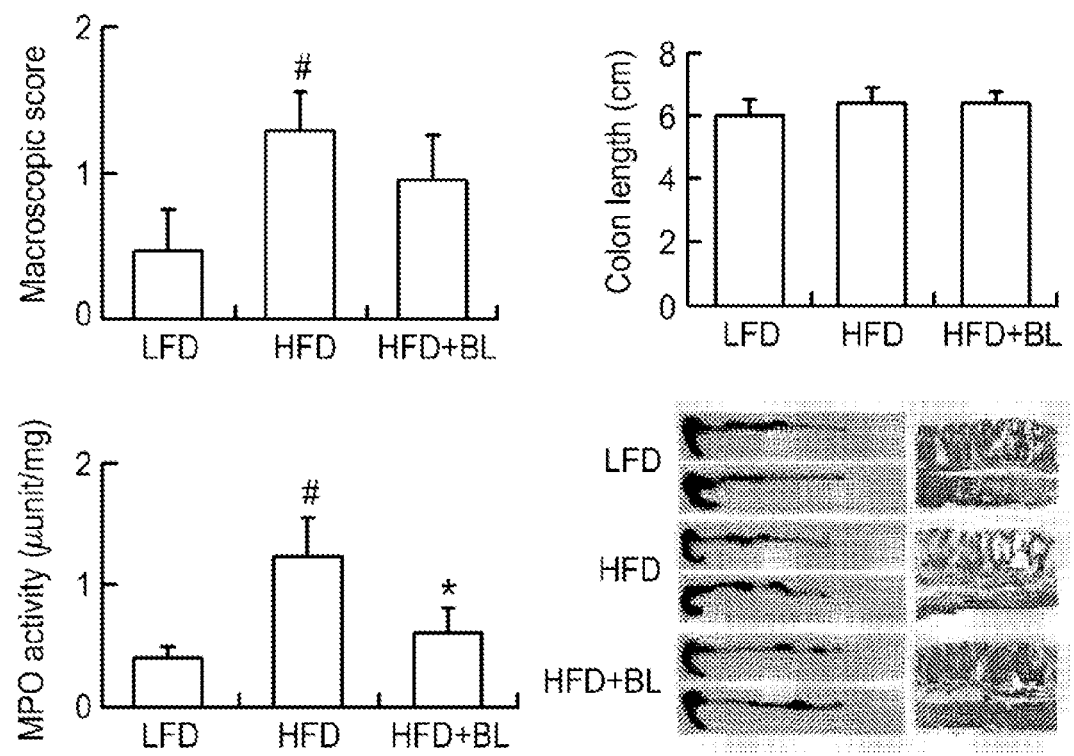
FIG. 19 shows the appearance of colon, myeloperoxidase (MPO) activity, histological images of colon, and the like indicating the effect of a mixture of *Bifidobacterium longum* CH57 and *Lactobacillus brevis* CH23 on obesity-induced model animals, in a first experiment of the present invention.
Figure 20:
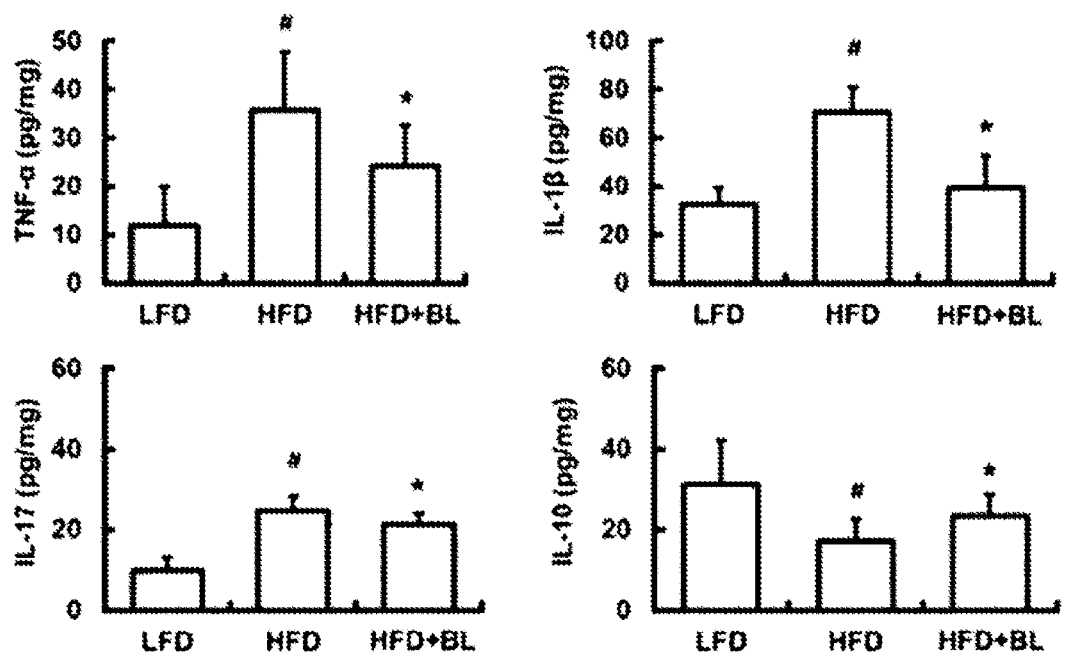
FIG. 20 shows inflammation-related cytokine levels indicating the effect of a mixture of *Bifidobacterium longum* CH57 and *Lactobacillus brevis* CH23 on obesity-induced model animals, in a first experiment of the present invention.
Figure 21:
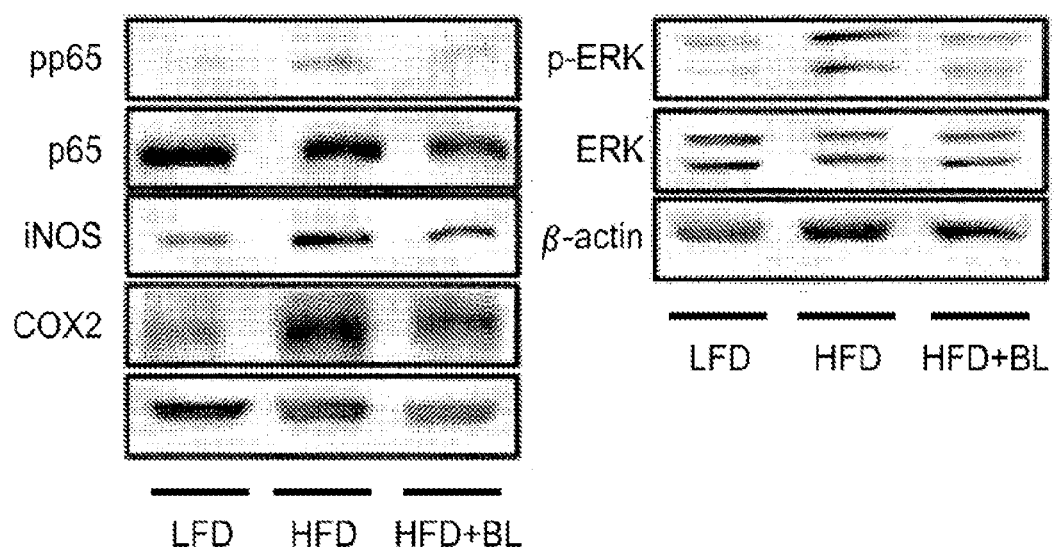
FIG. 21 shows inflammatory response markers indicating the effect of a mixture of *Bifidobacterium longum* CH57 and *Lactobacillus brevis* CH23 on obesity-induced model animals, in a first experiment of the present invention.

FIG. 18 shows weight changes indicating the effect of a mixture of *Bifidobacterium longum* CH57 and *Lactobacillus brevis* CH23 on obesity-induced model animals; FIG. 19 shows the appearance of colon, myeloperoxidase (MPO) activity, histological images of colon and the like, which indicate the effect of a mixture of *Bifidobacterium longum* CH57 and *Lactobacillus brevis* CH23 on obesity-induced model animals; FIG. 20 shows inflammation-related cytokine levels indicating the effect of a mixture of *Bifidobacterium longum* CH57 and *Lactobacillus brevis* CH23 on obesity-induced model animals; and FIG. 21 shows inflammatory response markers indicating the effect of a mixture of *Bifidobacterium longum* CH57 and *Lactobacillus brevis* CH23 on obesity-induced model animals. As shown in FIGS. 18 to 21, the lactic acid bacteria mixture of *Bifidobacterium longum* CH57 and *Lactobacillus brevis* CH23 greatly reduced the increased weight, increased colitis marker levels and increased myeloperoxidase (MPO) activity of the model animals having obesity induced by the high-fat diet, and inhibited the development of colitis. In addition, the lactic acid bacteria mixture of *Bifidobacterium longum* CH57 and *Lactobacillus brevis* CH23 greatly inhibited inflammatory cytokine production and increased the production of anti-inflammatory cytokine IL-10 in the model animals having obesity induced by the high-fat diet.

II. Second Experiment for Screening of Lactic Acid Bacteria and Evaluation of the Effects Thereof 1. Isolation and Identification of Lactic Acid Bacteria (1) Isolation of Lactic Acid Bacteria from Kimchi Each of Chinese cabbage kimchi, radish kimchi and green onion kimchi was crushed, and the crushed liquid was suspended in MRS liquid medium (MRS Broth; Difco, USA). Next, the supernatant was collected, transferred to MRS agar medium (Difco, USA), and cultured anaerobically at 37° C. for about 48 hours, and then *Bifidobacterium longum* strains that formed colonies were separated according to shape.

(2) Isolation of Lactic Acid Bacteria from Human Feces

Human feces were suspended in GAM liquid medium (GAM broth; Nissui Pharmaceutical, Japan). Next, the supernatant was collected, transferred to BL agar medium (Nissui Pharmaceutical, Japan) and cultured anaerobically at 37° C. for about 48 hours, and then *Bifidobacterium* sp. strains that formed colonies were isolated.

(3) Identification of Screened Lactic Acid Bacteria

The gram-staining characteristics, physiological characteristics and 16S rDNA sequences of the strains isolated from kimchi or human feces were analyzed to identify the species of the strains, and names were given to the strains. Table 10 below the control numbers and strain names of the lactic acid bacteria isolated from Chinese cabbage kimchi, radish kimchi and green onion kimchi, and Table 11 below shows the control numbers and strain names of the lactic acid bacteria isolated from human feces.

TABLE 10

| Control No. | Strain name |
|---|---|
| 1 | Lactobacillus plantarum LC1 |
| 2 | Lactobacillus plantarum LC2 |
| 3 | Lactobacillus plantarum LC3 |
| 4 | Lactobacillus plantarum LC4 |
| 5 | Lactobacillus plantarum LC5 |
| 6 | Lactobacillus plantarum LC6 |
| 7 | Lactobacillus plantarum LC7 |
| 8 | Lactobacillus plantarum LC8 |
| 9 | Lactobacillus plantarum LC9 |
| 10 | Lactobacillus plantarum LC10 |
| 11 | Lactobacillus plantarum LC11 |
| 12 | Lactobacillus plantarum LC12 |
| 13 | Lactobacillus plantarum LC13 |
| 14 | Lactobacillus plantarum LC14 |
| 15 | Lactobacillus plantarum LC15 |
| 16 | Lactobacillus plantarum LC16 |
| 17 | Lactobacillus plantarum LC17 |
| 18 | Lactobacillus plantarum LC18 |
| 19 | Lactobacillus plantarum LC19 |
| 20 | Lactobacillus plantarum LC20 |
| 21 | Lactobacillus plantarum LC21 |
| 22 | Lactobacillus plantarum LC22 |
| 23 | Lactobacillus plantarum LC23 |
| 24 | Lactobacillus plantarum LC24 |
| 25 | Lactobacillus plantarum LC25 |
| 26 | Lactobacillus plantarum LC26 |
| 27 | Lactobacillus plantarum LC27 |
| 28 | Lactobacillus plantarum LC28 |
| 29 | Lactobacillus plantarum LC29 |
| 30 | Lactobacillus plantarum LC30 |
| 31 | Lactobacillus plantarum LC31 |
| 32 | Lactobacillus plantarum LC32 |
| 33 | Lactobacillus plantarum LC33 |
| 34 | Lactobacillus plantarum LC34 |
| 35 | Lactobacillus plantarum LC35 |
| 36 | Lactobacillus plantarum LC36 |
| 37 | Lactobacillus plantarum LC37 |
| 38 | Lactobacillus plantarum LC38 |
| 39 | Lactobacillus plantarum LC39 |
| 40 | Lactobacillus plantarum LC40 |
| 41 | Lactobacillus plantarum LC41 |
| 42 | Lactobacillus plantarum LC42 |
| 43 | Lactobacillus plantarum LC43 |
| 44 | Lactobacillus plantarum LC44 |
| 45 | Lactobacillus plantarum LC45 |
| 46 | Lactobacillus plantarum LC46 |
| 47 | Lactobacillus plantarum LC47 |
| 48 | Lactobacillus plantarum LC48 |
| 49 | Lactobacillus plantarum LC49 |
| 50 | Lactobacillus plantarum LC50 |

TABLE 11

| Control No. | Strain name |
|---|---|
| 51 | Bifidobacterium longum LC51 |
| 52 | Bifidobacterium longum LC52 |
| 53 | Bifidobacterium longum LC53 |
| 54 | Bifidobacterium longum LC54 |
| 55 | Bifidobacterium longum LC55 |
| 56 | Bifidobacterium longum LC56 |
| 57 | Bifidobacterium longum LC57 |
| 58 | Bifidobacterium longum LC58 |
| 59 | Bifidobacterium longum LC59 |
| 60 | Bifidobacterium longum LC60 |
| 61 | Bifidobacterium longum LC61 |
| 62 | Bifidobacterium longum LC62 |
| 63 | Bifidobacterium longum LC63 |
| 64 | Bifidobacterium longum LC64 |
| 65 | Bifidobacterium longum LC65 |
| 66 | Bifidobacterium longum LC66 |
| 67 | Bifidobacterium longum LC67 |
| 68 | Bifidobacterium longum LC68 |
| 69 | Bifidobacterium longum LC69 |
| 70 | Bifidobacterium longum LC70 |
| 71 | Bifidobacterium longum LC71 |
| 72 | Bifidobacterium longum LC72 |
| 73 | Bifidobacterium longum LC73 |
| 74 | Bifidobacterium longum LC74 |
| 75 | Bifidobacterium longum JL75 |
| 76 | Bifidobacterium longum LC76 |
| 77 | Bifidobacterium longum LC77 |
| 78 | Bifidobacterium longum LC78 |
| 79 | Bifidobacterium longum LC79 |
| 80 | Bifidobacterium longum LC80 |
| 81 | Bifidobacterium longum LC81 |
| 82 | Bifidobacterium longum LC82 |
| 83 | Bifidobacterium longum LC83 |
| 84 | Bifidobacterium longum LC84 |
| 85 | Bifidobacterium longum LC85 |
| 86 | Bifidobacterium longum LC86 |
| 87 | Bifidobacterium longum LC87 |
| 88 | Bifidobacterium longum LC88 |
| 89 | Bifidobacterium longum LC89 |
| 90 | Bifidobacterium longum LC90 |
| 91 | Bifidobacterium longum LC91 |
| 92 | Bifidobacterium longum LC92 |
| 93 | Bifidobacterium longum LC93 |
| 94 | Bifidobacterium longum LC94 |
| 95 | Bifidobacterium longum LC95 |
| 96 | Bifidobacterium longum LC96 |
| 97 | Bifidobacterium longum LC97 |
| 98 | Bifidobacterium longum LC98 |
| 99 | Bifidobacterium longum LC99 |
| 100 | Bifidobacterium longum LC100 |

It was shown that *Lactobacillus plantarum* LC5 shown in Table 10 above was a gram-positive anaerobic *bacillus* and the 16S rDNA thereof had a nucleotide sequence of SEQ ID NO: 4. The 16S rDNA nucleotide sequence of *Lactobacillus plantarum* LC5 was identified by BLAST in Genebank (ncbi.nlm.nih.gov), and as a result, a *Lactobacillus plantarum* strain having the same 16S rDNA nucleotide sequence as that of *Lactobacillus plantarum* LC5 was not found, and *Lactobacillus plantarum* LC5 showed a homology of 99% with the 16S rDNA sequence of *Lactobacillus plantarum* strain KF9. Furthermore, it was shown that *Lactobacillus plantarum* LC27 shown in Table 10 above was a gram-positive anaerobic *bacillus* and the 16S rDNA thereof had a nucleotide sequence of SEQ ID NO: 5. The 16S rDNA nucleotide sequence of *Lactobacillus plantarum* LC27 was identified by BLAST in Genebank (ncbi.nlm.nih.gov), and as a result, a *Lactobacillus plantarum* strain having the same 16S rDNA nucleotide sequence as that of *Lactobacillus plantarum* LC27 was not found, and *Lactobacillus plantarum* LC27 showed a homology of 99% with the 16S rDNA sequence of *Lactobacillus plantarum* strain JL18. In addition, it was shown that *Lactobacillus plantarum* LC28 shown in Table 10 above was a gram-positive anaerobic *bacillus* and the 16S rDNA thereof had a nucleotide sequence of SEQ ID NO: 6. The 16S rDNA nucleotide sequence of *Lactobacillus plantarum* LC28 was identified by BLAST in Genebank (ncbi.nlm.nih.gov), and as a result, a *Lactobacillus plantarum* strain having the same 16S rDNA nucleotide sequence as that of *Lactobacillus plantarum* LC28 was not found, and *Lactobacillus plantarum* LC28 showed a homology of 99% with the 16S rDNA sequence of *Lactobacillus plantarum* strain USIM01.

It was shown that *Bifidobacterium longum* LC67 shown in Table 11 above was a gram-positive anaerobic *bacillus* and the 16S rDNA thereof had a nucleotide sequence of SEQ ID NO: 7. The 16S rDNA nucleotide sequence of *Bifidobacterium longum* LC67 was identified by BLAST in Genebank (ncbi.nlm.nih.gov), and as a result, a *Bifidobacterium longum* strain having the same 16S rDNA nucleotide sequence as that of *Bifidobacterium longum* LC67 was not found, and *Bifidobacterium longum* LC67 showed a homology of 99% with the 16S rDNA sequence of *Bifidobacterium longum* strain CBT-6. Furthermore, it was shown that *Bifidobacterium longum* LC68 shown in Table 11 above was a gram-positive anaerobic *bacillus* and the 16S rDNA thereof had a nucleotide sequence of SEQ ID NO: 8. The 16S rDNA nucleotide sequence of *Bifidobacterium longum* LC68 was identified by BLAST in Genebank (ncbi.nlm.nih.gov), and as a result, a *Bifidobacterium longum* strain having the same 16S rDNA nucleotide sequence as that of *Bifidobacterium longum* LC68 was not found, and *Bifidobacterium longum* LC68 showed a homology of 99% with the 16S rDNA sequence of *Bifidobacterium longum* strain IMAUFB067.

In addition, among the physiological characteristics of *Lactobacillus plantarum* LC5, *Lactobacillus plantarum* LC27, *Bifidobacterium longum* LC67 and *Bifidobacterium longum* LC68, the carbon source utilization was analyzed using a sugar fermentation by an API kit (model: API 50 CHL; manufactured by BioMerieux's, USA). Table 12 below shows the results of analyzing the carbon source utilization of *Lactobacillus plantarum* LC5 and *Lactobacillus plantarum* LC27, and Table 13 below shows the results of analyzing the carbon source utilization of *Bifidobacterium longum* LC67 and *Bifidobacterium longum* LC68. In Tables 12 and 13 below, "+" indicates the case in which carbon source utilization is positive; "−" indicates the case in which carbon source utilization is negative; and "±" indicates the case in which carbon source utilization is ambiguous. As shown in 12 and 13 below, *Lactobacillus plantarum* LC5, *Lactobacillus plantarum* LC27, *Bifidobacterium longum* LC67 and *Bifidobacterium longum* LC68 showed carbon source utilization different from that of known strains of the same species with respect to some carbon sources.

TABLE 12

| Carbon source | *L. plantarum* LC5 | *L. plantarum* LC27 | Carbon source | *L. plantarum* LC5 | *L. plantarum* LC27 |
|---|---|---|---|---|---|
| glycerol | − | − | salicin | + | + |
| erythritol | − | − | cellobiose | + | + |
| D-arabinose | − | − | maltose | + | + |
| L-arabinose | − | + | lactose | − | + |
| D-ribose | + | + | melibiose | + | + |
| D-xylose | − | − | sucrose | + | + |
| L-xylose | − | − | trehalose | + | + |
| D-adonitol | − | − | inulin | − | − |
| methyl-β-D-xylopyranoside | − | − | melezitose | + | + |
| D-galactose | + | ± | raffinose | ± | − |
| D-glucose | + | + | starch | − | − |
| D-fructose | + | + | glycogen | − | − |
| D-mannose | + | + | xylitol | − | − |
| L-sorbose | − | − | gentiobiose | + | + |
| L-rhamnose | − | ± | D-turanose | − | + |
| dulcitol | − | − | D-lyxose | − | − |
| inositol | − | − | D-tagatose | − | − |
| mannitol | + | + | D-fucose | − | − |
| sorbitol | + | + | L-fucose | − | − |
| α-methyl-D-mannoside | − | ± | D-arabitol | − | − |
| α-methly-D-glucoside | − | − | L-arabitol | − | − |
| N-acetyl-glucosamine | + | + | gluconate | − | − |
| amygdalin | + | + | 2-keto-gluconate | − | − |
| arbutin | + | + | 5-keto-gluconate | − | − |
| esculin | + | + | | | |

TABLE 13

| Carbon source | *B. longum* LC67 | *B. longum* LC68 | Carbon source | *B. longum* LC67 | *B. longum* LC68 |
|---|---|---|---|---|---|
| glycerol | − | − | salicin | − | − |
| erythritol | − | − | cellobiose | − | − |
| D-arabinose | − | − | maltose | + | + |
| L-arabinose | + | + | lactose | + | + |
| D-ribose | − | − | melibiose | + | + |
| D-xylose | + | ± | sucrose | + | ± |
| L-xylose | − | − | trehalose | − | ± |
| D-adonitol | − | − | inulin | − | − |
| methyl-β-D-xylopyranoside | − | − | melezitose | − | + |
| D-galactose | ± | + | raffinose | + | + |
| D-glucose | + | + | starch | − | − |
| D-fructose | + | + | glycogen | − | − |

TABLE 13-continued

| Carbon source | B. longum LC67 | B. longum LC68 | Carbon source | B. longum LC67 | B. longum LC68 |
|---|---|---|---|---|---|
| D-mannose | − | − | xylitol | − | − |
| L-sorbose | − | − | gentiobiose | + | ± |
| L-rhamnose | − | − | D-turanose | ± | ± |
| dulcitol | − | − | D-lyxose | − | − |
| inositol | − | − | D-tagatose | − | − |
| mannitol | ± | + | D-fucose | − | − |
| sorbitol | ± | + | L-fucose | − | − |
| α-methyl-D-mannoside | − | − | D-arabitol | − | − |
| α-methly-D-glucoside | ± | ± | L-arabitol | − | − |
| N-acetyl-glucosamine | − | − | gluconate | − | − |
| amygdalin | − | ± | 2-keto-gluconate | − | − |
| arbutin | − | − | 5-keto-gluconate | − | − |
| esculin | + | + | | | |

(4) Information on Deposition of Lactic Acid Bacteria

The present inventors deposited *Lactobacillus plantarum* LC5 with the Korean Culture Center of Microorganisms (address: Yurim Building, 45, Hongjenae 2ga-gil, Seodaemun-gu, Seoul, Korea), an international depositary authority, on Jan. 11, 2016 under accession number KCCM 11800P. Furthermore, the present inventors deposited *Lactobacillus plantarum* LC27 with the Korean Culture Center of Microorganisms (address: Yurim Building, 45, Hongjenae 2ga-gil, Seodaemun-gu, Seoul, Korea), an international depositary authority, on Jan. 11, 2016 under accession number KCCM 11801P. Furthermore, the present inventors deposited *Bifidobacterium longum* LC67 with the Korean Culture Center of Microorganisms (address: Yurim Building, 45, Hongjenae 2ga-gil, Seodaemun-gu, Seoul, Korea), an international depositary authority, on Jan. 11, 2016 under accession number KCCM 11802P.

2. Evaluation of the Effect of Lactic Acid Bacteria on Alleviation of Intestinal Damage or Intestinal Permeability In order to evaluate the effect of the lactic acid bacteria isolated from kimchi or human feces, on the alleviation of intestinal damage or internal permeability, the antioxidant activity, lipopolysaccharide (LPS) production inhibitory activity, β-glucuronidase (harmful intestinal enzyme) inhibitory activity and tight junction protein expression-inducing activity of the lactic acid bacteria were measured.

(1) Experimental Methods

*Antioxidant Activity

DPPH (2,2-diphenyl-1-picrylhydrazyl) was dissolved in ethanol to a concentration of 0.2 mM to prepare a DPPH solution. A lactic acid bacteria suspension ($1\times10^8$ CFU/ml) or a vitamin C solution (1 g/ml) was added to 0.1 ml of the DPPH solution and cultured at 37° C. for 20 minutes. The culture was centrifuged at 3000 rpm for 5 minutes, and the supernatant was collected. Next the absorbance of the supernatant at 517 nm was measured, and the antioxidant activity of the lactic acid bacteria was calculated.

*Lipopolysaccharide (LPS) Production Inhibitory Activity 0.1 g of human fresh feces was suspended in 0.9 ml of sterile physiological saline and diluted 100-fold with general anaerobic medium to prepare a fecal suspension. 0.1 ml of the fecal suspension and 0.1 ml of lactic acid bacteria ($1\times10^4$ or $1\times10^5$ CFU) were added to 9.8 ml of sterile anaerobic medium (Nissui Pharmaceuticals, Japan) and cultured anaerobically for 24 hours. Next, the culture was sonicated for about 1 hour to disrupt the outer cell membrane of the bacteria, and centrifuged at 5000×g and the supernatant was collected. Next, the content of LPS (lipopolysaccharide) (which is a typical endotoxin) in the supernatant was measured by a LAL (Limulus Amoebocyte Lysate) assay kit (manufactured by Cape Cod Inc., USA). In addition, in order to evaluate the *E. coli* proliferation inhibitory activity of the lactic acid bacteria, the culture obtained through the same experiment as described above was diluted 1000-fold and 100000-fold and cultured in DHL medium, and then the number of *E. coli* cells was counted.

*β-Glucuronidase Inhibitory Activity 0.1 ml of 0.1 mM p-nitrophenyl-β-D-glucuronide solution, 0.2 ml of 50 mM phosphate buffered saline and 0.1 ml of a lactic acid bacteria suspension (prepared by suspending of a lactic acid bacteria culture in 5 ml of physiological saline) were placed in a reactor and subjected to β-glucuronidase enzymatic reaction, and 0.5 ml of 0.1 mM NaOH solution was added to stop the reaction. Next, the reaction solution was centrifuged at 3000 rpm for 5 minutes, and the supernatant was collected. Then, the absorbance of the supernatant at 405 nm was measured.

*Tight Junction Protein Expression-Inducing Activity

Caco2 cells obtained from the Korean Cell Line Bank were cultured in RPMI 1640 medium for 48 hours, and then the cultured Caco2 cells were dispensed to each well of a 12-well plate at a density of $2\times10^6$ cells/well. Next, each well was treated with 1 μg of LPS (lipopolysaccharide) or a combination of 1 μg of LPS (lipopolysaccharide) and $1\times10^3$ CFU of lactic acid bacteria and incubated for 24 hours. Next, the cultured cells were collected from each well, and the expression level of tight junction protein ZO-1 in the cells was measured by an immunoblotting method.

(2) Experimental Results

The antioxidant activity, lipopolysaccharide (LPS) production inhibitory activity, β-glucuronidase inhibitory activity and tight junction protein expression-inducing activity of the lactic acid bacteria isolated from kimchi or human feces were measured, and the results of the measurement are shown in Tables 14 to 16 below. As shown in Tables 14 to 16 below, *Lactobacillus plantarum* LC5, *Lactobacillus plantarum* LC15, *Lactobacillus plantarum* LC17, *Lactobacillus plantarum* LC25, *Lactobacillus plantarum* LC27, *Lactobacillus plantarum* LC28, *Bifidobacterium longum* LC55, *Bifidobacterium longum* LC65, *Bifidobacterium longum* LC67 and *Bifidobacterium longum* LC68 had excellent antioxidant activity, strongly inhibited lipopolysaccharide (LPS) production and β-glucuronidase activity, and strongly induced the expression of tight junction protein. In particular, *Bifidobacterium longum* LC67 showed the best tight junction protein expression-inducing activity. These lactic acid bacteria have an excellent antioxidant effect, have an excellent effect of inhibiting the enzymatic activity of intestinal flora's harmful bacteria associated with inflammation and carcinogenesis, inhibit the production of endotoxin LPS (lipopolysaccharide) produced by intestinal flora's harmful bacteria, and induce the expression of tight junction protein. Thus, these lactic acid bacteria can improve intestinal permeability syndrome.

TABLE 14

| Control No. | Strain name | Antioxidant activity | Beta-glucuronidase inhibitory activity | LPS production inhibitory activity | Tight junction protein expression inducing activity |
|---|---|---|---|---|---|
| 1 | *Lactobacillus plantarum* LC1 | ++ | + | + | − |
| 2 | *Lactobacillus plantarum* LC2 | ++ | ++ | + | − |
| 3 | *Lactobacillus plantarum* LC3 | +++ | ++ | + | − |
| 4 | *Lactobacillus plantarum* LC4 | +++ | ++ | + | + |
| 5 | *Lactobacillus plantarum* LC5 | +++ | +++ | ++ | ++ |
| 6 | *Lactobacillus plantarum* LC6 | ++ | +++ | + | − |
| 7 | *Lactobacillus plantarum* LC7 | +++ | ++ | + | − |
| 8 | *Lactobacillus plantarum* LC8 | ++ | +++ | + | − |
| 9 | *Lactobacillus plantarum* LC9 | ++ | ++ | + | + |
| 10 | *Lactobacillus plantarum* LC10 | ++ | +++ | + | + |
| 11 | *Lactobacillus plantarum* LC11 | ++ | ++ | + | − |
| 12 | *Lactobacillus plantarum* LC12 | ++ | +++ | + | + |
| 13 | *Lactobacillus plantarum* LC13 | ++ | ++ | + | + |
| 14 | *Lactobacillus plantarum* LC14 | ++ | ++ | + | − |
| 15 | *Lactobacillus plantarum* LC15 | +++ | +++ | ++ | ++ |
| 16 | *Lactobacillus plantarum* LC16 | + | +++ | + | − |
| 17 | *Lactobacillus plantarum* LC17 | +++ | +++ | ++ | ++ |
| 18 | *Lactobacillus plantarum* LC18 | ++ | ++ | + | + |
| 19 | *Lactobacillus plantarum* LC19 | ++ | +++ | + | + |
| 20 | *Lactobacillus plantarum* LC20 | ++ | ++ | + | − |
| 21 | *Lactobacillus plantarum* LC21 | ++ | ++ | + | − |
| 22 | *Lactobacillus plantarum* LC22 | ++ | +++ | − | − |
| 23 | *Lactobacillus plantarum* LC23 | +++ | ++ | − | − |
| 24 | *Lactobacillus plantarum* LC24 | +++ | + | − | − |
| 25 | *Lactobacillus plantarum* LC25 | +++ | +++ | ++ | ++ |
| 26 | *Lactobacillus plantarum* LC26 | ++ | + | + | + |
| 27 | *Lactobacillus plantarum* LC27 | +++ | +++ | ++ | ++ |
| 28 | *Lactobacillus plantarum* LC28 | +++ | +++ | ++ | ++ |
| 29 | *Lactobacillus plantarum* LC29 | ++ | + | − | − |
| 30 | *Lactobacillus plantarum* LC30 | ++ | + | + | − |
| 31 | *Lactobacillus plantarum* LC31 | +++ | ++ | + | − |
| 32 | *Lactobacillus plantarum* LC32 | +++ | ++ | + | − |
| 33 | *Lactobacillus plantarum* LC33 | +++ | ++ | + | − |
| 34 | *Lactobacillus plantarum* LC34 | ++ | ++ | + | + |
| 35 | *Lactobacillus plantarum* LC35 | ++ | ++ | + | + |

TABLE 15

| Control No. | Strain name | Antioxidant activity | Beta-glucuronidase inhibitory activity | LPS production inhibitory activity | Tight junction protein expression inducing activity |
|---|---|---|---|---|---|
| 36 | *Lactobacillus plantarum* LC36 | ++ | ++ | ++ | − |
| 37 | *Lactobacillus plantarum* LC37 | +++ | ++ | + | + |
| 38 | *Lactobacillus plantarum* LC38 | ++ | ++ | + | − |
| 39 | *Lactobacillus plantarum* LC39 | ++ | + | + | − |
| 40 | *Lactobacillus plantarum* LC40 | +++ | + | − | − |
| 41 | *Lactobacillus plantarum* LC41 | ++ | ++ | − | + |
| 42 | *Lactobacillus plantarum* LC42 | +++ | + | − | + |
| 43 | *Lactobacillus plantarum* LC43 | ++ | + | − | + |
| 44 | *Lactobacillus plantarum* LC44 | ++ | + | − | + |
| 45 | *Lactobacillus plantarum* LC45 | ++ | ++ | − | + |
| 46 | *Lactobacillus plantarum* LC46 | ++ | + | − | + |
| 47 | *Lactobacillus plantarum* LC47 | +++ | + | − | + |
| 48 | *Lactobacillus plantarum* LC48 | ++ | ++ | − | + |
| 49 | *Lactobacillus plantarum* LC49 | ++ | +++ | + | + |
| 50 | *Lactobacillus plantarum* LC50 | +++ | ++ | + | + |
| 51 | *Bifidobacterium longum* LC51 | ++ | ++ | + | − |
| 52 | *Bifidobacterium longum* LC52 | +++ | +++ | + | − |
| 53 | *Bifidobacterium longum* LC53 | ++ | +++ | − | + |
| 54 | *Bifidobacterium longum* LC54 | +++ | ++ | + | + |

TABLE 15-continued

| Control No. | Strain name | Antioxidant activity | Beta-glucuronidase inhibitory activity | LPS production inhibitory activity | Tight junction protein expression inducing activity |
|---|---|---|---|---|---|
| 55 | *Bifidobacterium longum* LC55 | +++ | +++ | ++ | ++ |
| 56 | *Bifidobacterium longum* LC56 | +++ | ++ | + | + |
| 57 | *Bifidobacterium longum* LC57 | ++ | + | − | + |
| 58 | *Bifidobacterium longum* LC58 | +++ | + | − | + |
| 59 | *Bifidobacterium longum* LC59 | ++ | + | − | − |
| 60 | *Bifidobacterium longum* LC60 | +++ | + | − | − |
| 61 | *Bifidobacterium longum* LC61 | ++ | + | + | − |
| 62 | *Bifidobacterium longum* LC62 | +++ | + | + | − |
| 63 | *Bifidobacterium longum* LC63 | ++ | ++ | ++ | − |
| 64 | *Bifidobacterium longum* LC64 | +++ | + | − | − |
| 65 | *Bifidobacterium longum* LC65 | +++ | +++ | ++ | ++ |
| 66 | *Bifidobacterium longum* LC66 | ++ | + | + | + |
| 67 | *Bifidobacterium longum* LC67 | +++ | +++ | ++ | +++ |
| 68 | *Bifidobacterium longum* LC68 | +++ | +++ | ++ | ++ |
| 69 | *Bifidobacterium longum* LC69 | +++ | + | − | − |
| 70 | *Bifidobacterium longum* LC70 | ++ | + | − | + |

TABLE 16

| Control No. | Strain name | Antioxidant activity | Beta-glucuronidase inhibitory activity | LPS production inhibitory activity | Tight junction protein expression inducing activity |
|---|---|---|---|---|---|
| 71 | *Bifidobacterium longum* LC71 | ++ | + | − | + |
| 72 | *Bifidobacterium longum* LC72 | +++ | ++ | − | + |
| 73 | *Bifidobacterium longum* LC73 | ++ | ++ | + | − |
| 74 | *Bifidobacterium longum* LC74 | ++ | +++ | + | − |
| 75 | *Bifidobacterium longum* LC75 | +++ | + | − | + |
| 76 | *Bifidobacterium longum* LC76 | ++ | + | − | + |
| 77 | *Bifidobacterium longum* LC77 | ++ | ++ | + | + |
| 78 | *Bifidobacterium longum* LC78 | ++ | + | + | + |
| 79 | *Bifidobacterium longum* LC79 | +++ | + | + | + |
| 80 | *Bifidobacterium longum* LC80 | ++ | + | + | + |
| 81 | *Bifidobacterium longum* LC81 | ++ | + | + | + |
| 82 | *Bifidobacterium longum* LC82 | ++ | ++ | − | + |
| 83 | *Bifidobacterium longum* LC83 | +++ | + | − | + |
| 84 | *Bifidobacterium longum* LC84 | ++ | ++ | − | − |
| 85 | *Bifidobacterium longum* LC85 | +++ | ++ | − | + |
| 86 | *Bifidobacterium longum* LC86 | ++ | + | + | − |
| 87 | *Bifidobacterium longum* LC87 | ++ | ++ | + | − |
| 88 | *Bifidobacterium longum* LC88 | ++ | +++ | + | + |
| 89 | *Bifidobacterium longum* LC89 | ++ | ++ | + | + |
| 90 | *Bifidobacterium longum* LC90 | ++ | ++ | + | + |
| 91 | *Bifidobacterium longum* LC91 | +++ | +++ | + | + |
| 92 | *Bifidobacterium longum* LC92 | +++ | ++ | + | + |
| 93 | *Bifidobacterium longum* LC93 | ++ | ++ | + | + |
| 94 | *Bifidobacterium longum* LC94 | ++ | ++ | − | + |
| 95 | *Bifidobacterium longum* LC95 | ++ | +++ | − | − |
| 96 | *Bifidobacterium longum* LC96 | ++ | + | − | − |
| 97 | *Bifidobacterium longum* LC97 | ++ | + | − | − |
| 98 | *Bifidobacterium longum* LC98 | ++ | ++ | − | − |
| 99 | *Bifidobacterium longum* LC99 | ++ | ++ | − | − |
| 100 | *Bifidobacterium longum* LC100 | ++ | ++ | − | + |

\* The final concentration of lactic acid bacteria in measurement of antioxidant activity: $1 \times 10^4$ CFU/ml; the concentration of lactic acid bacteria added for measurement of beta-glucuronidase inhibitory activity and lipopolysaccharide (LPS) production inhibitory activity: $1 \times 10^4$ CFU/ml; the concentration of lactic acid bacteria in measurement of tight junction protein expression-inducing activity: $1 \times 10^4$ CFU/ml.
\* Criteria for measurement of various activities of lactic acid bacteria: very strongly (+++; >90%); strongly (++; >60-90%); weakly (+; >20-60%); not or less than 20% (−; <20%).

3. Evaluation of the Effect of Lactic Acid Bacteria on Alleviation of Liver Injury Based on evaluation of the effect of the lactic acid bacteria on the alleviation of intestinal damage or intestinal permeability syndrome, the following ten strains were selected: *Lactobacillus plantarum* LC5, *Lactobacillus plantarum* LC15, *Lactobacillus plantarum* LC17, *Lactobacillus plantarum* LC25 *Lactobacillus plantarum* LC27, *Lactobacillus plantarum* LC28, *Bifidobacterium longum* LC55, *Bifidobacterium longum* LC65, *Bifidobacterium longum* LC67 and *Bifidobacterium longum* LC68. The effect of each of these selected lactic acid bacteria strains or a mixture of these strains on the alleviation of liver injury was evaluated using model animals having liver injury induced by tert-butylperoxide.

1) Experimental Method

Mice (C57BL/6, male) were divided into several groups, each consisting of 6 animals. Tert-butylperoxide was administered intraperitoneally to the test animals of groups other than a normal group at a dose of 2.5 mmol/kg to induce liver injury. From 2 hours after administration of tert-butylperoxide, $2 \times 10^9$ CFU of lactic acid bacteria were administered orally to the test animals of groups other than the normal group and the negative control group, once a day for days. In addition, silymarin in place of lactic acid bacteria was administered orally to the test animals of the positive control group at a dose of 100 mg/kg, once a day for 3 days. At 6 hours after the last administration of the drug, blood was taken from the heart. The taken blood was allowed to stand at room temperature for 60 minutes, and centrifuged at 3,000 rpm for 15 minutes to separate serum. The GPT (glutamic pyruvate transaminase) and GOT (glutamic oxalacetic transaminase) levels in the separated serum were measured using a blood assay kit (ALT & AST measurement kit; Asan Pharm. Co., Korea). In addition, 1 g of the liver tissue dissected from each test animal was added to saline and homogenized using a homogenizer, and the supernatant was analyzed by an ELISA kit to measure the level of TNF-α.

(2) Experimental Results

Table 17 below shows the changes in GOT, GPT and TNF-α values when lactic acid bacteria were administered to model animals having liver injury induced by tert-butylperoxide. As shown in Table 17 below, *Lactobacillus plantarum* LC5, *Lactobacillus plantarum* LC27, *Lactobacillus plantarum* LC28, *Bifidobacterium longum* LC67 and *Bifidobacterium longum* LC68 showed excellent effects on the alleviation of liver injury compared to silymarin, and mixtures of these lactic acid bacteria showed better effects on the alleviation of liver injury.

TABLE 17

| Test groups | GOT (IU/L) | GPT (IU/L) | TNF-α (pg/g) |
|---|---|---|---|
| Normal group | 42.4 | 6.2 | 140.4 |
| Negative control group | 103.1 | 28.0 | 298.0 |
| Group administered with LC5 | 36.9 | 5.4 | 115.7 |
| Group administered with LC15 | 60.3 | 6.2 | 154.3 |
| Group administered with LC17 | 65.8 | 6.8 | 136.7 |
| Group administered with LC25 | 64.6 | 11.3 | 132.4 |
| Group administered with LC27 | 35.3 | 3.3 | 157.1 |
| Group administered with LC28 | 42.0 | 1.0 | 185.7 |
| Group administered with LC55 | 55.6 | 17.6 | 251.4 |
| Group administered with LC65 | 61.4 | 17.3 | 127.6 |
| Group administered with LC67 | 50.8 | 3.8 | 150.5 |
| Group administered with LC68 | 40.8 | 5.7 | 82.4 |
| Group administered with LC5 + LC67 | 32.7 | 3.1 | 115.9 |
| Group administered with LC5 + LC68 | 36.8 | 5.6 | 105.4 |
| Group administered with LC27 + LC67 | 30.5 | 2.3 | 121.2 |
| Group administered with LC27 + LC68 | 35.4 | 3.2 | 112.8 |
| Group administered with LC28 + LC67 | 32.5 | 2.8 | 128.2 |
| Group administered with silymarin | 52.9 | 5.9 | 93.8 |

In Table 17 above, "LC5" indicates *Lactobacillus plantarum* LC5; "LC15" indicates *Lactobacillus plantarum* LC15; "LC17" indicates *Lactobacillus plantarum* LC17; "LC25" indicates *Lactobacillus plantarum* LC25; "LC27" indicates *Lactobacillus plantarum* LC27; "LC28" indicates *Lactobacillus plantarum* LC28; "LC55" indicates *Bifidobacterium longum* LC55; "LC65" indicates *Bifidobacterium longum* LC65; "LC67" indicates *Bifidobacterium longum* LC67; "LC68" indicates *Bifidobacterium longum* LC68; "LC5+LC67" indicates a lactic acid bacteria mixture prepared by mixing *Lactobacillus plantarum* LC5 and *Bifidobacterium longum* LC67 in the same amount; "LC5+LC68" indicates a lactic acid bacteria mixture prepared by mixing *Lactobacillus plantarum* LC5 and *Bifidobacterium longum* LC68 in the same amount; "LC27+LC67" indicates a lactic acid bacteria mixture prepared by mixing *Lactobacillus plantarum* LC27 and *Bifidobacterium longum* LC67 in the same amount; "LC27+LC68" indicates a lactic acid bacteria mixture prepared by mixing *Lactobacillus plantarum* LC27 and *Bifidobacterium longum* LC68 in the same amount; and "LC28+LC67" indicates a lactic acid bacteria mixture prepared by mixing *Lactobacillus plantarum* LC28 and *Bifidobacterium longum* LC67 in the same amount. In the following Tables showing the experimental results, the same symbols are used for single lactic acid bacteria or lactic acid bacteria mixtures.

4. Evaluation of the Effect of Lactic Acid Bacteria on Alleviation of Allergy (1) Measurement of the Inhibition of Degranulation by Lactic Acid Bacteria The RBL-2H3 cell line (rat mast cell line, the Korean Cell Line Bank, Cat. No. 22256) was cultured with DMEM (Dulbeccos' modified Eagle's medium, Sigma, 22256) containing 10% FBS (fetal bovine serum) and L-glutamine in a humidified 5% $CO_2$ incubator at 37° C. The cells contained in the culture medium were floated using trypsin-EDTA solution, and the floated cells were isolated, collected and used in the experiment. The collected RBL-2H3 cells were dispensed into a 24-well plate at a density of $5 \times 10^5$ cells/well and sensitized by incubation with 0.5 μg/ml of mouse monoclonal IgE for 12 hours. The sensitized cells were washed with 0.5 ml of siraganian buffer (119 mM NaCl, 5 mM KCl, 0.4 mM $MgCl_2$, 25 mM PIPES, 40 mM NaOH, pH 7.2), and then incubated with 0.16 ml of siraganian buffer (supplemented with 5.6 mM glucose, 1 mM $CaCl_2$, 0.1% BSA) at 37° C. for 10 minutes. Next, lactic acid bacteria as a test drug were added to the cell culture to a concentration of $1 \times 10^4$ CFU/ml, or 0.04 ml of DSCG (disodium cromoglycate) as a control drug was added to the cell culture, and after 20 minutes, the cells were activated with 0.02 ml of antigen (1 μg/ml DNP-BSA) at 37° C. for 10 minutes. Next, the cell culture was centrifuged at 2000 rpm for 10 minutes, and the supernatant was collected. 0.025 ml of the collected supernatant was transferred to a 96-well plate, and then 0.025 ml of 1 mM p-NAG (a solution of p-nitrophenyl-N-acetyl-β-D-glucosamide in 0.1M citrate buffer, pH 4.5) was added thereto, and then the mixture was allowed to react at 37° C. for 60 minutes. Next, the reaction was stopped by addition of 0.2 ml of 0.1M $Na_2CO_3/NaHCO_3$, and the absorbance at 405 nm was measured by an ELISA analyzer.

(2) Experimental Results

Table 18 below shows the results of measuring of the inhibition (%) of degranulation by lactic acid bacteria. As shown in Table 18, *Lactobacillus plantarum* LC5, *Lactobacillus plantarum* LC27, *Lactobacillus plantarum* LC28, *Bifidobacterium longum* LC67, *Bifidobacterium longum* LC68 and mixtures thereof effectively inhibited the degranulation of basophils. Thus, these lactic acid bacteria or mixtures thereof can very effectively alleviate allergic atopy, asthma, pharyngitis, chronic dermatitis or the like.

TABLE 18

| Drug | Degranulation inhibition (%) |
|---|---|
| None | 0 |
| LC5 | 65 |

TABLE 18-continued

| Drug | Degranulation inhibition (%) |
| --- | --- |
| LC15 | 45 |
| LC17 | 43 |
| LC25 | 48 |
| LC27 | 52 |
| LC28 | 54 |
| LC55 | 38 |
| LC65 | 42 |
| LC67 | 65 |
| LC68 | 61 |
| LC5 + LC67 | 65 |
| LC5 + LC68 | 60 |
| LC27 + LC67 | 65 |
| LC27 + LC68 | 59 |
| LC28 + LC67 | 62 |
| DSCG(disodium cromoglycate) | 62 |

5. In Vitro Evaluation of the Anti-Inflammatory and Immune Regulatory Effects of Lactic Acid Bacteria (1) Isolation of Macrophages and Measurement of Inflammatory Marker 6-Week-old C57BL/6J male mice (20-23 g) were purchased from RaonBio Co., Ltd. 2 ml of 4% sterile thioglycolate was administered into the abdominal cavity of each mouse, after 96 hours, the mice were anesthetized and 8 ml of RPMI 1640 medium was administered into the abdominal cavity of each mouse.

After 5-10 minutes, the RPMI medium (including macrophages) in the abdominal cavity of the mice was taken out, centrifuged at 1000 rpm for 10 minutes, and then washed twice with RPMI 1640 medium. The macrophages were seeded on a 24-well plate at a density of $0.5 \times 10^6$ cells/well and treated with the test substance lactic acid bacteria and the inflammation inducer LPS (lipopolysaccharide) for 2 hours or 24 hours, and then the supernatant and the cells were collected. In this case, the lactic acid bacteria were used at a concentration of $1 \times 10^4$ CFU/ml for treatment of the cells. The collected cells were homogenized in buffer (Gibco). Using the collected supernatant, the expression levels of cytokines such as TNF-α were measured by an ELISA kit. In addition, using the collected cells, the expression levels of p65 (NF-kappa B), p-p65 (phosphor-NF-kappa B) and β-actin were measured by an immunoblotting method. Specifically, 50 μg of the supernatant was taken and electrophoresed on SDS 10% (w/v) polyacrylamide gel for 1 hour and 30 minutes. The electrophoresed sample was transferred to a nitrocellulose membrane under the conditions of 100 V and 400 mA for 1 hour and 10 minutes. The sample-transferred nitrocellulose membrane was blocked with 5% skim milk for 30 minutes, and then washed three times with PBS-Tween for 5 minutes each time, and incubated with a 1:100 dilution of primary antibody (Santa Cruz Biotechnology, USA) overnight. Next, the membrane was washed three times for 10 minutes each time, and incubated with a 1:1000 dilution of secondary antibody (Santa Cruz Biotechnology, USA) for 1 hour and 20 minutes. Next, the membrane was washed three times for 15 minutes each time, and it was developed by fluorescence and visualized. The intensity of the developed band was measured, and then inhibition (%) was calculated using the following equation. In the following equation, the normal group indicates a group in which macrophages were treated with saline alone; the group treated with LPS indicates a group in which macrophages were treated with LPS alone; and the group treated with lactic acid bacteria indicates a group in which macrophages were treated with both lactic acid bacteria and LPS.

Inhibition (%)=(expression level in group treated with LPS−expression level in group treated with lactic acid bacteria)/(expression level in group treated with LPS−expression level in normal group)×100

Table 19 below shows the inhibition of NF-kappa B activation and the inhibition of TNF-α expression when macrophages having inflammation induced by LPS (lipopolysaccharide) were treated with the lactic acid bacteria. As shown in Table 19 below, Lactobacillus plantarum LC5, Lactobacillus plantarum LC27, Lactobacillus plantarum LC28, Bifidobacterium longum LC67, Bifidobacterium longum LC68 and mixtures thereof effectively inhibited inflammation induced by LPS (lipopolysaccharide).

TABLE 19

| Lactic acid bacteria used for treatment | Inhibition (%) of TNF-α expression | Inhibition (%) of p-p65/p65 activation |
| --- | --- | --- |
| LC5 | 71 | 73 |
| LC15 | 54 | 55 |
| LC17 | 61 | 55 |
| LC25 | 52 | 65 |
| LC27 | 70 | 72 |
| LC28 | 74 | 71 |
| LC55 | 63 | 62 |
| LC65 | 65 | 68 |
| LC67 | 76 | 77 |
| LC68 | 75 | 71 |
| LC5 + LC67 | 78 | 72 |
| LC5 + LC68 | 76 | 72 |
| LC27 + LC67 | 81 | 75 |
| LC27 + LC68 | 77 | 73 |
| LC28 + LC67 | 77 | 73 |

(2) Isolation of T Cells from Spleen and Measurement of Differentiation into Th17 Cells or Treg Cells Spleen was separated from C56BL/6J mice, crushed suitably and suspended in 10% FCS-containing RPMI 1640 medium, and CD4 T cells were isolated therefrom using a CD4 T cell isolation kit (MiltenyiBiotec, Bergisch Gladbach, Germany). The isolated CD4 T cells were seeded in a 12-well plate at a density of $5 \times 10^5$ cells/well, and anti-CD3 (1 μg/ml, MiltenyiBiotec, Bergisch Gladbach, Germany) and anti-CD28 (1 μg/ml, MiltenyiBiotec, Bergisch Gladbach, Germany) were added thereto, or anti-CD3 (1 μg/ml, MiltenyiBiotec, Bergisch Gladbach, Germany), anti-CD28 (1 μg/ml, MiltenyiBiotec, Bergisch Gladbach, Germany), recombinant IL-6 (20 ng/ml, MiltenyiBiotec, Bergisch Gladbach, Germany) and recombinant transforming growth factor beta (1 ng/ml, MiltenyiBiotec, Bergisch Gladbach, Germany) were added. While the cells were cultured, $1 \times 10^3$ or $1 \times 10^5$ CFU of the lactic acid bacteria were added thereto, and the cells were cultured for 4 days. Next, the cells of the culture were stained with anti-FoxP3 or anti-IL-17A antibody, and the distribution of Th17 cells and Treg cells was analyzed using a FACS (fluorescence-activated cell sorting) system (C6 Flow Cytometer® System, San Jose, Calif., USA).

Table 20 below shows the level of differentiation of T cells (isolated from spleen) into Th17 cells when the T cells were treated with anti-CD3, anti-CD28, IL-6 and TGF-β, and Table 21 below shows the level of differentiation of T cells (isolated from spleen) into Treg cells when the T cells were treated with anti-CD3 and anti-CD28. As shown in Tables 20 and 21 below, Lactobacillus plantarum LC5, Lactobacillus plantarum LC27, Lactobacillus plantarum LC28, Bifidobacterium longum LC67, Bifidobacterium longum LC68 and mixtures thereof inhibited the differentiation of T cells into Th17 cells (T helper 17 cells) and promoted the differentiation of T cells into Treg cells. These results suggest that the lactic acid bacteria or mixtures thereof can effectively alleviate inflammatory diseases such as colitis or arthritis.

TABLE 20

T-cell treatment method

| Treatment with anti-CD3, anti-CD28, IL-6 and TGF-β | Treatment with lactic acid bacteria | Differentiation (%) into Th17 cells |
|---|---|---|
| Not treated | Not treated | 12.2 |
| Treated | Not treated | 25.6 |
| Treated | Treated with LC5 | 14.2 |
| Treated | Treated with LC15 | 19.6 |
| Treated | Treated with LC17 | 17.9 |
| Treated | Treated with LC25 | 18.2 |
| Treated | Treated with LC27 | 15.1 |
| Treated | Treated with LC28 | 14.9 |
| Treated | Treated with LC55 | 18.8 |
| Treated | Treated with LC65 | 17.9 |
| Treated | Treated with LC67 | 15.9 |
| Treated | Treated with LC68 | 15.7 |
| Treated | Treated with LC5 + LC67 | 14.2 |
| Treated | Treated with LC5 + LC68 | 14.5 |
| Treated | Treated with LC27 + LC67 | 13.9 |
| Treated | Treated with LC27 + LC68 | 14.4 |
| Treated | Treated with LC28 + LC67 | 14.1 |

TABLE 21

| T-cell treatment method | | Differentiation (%) into Treg cells |
|---|---|---|
| Treatment with anti-CD3 and anti-CD28 | Treatment with lactic acid bacteria | |
| Not treated | Not treated | 9.1 |
| Treated | Not treated | 11.4 |
| Treated | Treated with LC5 | 22.9 |
| Treated | Treated with LC15 | 15.8 |
| Treated | Treated with LC17 | 16.9 |
| Treated | Treated with LC25 | 18.4 |
| Treated | Treated with LC27 | 21.8 |
| Treated | Treated with LC28 | 21.4 |
| Treated | Treated with LC55 | 19.5 |
| Treated | Treated with LC65 | 19.2 |
| Treated | Treated with LC67 | 21.6 |
| Treated | Treated with LC68 | 20.5 |
| Treated | Treated with LC5 + LC67 | 21.8 |
| Treated | Treated with LC5 + LC68 | 21.8 |
| Treated | Treated with LC27 + LC67 | 22.0 |
| Treated | Treated with LC27 + LC68 | 21.5 |
| Treated | Treated with LC28 + LC67 | 21.9 |

6. In Vivo Evaluation of the Anti-Inflammatory and Colitis-Alleviating Effects of Lactic Acid Bacteria (1) Test Animals 5-Week-old C57BL/6 male mice (24-27 g) were purchased from OrientBio, and housed under controlled environmental conditions (humidity: 50±10%, temperature: 25±2° C., 12-hr light/12-hr dark cycle), and then used in the experiment. As feed, standard experimental feed (Samyang, Korea) was used, and the animals had access to drinking water ad libitum. In all the experiments, one group consisted of 6 animals.

(2) Colitis Induction by TNBS and Sample Administration

One group of the test animals was used as a normal group, and the test animals of the other groups were treated with 2,4,6-trinitrobenzenesulfonic acid (TNBS) to induce acute colitis. Specifically, the test animals were lightly anesthetized with ether, and then a mixture solution of 2.5 g of TNBS (2,4,6-trinitrobenzene sulfonic acid) an 100 ml of 50% ethanol was administered into the colon through the anal in an amount of 0.1 ml each time by use of a 1-ml round-tip syringe, and lifted vertically and maintained for 30 seconds, thereby inducing inflammation. On the other hand, the normal group was orally administered with 0.1 ml of saline. On the next day, the lactic acid bacteria or the lactic acid bacteria mixture as a test sample was suspended in saline and administered orally to each mouse in an amount of $2.0 \times 10^9$ CFU, once a day for three days. On the next day following the end of sample administration, the animals were killed with carbon dioxide, and a colon portion ranging from the cecum to the site just before the anus was dissected and used. Meanwhile, the test animals of the normal group were orally administered with saline alone instead of the lactic acid bacteria. In addition, the test animals of the negative control group were orally administered with saline alone instead of the lactic acid bacteria after the induction of colitis by TNBS. Furthermore, the test animals of the positive control group were orally administered with 50 mg/kg of sulfasalazine, which is a drug for treating colitis, instead of the lactic acid bacteria.

(3) Macroscopic Analysis of Colon

The length and appearance of the dissected colon were observed, and the appearance was analyzed by scoring according to the criteria (Hollenbach et al., 2005, Criteria for Degree of Colitis) shown in Table 22 below. After complete removal of colon contents, the colon tissue was washed with saline. A portion of the washed colon tissue was fixed with 4% formaldehyde solution in order to use it as a pathological tissue sample, and the remainder was freeze-stored at −80° C. for molecular biological analysis.

TABLE 22

| Macroscopic score | Criteria |
|---|---|
| 0 | Any ulcer and inflammation are not found. |
| 1 | Edema without bleeding is found. |
| 2 | Ulcer with edema is found. |
| 3 | Ulcer and inflammation are found at only one site. |
| 4 | Ulcer and inflammation are found at two or more sites. |
| 5 | Ulcer has an increased size of 2 cm or more. |

(4) Measurement of Myeloperoxidase (MPO) Activity 100 mg of colon tissue was homogenized in 200 μl of 10 mM potassium phosphate buffer (pH 7.0) containing 0.5% hexadecyl trimethyl ammonium bromide. The homogenized tissue was centrifuged at 10,000×g and 4° C. for 10 minutes, and the supernatant was collected. 50 μl of the supernatant was added to 0.95 ml of a reaction solution (containing 1.6 mM tetramethyl benzidine and 0.1 mM $H_2O_2$) and allowed to react at 37° C., and the absorbance at 650 nm was measured at various time points during the reaction. To calculate myeloperoxidase (MPO) activity, 1 μmol/ml of peroxide produced by the reaction was used as 1 unit.

(5) Measurement of Inflammatory Marker

Using a Western blotting method, inflammatory markers such as p-p65, p65, iNOS, COX-2 and β-actin were measured.

Specifically, according to the same method as the experiment for measurement of myeloperoxidase (MPO) activity, a supernatant was obtained. 50 μg of the supernatant was taken and electrophoresed on SDS 10% (w/v) polyacrylamide gel for 1 hour and 30 minutes. The electrophoresed sample was transferred to a nitrocellulose membrane under the conditions of 100 V and 400 mA for 1 hour and 10 minutes. The sample-transferred nitrocellulose membrane was blocked with 5% skim milk for 30 minutes, and then washed three times with PBS-Tween for 5 minutes each time, and incubated with a 1:100 dilution of primary antibody (Santa Cruz Biotechnology, USA) overnight. Next, the membrane was washed three times for 10 minutes each time, and incubated with a 1:1000 dilution of secondary antibody (Santa Cruz Biotechnology, USA) for 1 hour and 20 minutes. Next, the membrane was washed three times for 15 minutes each time, and it was developed by fluorescence and visualized.

In addition, inflammation-related cytokines such as TNF-α, IL-17, IL-10 and the like were measured using an ELISA kit.

(6) Analysis of Immune Regulatory Markers

Dissected colon was washed twice with 2.5 mM EDTA solution. The washed colon was agitated in RPMI medium containing 1 mg/ml collagenase type VIII (Sigma) at 30° C. for 20 minutes and was filtered to separate the Lamina propria. Next, the Lamina propria was treated with 30-100% percoll solution and centrifuged to separate T cells. The separated T cells were stained with anti-FoxP3 or anti-IL-17A antibody, and the distribution of Th17 and Treg cells was analyzed using a FACS (fluorescence-activated cell sorting) system (C6 Flow Cytometer® System, San Jose, Calif., USA).

(7) Experimental Results

Table 23 below shows the effects of the lactic acid bacteria on the weight of the colon, the appearance of the colon, myeloperoxidase (MPO) activity and inflammation-related cytokine contents when the lactic acid bacteria were administered to the model animals having TNBS-induced acute colitis. As shown in Table 23 below, the model animals having acute colitis induced by TNBS showed reduced weight, reduced macroscopic score of the colon, reduced colon length and increased MPO activity. However, when the lactic acid bacteria were administered to the model animals having acute colitis induced by TNBS, all these markers were improved. In particular, administration of *Bifidobacterium longum* LC67 alone or administration of a mixture of *Bifidobacterium longum* LC67 and *Lactobacillus plantarum* LC5 showed a very excellent effect on the alleviation of colitis. In addition, the model animals having acute colitis induced by TNBS showed increased TNF-α and IL-17 levels and decreased IL-10 levels. However, when the lactic acid bacteria were administered to the model animals having acute colitis induced by TNBS, all these markers were improved. In particular, when *Bifidobacterium longum* LC67 was administered alone or a mixture of *Bifidobacterium longum* LC67 and *Lactobacillus plantarum* LC5 was administered, TNF-α and IL-17 levels greatly decreased, and IL-10 levels greatly increased.

TABLE 23

| Test groups | Weight gain (g) | Macroscopic score | Colon length (cm) | MPO activity (μU/mg) | TNF-α (pg/mg) | IL-17 (pg/mg) | IL-10 (pg/mg) |
| --- | --- | --- | --- | --- | --- | --- | --- |
| Normal group | 0.64 | 5.9 | 0.14 | 0.42 | 35.1 | 18.4 | 61.2 |
| Negative control group | −2.46 | 4.2 | 2.32 | 1.54 | 95.5 | 65.2 | 30.7 |
| Group administered with LC5 | −1.90 | 4.65 | 1.30 | 0.91 | 75.5 | 52.8 | 43.9 |
| Group administered with LC27 | −1.0 | 4.56 | 1.08 | 0.82 | 67.2 | 50.4 | 44.0 |
| Group administered with LC67 | −0.28 | 4.92 | 0.50 | 0.43 | 48.5 | 38.5 | 54.6 |
| Group administered with LC 68 | −1.02 | 4.5 | 1.34 | 1.04 | 54.4 | 50.5 | 48.1 |
| Group administered with LC5 + LC67 | −0.3 | 5.08 | 0.84 | 0.42 | 45.1 | 37.3 | 55.3 |
| Group administered with LC27 + LC68 | −1.15 | 4.8 | 1.17 | 0.78 | 59.8 | 45.0 | 50.0 |
| Positive control group | −0.91 | 4.58 | 1.43 | 0.95 | 58.2 | 48.5 | 45.5 |

Figure 22:
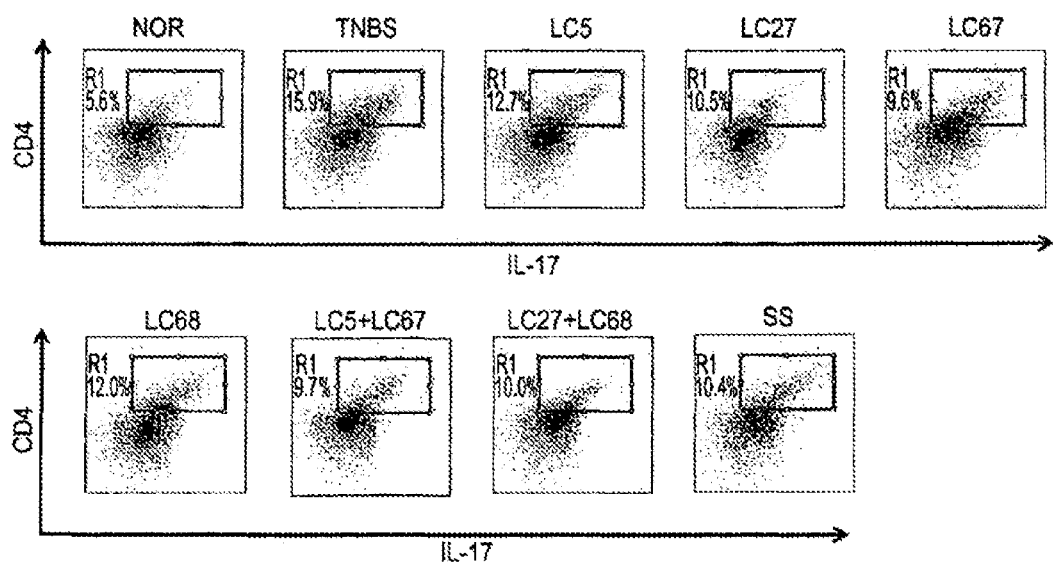
FIG. 22 shows the differentiation patterns of T cells into Th17 cells indicating the effect of lactic acid bacteria on model animals having acute colitis induced by TNBS, in a second experiment of the present invention.
Figure 23:
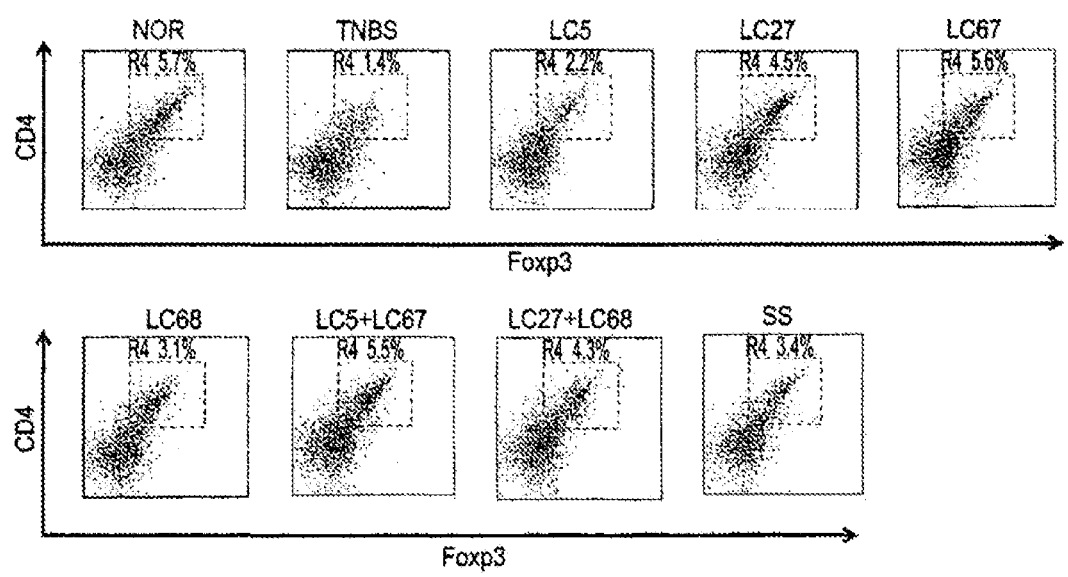
FIG. 23 shows the differentiation patterns of T cells into Treg cells indicating the effect of lactic acid bacteria on model animals having acute colitis induced by TNBS, in a second experiment of the present invention.

FIG. 22 shows the differentiation patterns of T cells into Th17 cells, which indicate the effect of lactic acid bacteria on model animals having acute colitis induced by TNBS, and FIG. 23 shows the differentiation patterns of T cells into Treg cells, which indicate the effect of lactic acid bacteria on model animals having acute colitis induced by TNBS. In FIGS. 22 and 23, "NOR" indicates a normal group; "TNBS" indicates a negative control group; "LC5" indicates a group administered with *Lactobacillus plantarum* LC5; "LC27" indicates a group administered with *Lactobacillus plantarum* LC27, "LC67" indicates a group administered with *Bifidobacterium longum* LC67; "LC68" indicates a group administered with *Bifidobacterium longum* LC68; "LC5+LC67" indicates a group administered with a lactic acid bacteria mixture prepared by mixing *Lactobacillus plantarum* LC5 and *Bifidobacterium longum* LC67 in the same amount; "LC27+LC68" indicates a group administered with a lactic acid bacteria mixture prepared by mixing *Lactobacillus plantarum* LC27 and *Bifidobacterium longum* LC68 in the same amount; and "SS" indicates a group administered with sulfasalazine. As shown in FIGS. 22 and 23, in the case of the animals having acute colitis induced by TNBS, the differentiation of T cells into Th17 cells was promoted, and the differentiation of T cells into Treg cells was inhibited. However, when the lactic acid bacteria were administered to the animals having acute colitis induced by TNBS, the differentiation of T cells into Th17 cells was inhibited, and the differentiation of T cells into Treg cells was promoted. In particular, when *Bifidobacterium longum* LC67 was administered alone or a mixture of *Bifidobacterium longum* LC67 and *Lactobacillus plantarum* LC5 was administered, the differentiation of T cells into Th17 cells was significantly inhibited, and the differentiation of T cells into Treg cells was significantly promoted.

Figure 24:
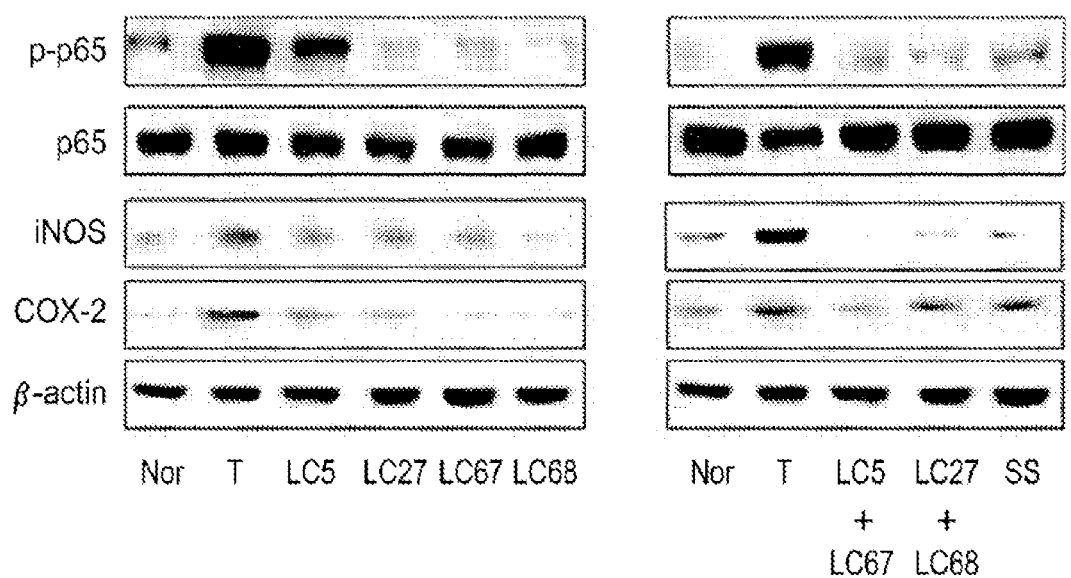
FIG. 24 shows inflammatory response markers indicating the effect of lactic acid bacteria on model animals having acute colitis induced by TNBS, in a second experiment of the present invention.

FIG. 24 shows inflammatory response markers indicating the effect of lactic acid bacteria on model animals having acute colitis induced by TNBS. In FIG. 24, "Nor" indicates a normal group; "T" indicates a negative control group; "LC5" indicates a group administered with *Lactobacillus plantarum LC5*; "LC27" indicates a group administered with *Lactobacillus plantarum* LC27; "LC67" indicates a group administered with *Bifidobacterium longum* LC67; "LC68" indicates a group administered with *Bifidobacterium longum* LC68; "LC5+LC67" indicates a group administered with a lactic acid bacteria mixture prepared by mixing *Lactobacillus plantarum* LC5 and *Bifidobacterium longum* LC67 in the same amount; "LC27+LC68" indicates a group administered with a lactic acid bacteria mixture prepared by mixing *Lactobacillus plantarum* LC27 and *Bifidobacterium longum* LC68 in the same amount, and "SS" indicates a group administered with sulfasalazine. As shown in FIG. 24, in the case of the model animals having acute colitis induced by TNBS, NF-κB was activated (p-p65) and the expression levels of COX-2 and iNOS increased. However, when the lactic acid bacteria were administered, the activation of NF-κB (p-p65) was inhibited, and the expression levels of COX-2 and iNOS also decreased. In particular, administration of *Bifidobacterium longum* LC67 alone or administration of a mixture of *Bifidobacterium longum* LC67 and *Lactobacillus plantarum* LC5 exhibited excellent effects on the inhibition of NF-κB activation (p-p65) and on the inhibition of expression of COX-2 and iNOS.

7. In Vivo Evaluation of the Effect of Lactic Acid Bacteria on Alleviation of Alcohol-Induced Gastric Ulcer (1) Test Animals 5-Week-old C57BL/6 male mice (24-27 g) were purchased from OrientBio, and housed under controlled environmental conditions (humidity: 50±10%, temperature: 25±2° C., 12-hr light/12-hr dark cycle), and then used in the experiment. As feed, standard experimental feed (Samyang, Korea) was used, and the animals had access to drinking water ad libitum. In all the experiments, one group consisted of 6 animals.

(2) Induction of Gastric Ulcer by Alcohol and Administration of Sample

To one test group, $1×10^9$ CFU of *Lactobacillus plantarum* LC27 suspended in saline was orally administered once a day for 3 days. To another test group, $1×10^9$ CFU of *Bifidobacterium longum* LC67 suspended in saline was orally administered once a day for 3 days. To still another test group, $1×10^9$ CFU of a lactic acid bacteria mixture prepared by mixing *Lactobacillus plantarum* LC27 and *Bifidobacterium longum* LC67 in the same amount was orally administered once a day for 3 days, after it was suspended in saline. In addition, to a positive control group, ranitidine, a commercial agent for treating gastric ulcer, was orally administered once a day for 3 days in an amount of 50 mg/kg. In addition, to a normal group and a negative control group, 0.2 ml of saline was orally administered one a day for 3 days. After the sample was orally administered for 3 days, the test mice were fasted and water-deprived for 18 hours. On day 4 of the experiment, at 1 hour after administration of saline, 0.2 ml of 99% pure ethanol was administered orally to the mice of all the test groups other than the normal group to induce gastric ulcer. In addition, to the normal group, 0.2 ml of saline was administered instead of ethanol.

(3) Measurement of Macroscopic Marker Related to Gastric Injury

3 Hours after administration of ethanol, the test mice were sacrificed and gastric tissue was dissected split longitudinally and washed with PBS (phosphate buffer saline) solution, and then the degree of gastric injury was observed visually or microscopically and scored (see Park, S. W., Oh, T. Y., Kim, Y. S., Sim, H., et al., *Artemisia asiatica* extracts protect against ethanol-induced injury in gastric mucosa of rats. J. Gastroenterol. Hepatol. 2008, 23, 976-984).

(4) Measurement of Myeloperoxidase (MPO) Activity 100 mg of the gastric tissue was homogenized in 200 μl of mM potassium phosphate buffer (pH 7.0) containing 0.5% hexadecyl trimethyl ammonium bromide. Then, the tissue solution was centrifuged at 10,000×g and 4° C. for 10 minutes, and the supernatant was collected. 50 μl of the supernatant was added to 0.95 ml of a reaction solution (containing 1.6 mM tetramethyl benzidine and 0.1 mM $H_2O_2$) and allowed to react at 37° C., and the absorbance at 650 nm was measured at various time points during the reaction. To calculate myeloperoxidase (MPO) activity, 1 μmol/ml of peroxide produced by the reaction was used as 1 unit.

(5) Measurement of Inflammatory Markers

2 μg of mRNA was isolated from gastric tissue by a Qiagen RNeasy Mini Kit and synthesized into cDNA using Takara Prime Script Rtase. Next, the expression levels of CXCL4 [chemokine (C-X-C motif) ligand 4] and TNF-α (tumor necrosis factor-alpha) were measured using a quantitative real time polymerase chain reaction (Qiagen thermal cycler, Takara SYBER premix agent, Thermal cycling conditions: activation of DNA polymerase for 5 min at 95° C., followed by 40 cycles of amplification for 10 s at 95° C. and for 45 s at 60° C.). Table 24 below shows the primer sequences used to analyze each cytokine in the quantitative real time polymerase chain reaction.

TABLE 24

| Cytokine to be analyzed | Kind of primer | Primer nucleotide sequence |
| --- | --- | --- |
| TNF-α | Forward | 5'-CTGTAGCCCACGTCGTAGC-3' |
|  | Reverse | 5'-TTGAGATCCATGCCGTTG-3' |
| CXCL4 | Forward | 5'-AGTCCTGAGCTGCTGCTTCT-3' |
|  | Reverse | 5'-GATCTCCATCGCTTTCTTCG-3' |

(6) Experimental Results

Figure 25:
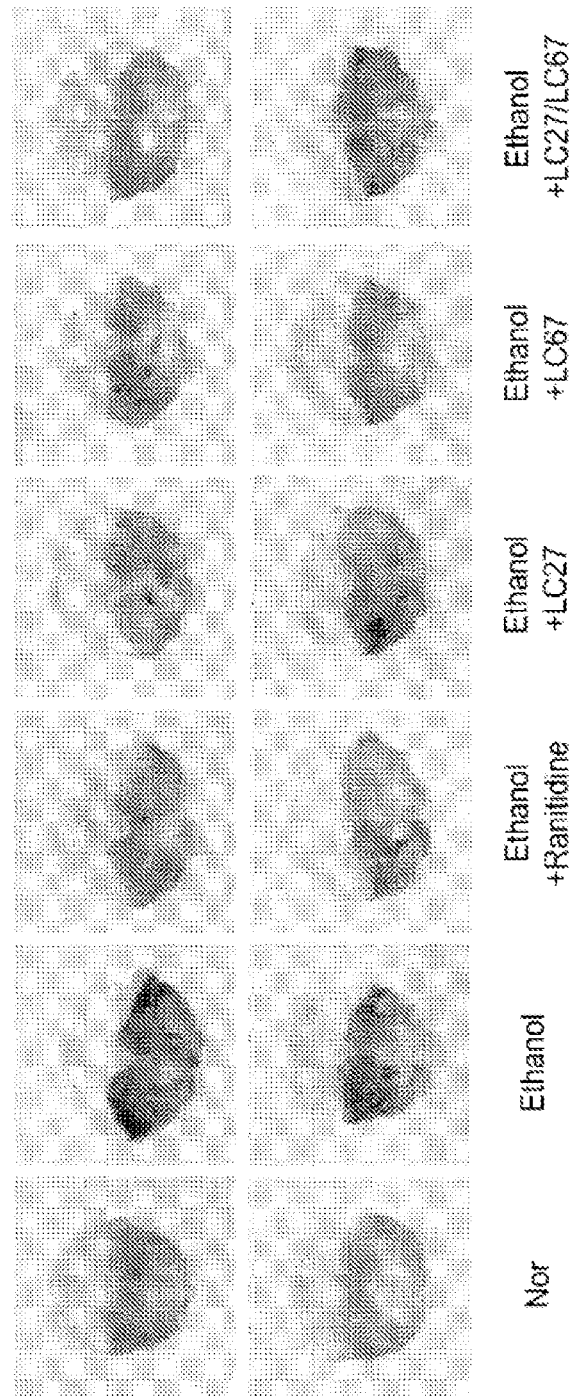
FIG. 25 depicts images showing the effect of lactic acid bacteria on the stomach mucosa of mice having gastric ulcer induced by ethanol, in a second experiment of the present invention.
Figure 26:
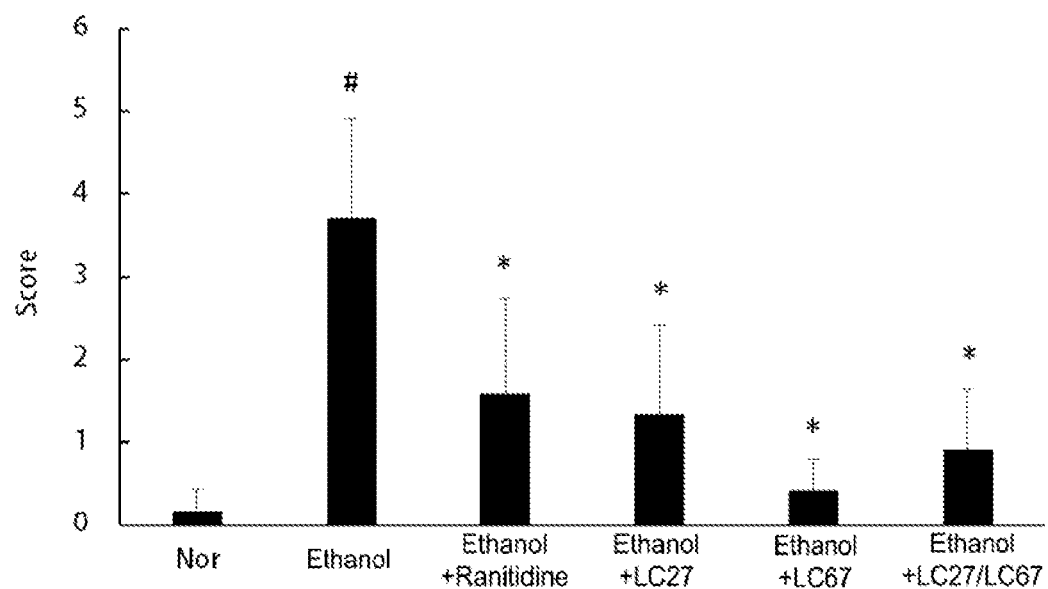
FIG. 26 shows the gross gastric lesion score indicating the effect of lactic acid bacteria on the stomach mucosa of mice having gastric ulcer induced by ethanol, in a second experiment of the present invention.
Figure 27:
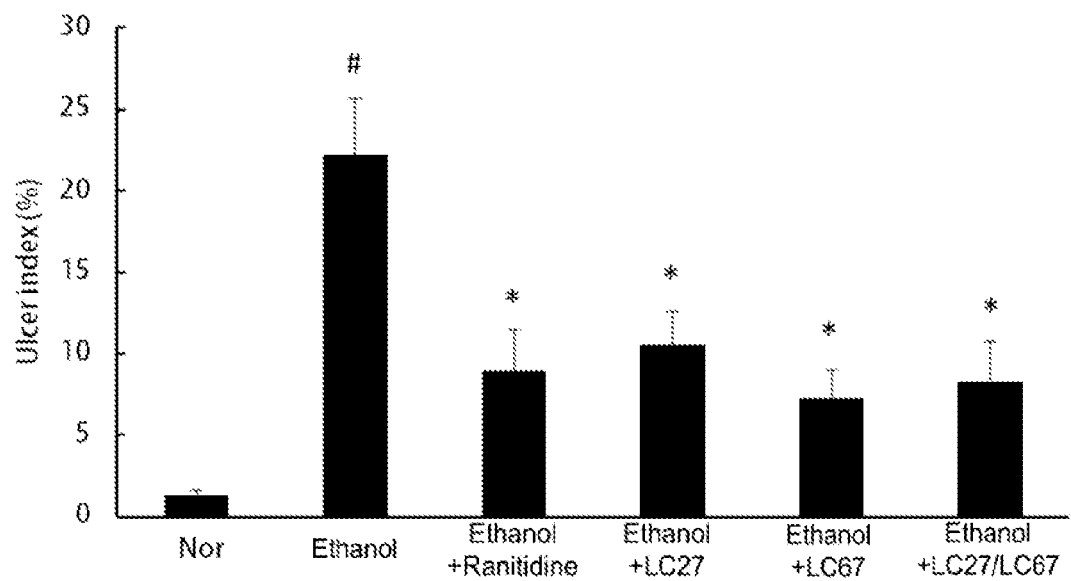
FIG. 27 shows the ulcer index indicating the effect of lactic acid bacteria on the stomach mucosa of mice having gastric ulcer induced by ethanol, in a second experiment of the present invention.
Figure 28:
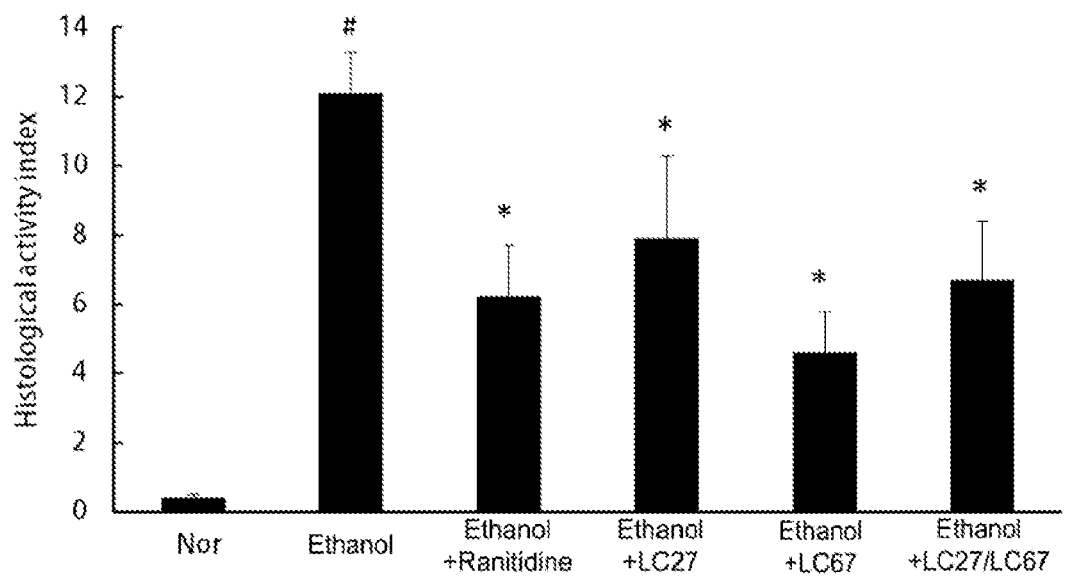
FIG. 28 shows the histological activity index indicating the effect of lactic acid bacteria on the stomach mucosa of mice having gastric ulcer induced by ethanol, in a second experiment of the present invention.
Figure 29:
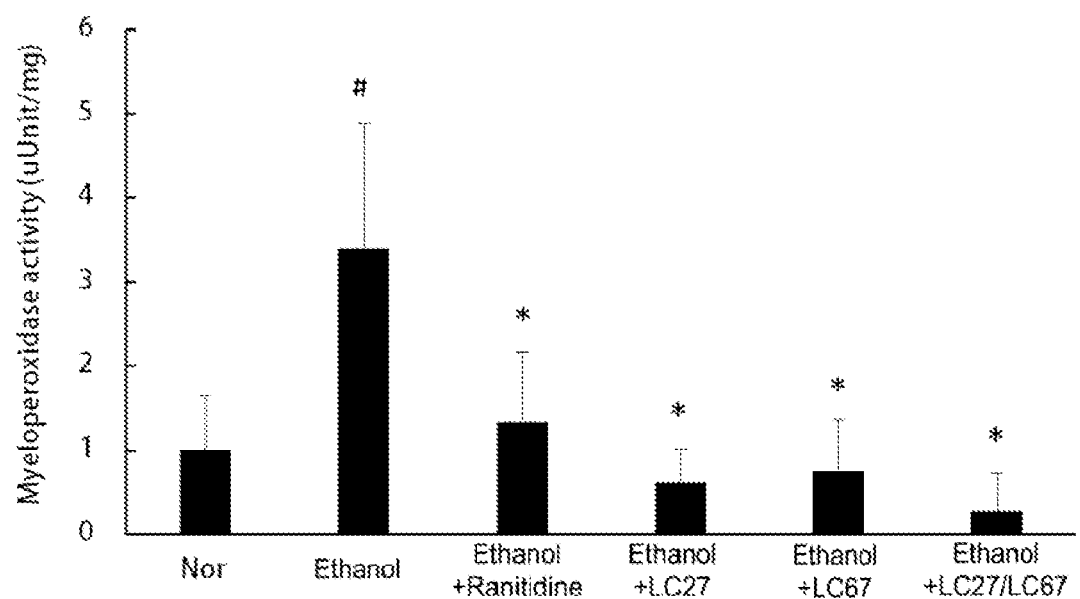
FIG. 29 shows the myeloperoxidase (MPO) activity indicating the effect of lactic acid bacteria on the stomach mucosa of mice having gastric ulcer induced by ethanol, in a second experiment of the present invention.
Figure 30:
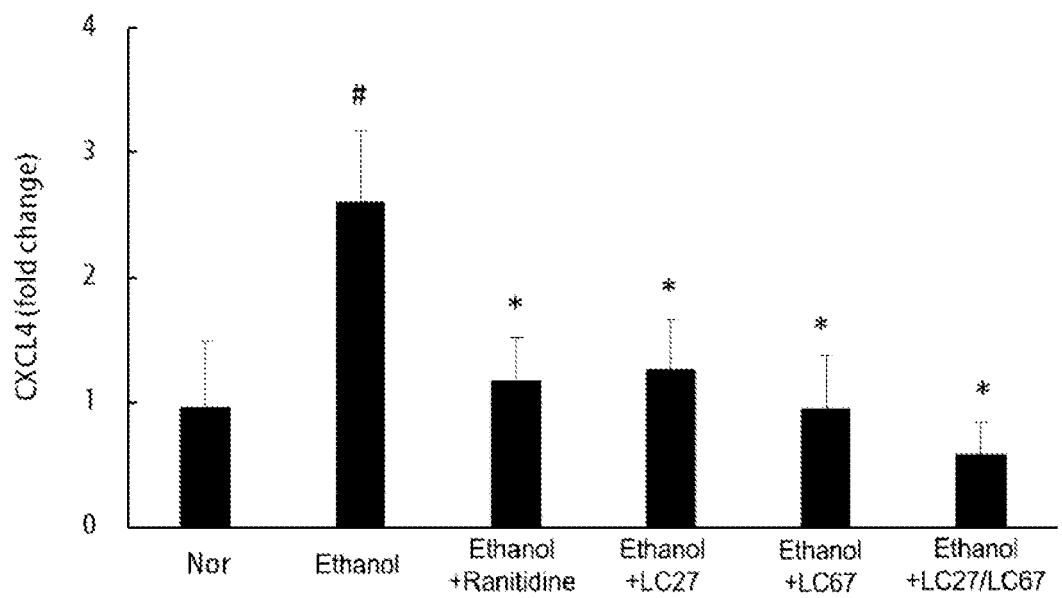
FIG. 30 shows CXCL4 expression levels indicating the effect of lactic acid bacteria on the stomach mucosa of mice having gastric ulcer induced by ethanol, in a second experiment of the present invention.
Figure 31:
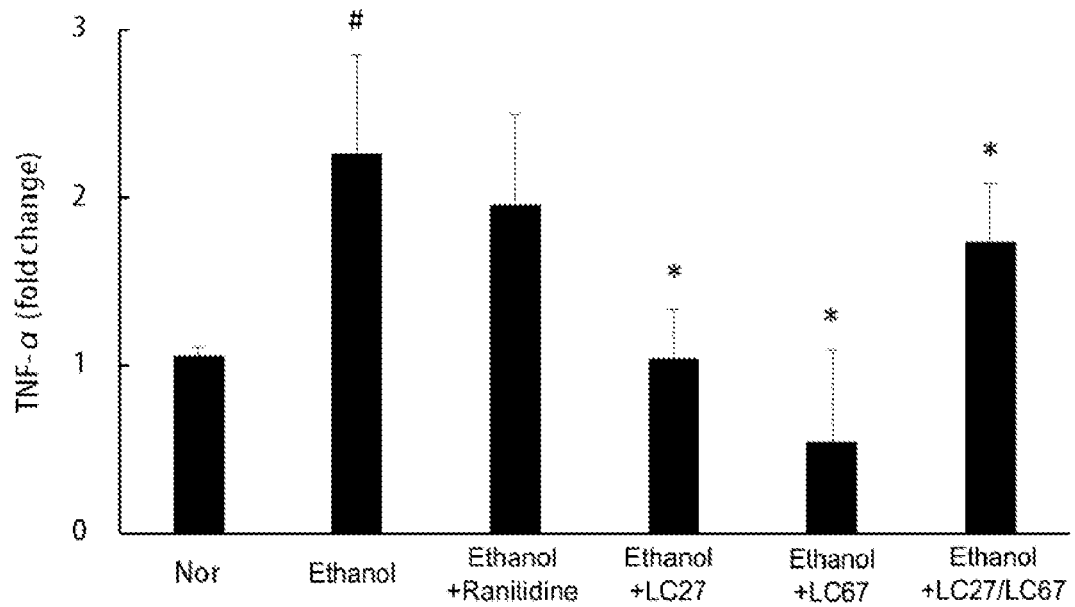
FIG. 31 shows TNF-α expression levels indicating the effect of lactic acid bacteria on the stomach mucosa of mice having gastric ulcer induced by ethanol, in a second experiment of the present invention.

FIG. 25 depicts images showing the effect of lactic acid bacteria on the stomach mucosa of mice having gastric ulcer induced by ethanol, in the second experiment of the present invention; FIG. 26 shows the gross gastric lesion score indicating the effect of lactic acid bacteria on the stomach mucosa of mice having gastric ulcer induced by ethanol, in the second experiment of the present invention; FIG. 27 shows the ulcer index indicating the effect of lactic acid bacteria on the stomach mucosa of mice having gastric ulcer induced by ethanol, in the second experiment of the present invention; and FIG. 28 shows the histological activity index indicating the effect of lactic acid bacteria on the stomach mucosa of mice having gastric ulcer induced by ethanol, in the second experiment of the present invention. Furthermore, FIG. 29 shows the myeloperoxidase (MPO) activity indicating the effect of lactic acid bacteria on the stomach mucosa of mice having gastric ulcer induced by ethanol, in the second experiment of the present invention. In addition, FIG. 30 shows CXCL4 expression levels indicating the effect of lactic acid bacteria on the stomach mucosa of mice having gastric ulcer induced by ethanol, in the second experiment of the present invention; and FIG. 31 shows TNF-α expression levels indicating the effect of lactic acid bacteria on the stomach mucosa of mice having gastric ulcer induced by ethanol, in the second experiment of the present invention. In FIGS. 30 and 31, the CXCL4 expression levels and TNF-α expression levels in the test groups other than the normal group are expressed fold-changes relative to the expression levels in the normal group. In FIGS. 25 to 31, "Nor" indicates a normal group; "Ethanol" indicates a negative control group having ethanol-induced gastric ulcer and administered with saline as a sample; "Ethanol+Ranitidine" indicates a test group having ethanol-induced gastric ulcer and administered with Ranitidine as a sample; "Ethanol+LC27" indicates a test group having ethanol-induced gastric ulcer and administered with *Lactobacillus plantarum* LC27 as a sample; "Ethanol+LC67" indicates a test group having ethanol-induced gastric ulcer and administered with *Bifidobacterium longum* LC67 as a sample; and "Ethanol+LC27/LC67" indicates a test group having ethanol-induced gastric ulcer and administered with a lactic acid bacteria mixture, prepared by mixing *Lactobacillus plantarum* LC27 and *Bifidobacterium longum* LC67 in the same amount, as a sample. As shown in FIGS. 25 to 29, *Bifidobacterium longum* LC67, *Lactobacillus plantarum* LC27 or a mixture thereof effectively alleviated the gastric injury or gastric ulcer induced by ethanol. Furthermore, as shown in FIGS. 30 and 31, *Bifidobacterium longum* LC67, *Lactobacillus plantarum* LC27 or a mixture thereof greatly reduced the inflammatory marker levels in the mice having ethanol-induced gastric injury or gastric ulcer.

8. In Vivo Evaluation of the Effect of Lactic Acid Bacteria on Alleviation of Alcohol-Induced Liver Injury (1) Test Animals 5-Week-old C57BL/6 male mice (24-27 g) were purchased from OrientBio, and housed under controlled environmental conditions (humidity: 50±10%, temperature: 25±2° C., 12-hr light/12-hr dark cycle), and then used in the experiment. As feed, standard experimental feed (Samyang, Korea) was used, and the animals had access to drinking water ad libitum. In all the experiments, one group consisted of 6 animals.

(2) Induction of Liver Injury by Alcohol and Administration of Sample

To one test group, 1×10$^9$ CFU of *Lactobacillus plantarum* LC27 suspended in saline was orally administered once a day for 3 days. To another test group, 1×10$^9$ CFU of *Bifidobacterium longum* LC67 suspended in saline was orally administered once a day for 3 days. To still another test group, 1×10$^9$ CFU of a lactic acid bacteria mixture prepared by mixing *Lactobacillus plantarum* LC27 and *Bifidobacterium longum* LC67 in the same amount was orally administered once a day for 3 days, after it was suspended in saline. To a positive control group, silymarin, a commercial agent for treating liver injury, was orally administered once a day for 3 days in an amount of 50 mg/kg. In addition, to a normal group and a negative control group, 0.1 ml of saline was orally administered once a day for 3 days. 3 hours after 3 days of oral administration of the sample or saline, ethanol was administered intraperitoneally to the mice of all the test groups other than the normal group in an amount of 6 ml/kg in order to induce liver injury. In addition, to the normal group, saline in place of ethanol was administered intraperitoneally in an amount of 6 ml/kg. Next, the test mice were fasted and water-deprived for 12 hours, and then sacrificed, and blood was taken from the heart.

(3) Measurement of Liver Function Markers and Results

The taken blood was allowed to stand at room temperature for 60 minutes and centrifuged at 3,000 rpm for 15 minutes to separate serum. The GPT (glutamic pyruvate transaminase) and GOT (glutamic oxalacetic transaminase) levels in the separated serum were measured using a blood assay kit (ALT & AST measurement kit; Asan Pharm. Co., Korea), and the results of the measurement are shown in Table 25 below. As shown in Table 25 below, *Bifidobacterium longum* LC67, *Lactobacillus plantarum* LC27 or a mixture thereof effectively alleviated ethanol-induced liver injury. In particular, *Bifidobacterium longum* LC67 showed a better effect than silymarin which is a commercial agent for treating liver injury.

TABLE 25

| Test groups | GOT (IU/L) | GPT (IU/L) |
|---|---|---|
| Normal group | 52.1 | 42.2 |
| Negative control group | 107.7 | 156.3 |
| Group administered with ethanol and LC27 | 82.3 | 95.4 |
| Group administered with ethanol and LC67 | 62.5 | 65.8 |
| Group administered with ethanol and LC27/LC67 | 71.4 | 78.3 |
| Group administered with ethanol and silymarin | 79.5 | 87.5 |

\* LC27: *Lactobacillus plantarum* LC27
\* LC67: *Bifidobacterium longum* LC67
\* LC27/LC67: lactic acid bacteria mixture prepared by mixing *Lactobacillus plantarum* LC27 and *Bifidobacterium longum* LC67 in the same amount.

Although the present invention has been described above with reference to the examples, the scope of the present invention is not limited to these examples, and various modifications are possible without departing from the scope and idea of the present invention. Therefore, the scope of protection of the present invention should be interpreted to include all embodiments falling within the appended claims.

The invention claimed is:

1. A method of treating one or more diseases selected from a group consisting of intestinal damage, liver injury, allergic disease and inflammatory disease, comprising administering a composition comprising *Lactobacillus plantarum* LC27 (accession number: KCCM 11801P), a culture thereof, a lysate thereof or an extract thereof to a subject, wherein the intestinal damage is intestinal permeability syndrome; the liver injury is selected from a group consisting of hepatitis, fatty liver and liver cirrhosis; the allergic disease is selected from a group consisting of atopic dermatitis, asthma, pharyngitis and chronic dermatitis and wherein the inflammatory disease is selected from a group consisting of gastritis, gastric ulcer, colitis and arthritis; and wherein the *Lactobacillus plantarum* LC27 has antioxidant activity, beta-glucuronidase inhibitory activity, lipopolysaccharide (LPS) production inhibitory activity and tight junction protein expression-inducing activity.

2. The method according to claim 1, wherein the *Lactobacillus plantarum* LC27 comprises a 16S rDNA nucleotide sequence of SEQ ID NO: 5.

3. The method according to claim 1, wherein the composition further comprises one or more lactic acid bacteria selected from a group consisting of *Lactobacillus brevis* CH23 (accession number: KCCM 11762P), *Bifidobacterium longum* CH57 (accession number: KCCM 11764P), *Lactobacillus plantarum* LC5 (accession number: KCCM 11800P) and *Bifidobacterium longum* LC67 (accession number: KCCM 11802P).

4. The method according to claim 1, wherein the composition further comprises *Bifidobacterium longum* LC67 (accession number: KCCM 11802P), a culture thereof, a lysate thereof or an extract thereof.

* * * * *